US012714802B2

(12) United States Patent
Johansen et al.

(10) Patent No.: US 12,714,802 B2
(45) Date of Patent: Aug. 25, 2026

(54) AUTO INJECTOR WITH CASSETTE

(71) Applicant: PHILLIPS-MEDISIZE A/S, Struer (DK)

(72) Inventors: Esben Weldingh Johansen, Struer (DK); Jan Olesen, Holstebro (DK); Niels Skovby Rahbek, Holstebro (DK); Bent Larsen, Struer (DK); Ole Lemming, Haderup (DK)

(73) Assignee: PHILLIPS-MEDISIZE A/S, Struer (DK)

(*) Notice: Subject to any disclaimer, the term of this patent is extended or adjusted under 35 U.S.C. 154(b) by 198 days.

(21) Appl. No.: 17/636,027

(22) PCT Filed: Apr. 6, 2020

(86) PCT No.: PCT/EP2020/059737
§ 371 (c)(1),
(2) Date: Feb. 17, 2022

(87) PCT Pub. No.: WO2021/069106
PCT Pub. Date: Apr. 15, 2021

(65) Prior Publication Data

US 2022/0280725 A1 Sep. 8, 2022

(30) Foreign Application Priority Data

Oct. 7, 2019 (WO) ................ PCT/EP2019/077061
Oct. 7, 2019 (WO) ................ PCT/EP2019/077065
Oct. 7, 2019 (WO) ................ PCT/EP2019/077068

(51) Int. Cl.
*A61M 5/32* (2006.01)
*A61M 5/20* (2006.01)
(Continued)

(52) U.S. Cl.
CPC ............ *A61M 5/3204* (2013.01); *A61M 5/20* (2013.01); *A61M 5/2053* (2013.01); *A61M 5/24* (2013.01);
(Continued)

(58) Field of Classification Search
CPC .. A61M 2005/2492; A61M 2005/2485; A61M 2005/2418; A61M 2005/2411;
(Continued)

(56) References Cited

U.S. PATENT DOCUMENTS 3,702,608 A 11/1972 Tibbs
8,652,100 B1 * 2/2014 Cowe ................. A61M 5/2033 604/117

(Continued)

FOREIGN PATENT DOCUMENTS

CN 101547715 A 3/2012
CN 101903057 A 3/2013

(Continued)

OTHER PUBLICATIONS

International Preliminary Report on Patentability for PCT Application No. PCT/EP2019/077065, mailed on Apr. 15, 2021, 08 pages.

(Continued)

*Primary Examiner* — Emily L Schmidt
*Assistant Examiner* — Samuel J Marrison

(57) ABSTRACT

The invention also relates to an improved auto injector adapted for receiving a cassette with medicament and for administering the medicament in the cassette to a patient, the auto injector extending from a proximal end to a distal end along a longitudinal axis, wherein the cassette is removable received in the auto injector along the longitudinal direction.

26 Claims, 22 Drawing Sheets

(51) Int. Cl.
*A61M 5/24* (2006.01)
*A61M 5/28* (2006.01)
*A61M 5/315* (2006.01)

(52) U.S. Cl.
CPC .......... *A61M 5/28* (2013.01); *A61M 5/31505* (2013.01); *A61M 5/31576* (2013.01); *A61M 5/31578* (2013.01); *A61M 5/3158* (2013.01); *A61M 5/3202* (2013.01); *A61M 5/3216* (2013.01); *A61M 2005/2013* (2013.01); *A61M 5/2033* (2013.01); *A61M 2005/206* (2013.01); *A61M 2005/2073* (2013.01); *A61M 2005/208* (2013.01); *A61M 2005/2411* (2013.01); *A61M 5/2422* (2013.01); *A61M 2005/2433* (2013.01); *A61M 2005/2492* (2013.01); *A61M 2005/31588* (2013.01); *A61M 2205/12* (2013.01); *A61M 2205/121* (2013.01); *A61M 2205/13* (2013.01); *A61M 2205/14* (2013.01); *A61M 2205/3327* (2013.01); *A61M 2205/42* (2013.01)

(58) Field of Classification Search
CPC ............ A61M 2005/208; A61M 5/283; A61M 2005/2407; A61M 2005/2403; A61M 2005/2433; A61M 2005/14573; A61M 5/2429; A61M 5/14546; A61M 5/1458; A61M 2005/2013; A61M 2005/2429
See application file for complete search history.

(56) References Cited

U.S. PATENT DOCUMENTS

| | | | |
|---|---|---|---|
| 9,592,340 | B2 | 3/2017 | Hourmand |
| 2003/0105430 | A1 | 6/2003 | Lavi et al. |
| 2005/0049561 | A1 | 3/2005 | Hommann et al. |
| 2011/0004165 | A1 | 1/2011 | Iio |
| 2011/0022461 | A1 | 1/2011 | Simeonov |
| 2011/0301566 | A1 | 12/2011 | Schaefer |
| 2012/0191047 | A1* | 7/2012 | Raday ................. A61M 5/2033 604/198 |
| 2013/0150801 | A1 | 6/2013 | Ekman |
| 2013/0172819 | A1 | 7/2013 | Iio et al. |
| 2013/0274677 | A1 | 10/2013 | Ekman |
| 2013/0310746 | A1* | 11/2013 | Wozencroft ............ A61M 5/20 29/700 |
| 2014/0309591 | A1 | 10/2014 | Holmqvist |
| 2015/0265765 | A1 | 9/2015 | Yavorsky et al. |
| 2015/0273151 | A1* | 10/2015 | McLoughlin ......... A61M 5/002 604/66 |
| 2016/0095983 | A1 | 4/2016 | Lewkonya et al. |
| 2016/0120751 | A1* | 5/2016 | Mounce .................. A61P 19/10 604/404 |
| 2016/0354556 | A1* | 12/2016 | Zucker .................. A61M 5/326 |
| 2017/0000955 | A1 | 1/2017 | Mcloughlin et al. |
| 2017/0173269 | A1* | 6/2017 | Wozencroft ........ A61M 5/3257 |
| 2018/0104413 | A1* | 4/2018 | McLoughlin ......... A61M 5/204 |
| 2018/0361078 | A1 | 12/2018 | Young |
| 2019/0001060 | A1 | 1/2019 | Gylleby et al. |
| 2023/0016544 | A1 | 1/2023 | Hutt |

FOREIGN PATENT DOCUMENTS

| | | | |
|---|---|---|---|
| CN | 103025373 | A | 4/2013 |
| CN | 103328024 | A | 9/2013 |
| CN | 103458945 | A | 12/2013 |
| CN | 105025954 | A | 11/2015 |
| CN | 105451792 | A | 3/2016 |
| CN | 105636623 | A | 6/2016 |
| CN | 105792866 | A | 7/2016 |
| CN | 108136119 | A | 6/2018 |
| CN | 109789263 | A | 5/2019 |
| EP | 2489380 | A1 | 8/2012 |
| GB | 2471473 | A | 1/2011 |
| JP | S60179068 | A | 9/1985 |
| JP | 2001090638 | A | 4/2001 |
| JP | 2005074224 | A | 3/2005 |
| JP | 2007111518 | A | 5/2007 |
| JP | 2008504934 | A | 2/2008 |
| JP | 2015523131 | A | 8/2015 |
| JP | 2016112305 | A | 6/2016 |
| JP | 2016539705 | A | 12/2016 |
| JP | 2017526490 | A | 9/2017 |
| JP | 2017531459 | A | 10/2017 |
| WO | 0024441 | A1 | 5/2000 |
| WO | 2006007556 | A2 | 1/2006 |
| WO | 2009143255 | A1 | 11/2009 |
| WO | 2010076569 | A2 | 7/2010 |
| WO | 2012066767 | A1 | 5/2012 |
| WO | 2013141351 | A1 | 9/2013 |
| WO | 2013186619 | A1 | 12/2013 |
| WO | 2014037946 | A1 | 3/2014 |
| WO | 2014066256 | A1 | 5/2014 |
| WO | 2014143815 | A2 | 9/2014 |
| WO | 2015118550 | A2 | 8/2015 |
| WO | 2017089265 | A1 | 6/2017 |

OTHER PUBLICATIONS

International Preliminary Report on Patentability for PCT Application No. PCT/EP2019/077068, mailed on Apr. 15, 2021, 08 pages.
International Preliminary Report on Patentability received for PCT Application No. PCT/EP2019/077061, mailed on Apr. 15, 2021, 9 Pages.
International Search Report and Written Opinion for PCT Application No. PCT/EP2019/077065, mailed on Feb. 6, 2020, 10 pages.
International Search Report and Written Opinion for PCT Application No. PCT/EP2019/077068, mailed on Dec. 6, 2019, 9 pages.
International Search Report and Written Opinion for PCT Application No. PCT/EP2020/059737, mailed on Jul. 27, 2020, 16 pages.
International Search Report and Written Opinion received for PCT Application No. PCT/EP2019/077061, mailed on Nov. 27, 2019, 10 Pages.
Office Action received for JP Application No. 2021-518766, mailed on Mar. 1, 2022, 12 Pages (06 Pages of English Translation and 06 Pages of Official notification).
Ex-Parte Quayle office action received for U.S. Appl. No. 17/282,005, mailed on Feb. 14, 2024, 6 pages.
Notification of Reasons for Refusal received for JP application No. 2021-518687, mailed on May 10, 2022, 14 pages. (7 pages of english translation and 7 pages of official copy).
Notification of Reasons for Refusal received for JP application No. 2021-518734, mailed on Apr. 26, 2022, 5 pages. (3 pages of english translation and 2 pages of official copy).

* cited by examiner 1104
1169
1102
1156
1159
205
208
1168
550
510
1102
540
1102
540
202
547
567
566
1103
548
204
560
535
531
500, 530
206
530
536

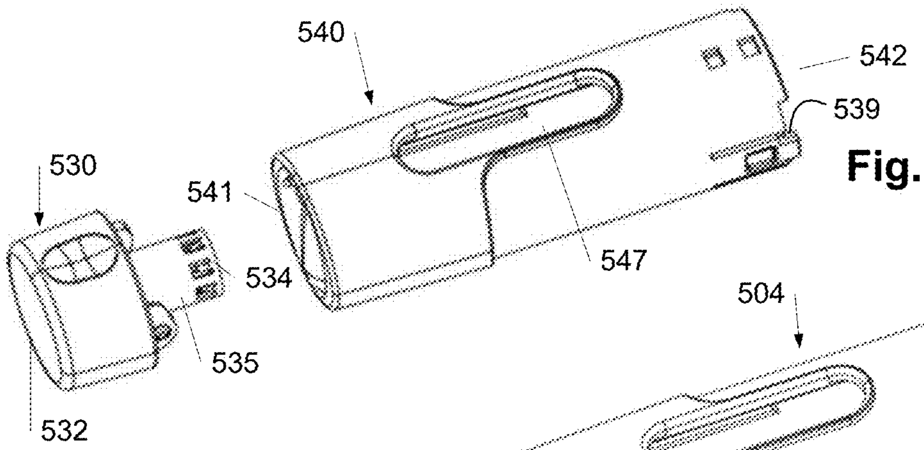
Fig. 8A
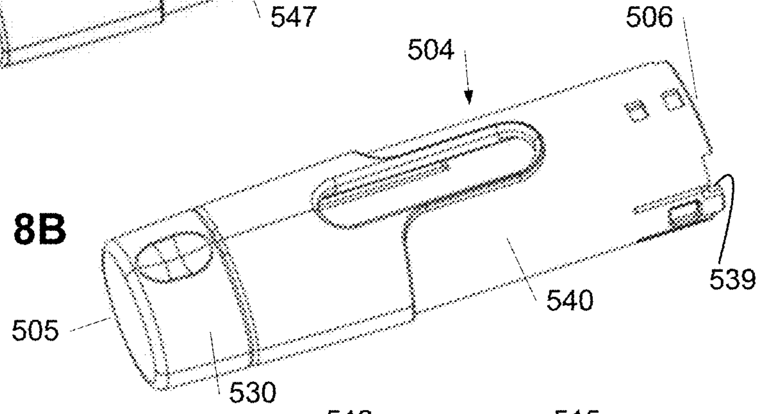
Fig. 8B
Fig. 9A
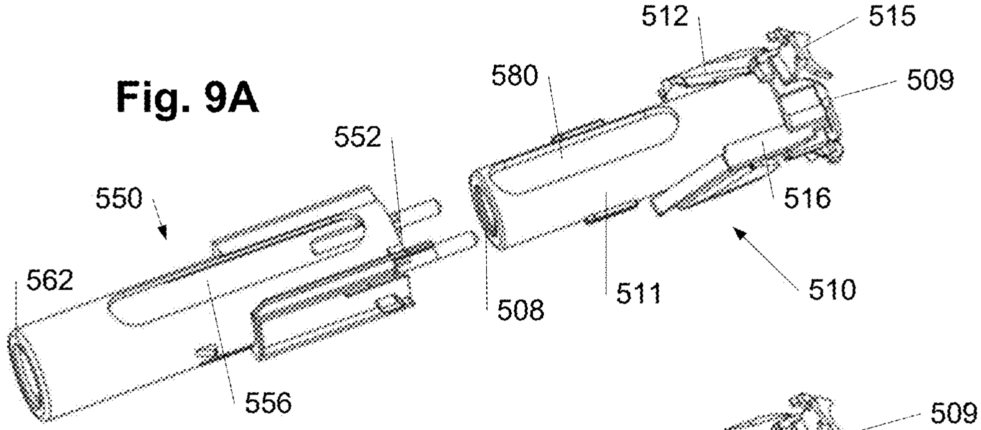
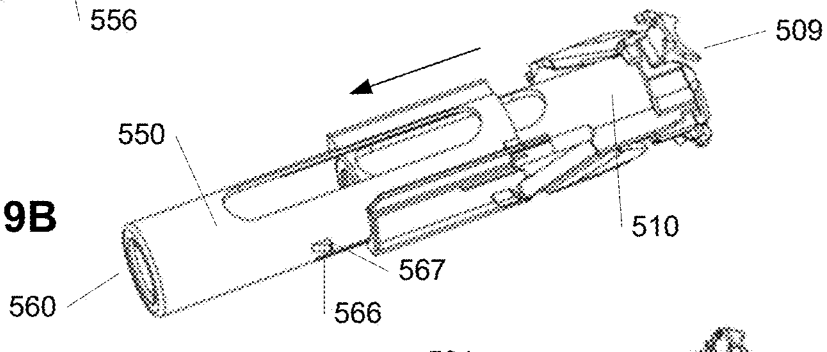
Fig. 9B
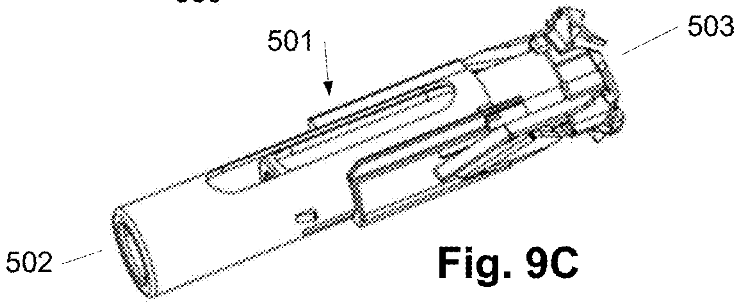
Fig. 9C
540
542
539
530
541
534
547
535
532
506
504
539
505
540
530
512
515
580
509
552
550
516
562
508
511
510
556
509
550
510
567
560
566
501
503
502

571
570
574
573
576
572

570
574
572
576
571

580
516
575
515
510
570
574
512
577

580
516
519
575
570
574
576
510
512
515
577

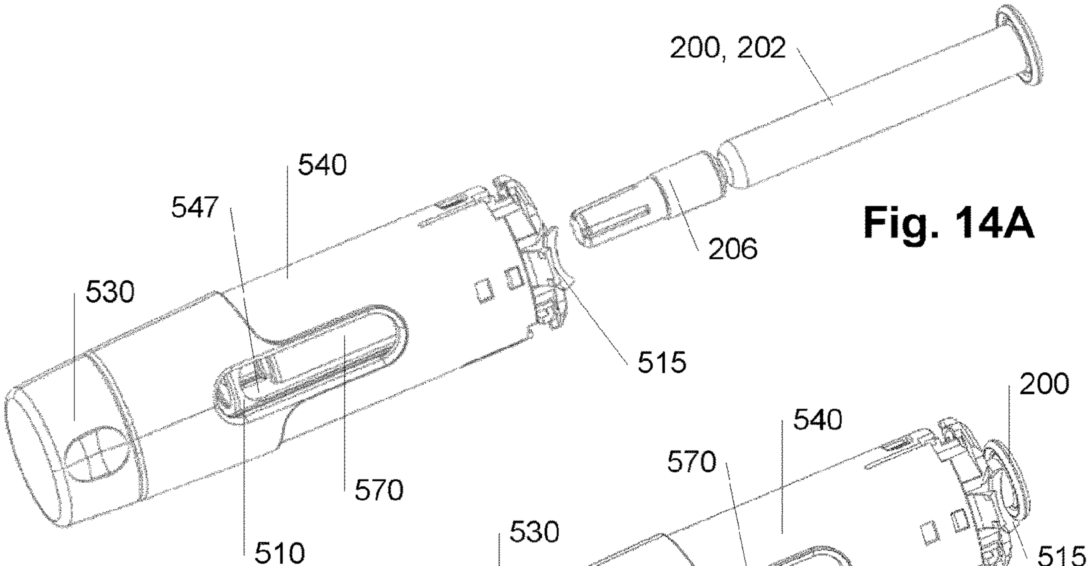
Fig. 14A
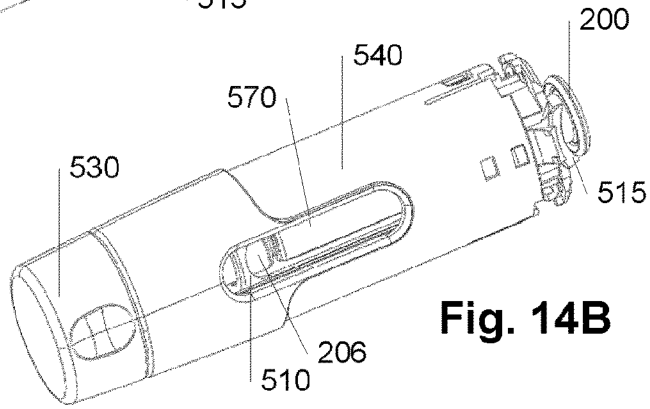
Fig. 14B
Fig. 14C
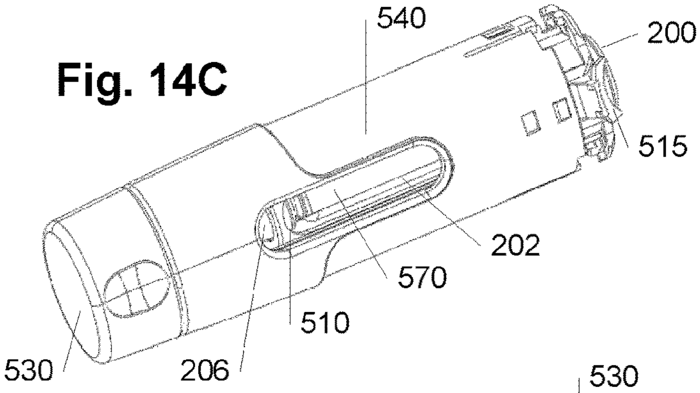
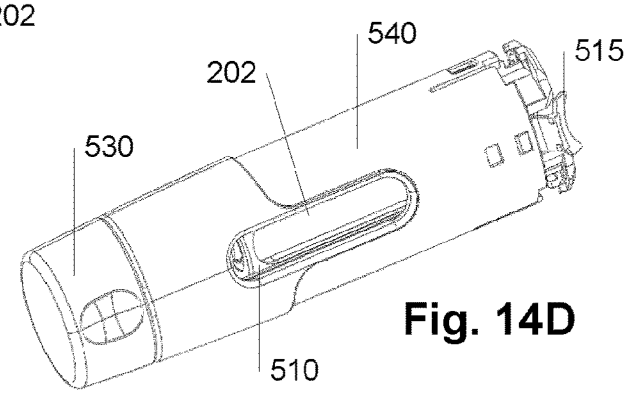
Fig. 14D
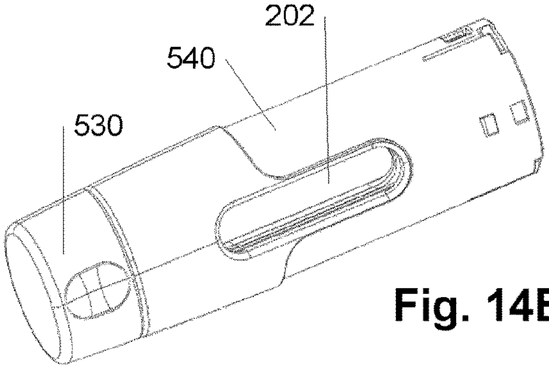
Fig. 14E
200, 202
540
547
530
206
515
570
510
200
540
570
530
515
206
510
540
200
515
202
570
510
530
206
540
515
202
530
510
202
540
530

208
200, 202
540
204
530
535
206
574
570
571
531
510
536
540
571
530
202
510
206
540
515
571
530
202
510
204
206
540
515
571
531
530
202
206
510

1102, 1108
1114b
1118, 1158
1111, 1114a
1102, 1106
1116, 1156
1119, 1159
1117
1109
1115, 1178
1114b
1102, 1106
1000
1107
500
547
1102, 1108
540
530
1102, 1106
1107
547
530
1102, 1108
540

1182
1163
1148
1159
1114a
1154
1174
1184
1159
1168
1178
1169
1114b
1162, 1166
1156
1163, 1167
1168
1158
510
1110
1143
1144
1159
558
516
550
1162, 1166
1156
1158
510
1110
1163, 1167
1143
1144
550
1159
558
516

1162, 1166
1156
1168
558
1110
1163, 1167
1143
550
1158
1159
516
1162, 1166
1156
558
1110
1163, 1167
1143
550
1158
1159
516
204
1162, 1166
1156
1163, 1167
1143
550
1158
558
1159
516
204

1156
1168
1110
1143
1158
558
550
1159
516
204
1156
558
1110
1143
1158
1159
516
550
204
1162, 1166
1158
1156
510
1110
1163, 1167
1143
558
1159
516

AUTO INJECTOR WITH CASSETTE

RELATED APPLICATIONS

This application is a national phase of PCT/EP2020/059737, filed on April 6. 2020, which claims priority to PCT Application Nos. PCT/EP2019/077061, PCT/EP2019/077065 and PCT/EP2019/077068 filed on Oct. 7, 2019, which are incorporated herein by reference in their entireties.

The invention relates to an improved cassette and auto injector system.

BACKGROUND

Auto injectors for the delivery of medicament to a patient comes in many varieties depending on the type of medicament, which is to be delivered to the patient. Assembling of the auto injector and cassette to obtain a good fit between the two parts is often only ensured if the two parts are aligned in a specific manner. The same applies of the assembly of the individual parts in the cassette and the auto injector.

If the auto injector is a re-usable item into which a cassette is inserted, the user needs to ensure that all operational parts stay full functional in order to prolong the lifetime of the auto injector.

SUMMARY

Throughout this description, all references to the proximal direction or proximal surfaces refer to parts, surfaces and similar oriented in the direction of insertion, i.e. in the direction of the insertion needle and the outer part of the auto injector touching the skin during injection of the medicament. Movement of parts in a proximal direction and/or proximately refers to a movement in the direction of the insertion needle and the outer part of the auto injector touching the skin during injection of the medicament.

Likewise, all references to the distal direction or distal surfaces refer to parts, surfaces and similar oriented in the direction away from the direction of the insertion needle, i.e. in the direction of the user. Movement of parts in a distal direction and/or distally refers to a movement in the direction away from the insertion needle and the outer part of the auto injector touching the skin during injection of the medicament, i.e. in the direction of the user.

Disclosed herein in a first aspect is an auto injector adapted for receiving a cassette with medicament and for administering the medicament in the cassette to a patient, the auto injector extending from a proximal end to a distal end along a longitudinal axis, wherein the cassette is removable received in the auto injector along the longitudinal direction, wherein the auto injector further comprises one or more cassette interacting parts adapted for securing and locking the cassette inside the auto injector and for facilitating administering of the medicament, wherein the one or more cassette interacting parts are configured for moving in parallel with the longitudinal axis of the auto injector.

By removable received is meant is meant a disposable cassette, which may be received in a reusable auto injector. The disposable cassette may be a one-time use cassette, or a cassette comprising multiple doses.

By a movement in parallel with the longitudinal axis of the auto injector it is ensured that a minimum of stress is inflicted on the auto injector. This prolongs the lifetime of the auto injector. Further, a slimmer design is obtainable by the movement of the cassette interacting parts in parallel with the longitudinal axis of the auto injector. As the auto injector and the cassette may be constructed to be interfacing with the auto injector and the cassette sharing the same longitudinal axis, the risk of the cassette getting stuck inside in the injector is mitigated. This helps make the connection as slim as possible, and the auto injector as robust as possible.

Disclosed herein in a second aspect is an auto injector adapted for receiving a cassette with medicament and for administering the medicament, wherein the cassette is removable received in the auto injector, wherein the auto injector is consisting of a housing extending from a proximal end to a distal end and a multiple of internal injector parts positioned inside the housing, the housing consisting of:

- a cassette covering section extending to cover at least a part of the cassette when received inside the injector; and
- a distal section extending to cover the internal injector parts inside the housing before the cassette is secured inside the injector.

By cover the internal injector parts is meant to cover the internal injector parts along the longitudinally extending direction of the internal injector parts.

By having two sections, the auto injector can be constructed such that the cassette is interfacing with the auto injector at the proximal end of the internal injector parts with the cassette sharing the same longitudinal axis as the auto injector. This mitigates risk of the cassette getting stuck inside in the injector and also help to make the connection as slim as possible. Also, by the two-sectional construction where there is only a need for the cassette to positioned in the cassette covering section, user access to the internal parts inside the auto injector may be blocked. This also reduces impurities/dust from penetrating into the auto injector internal parts, in turn keeping the auto injector easily clean due to avoidance of grooves to e.g. collect dirt and dust etc. A more robust auto injector is thereby obtained. This prolongs the lifetime of the auto injector.

Disclosed herein in a third aspect is an auto injector adapted for receiving a cassette with medicament and for administering the medicament, wherein the auto injector comprises a housing extending from a proximal end to a distal end along a longitudinal direction, the housing comprising:

- a cassette covering section extending to cover the cassette when received inside the injector; and
- a distal section extending to cover all internal injector parts, wherein the auto injector comprises a cassette abutting surface adapted for abutting a distal end of the cassette when secured inside the auto injector, wherein the cassette abutting surface defines a proximal end plane from where substantially no internal injector parts extends proximally prior to assembling the cassette and the auto injector.

By cover the internal injector parts is meant to cover the internal injector parts along the longitudinally extending direction of the internal injector parts.

By substantially is included a situation where only a minor part of the internal injector parts protrude a small amount, such as up to 2%, 5%, or 10%, proximally compared to the cassette abutting surface. In some examples no parts protrude proximately.

By having cassette abutting surface from where substantially no internal injector parts extends proximally prior to assembling the cassette and the auto injector provides a smooth interior and cassette interface, which mitigates risk of the cassette getting stuck inside in the injector. Also, by the cassette abutting surface, user access to the internal parts inside the auto injector may be blocked. This also reduces impurities/dust from penetrating into the auto injector internal parts, in turn keeping the auto injector easily clean due to avoidance of grooves to e.g. collect dirt and dust etc. A more robust auto injector is thereby obtained. In turn, the lifetime of the auto injector is prolonged.

In one or more examples, the cassette abutting surface defines a proximal end plane from where substantially no cavities extends distally into the distal section.

In one or more examples, the housing encloses internal injector parts, the internal injector parts including at least a piston, a drive module adapted for moving the piston proximately, and a chassis, wherein the internal injector parts are defined by a proximal end plane and a distal end plane, and wherein the auto injector comprises noise reducing material at both the proximal end plane and the distal end plane of the internal parts.

Disclosed herein in a fourth aspect is an auto injector adapted for receiving a cassette with medicament and for administering the medicament, wherein the cassette is removable received in the auto injector, wherein the auto injector comprises a housing enclosing internal injector parts, the internal injector parts including at least a piston, a drive module adapted for moving the piston proximately, and a chassis, wherein the internal injector parts are defined by a proximal end plane and a distal end plane, and wherein the auto injector comprises noise reducing material, at both the proximal end plane and the distal end plane of the internal parts.

By the noise reducing material, the user experience is improved, as the sounds during use, which may concern a user, is reduced if not eliminated. A first noise reducing material may be positioned between the cassette and the internal injector parts, i.e. the proximal end plane, to damper noise created when auto injector parts move and come in contact with and/or act on cassette parts. The auto injector housing may also comprise a distal housing end plate against which a second noise reducing material is positioned. Thus, the second noise reducing material may be positioned between the distal end plane of the distal housing end plate. This dampers noise may by primarily distally moving parts in the auto injector and/or the cassette transferring force to the auto injector.

In one or more examples, the drive module is further adapted for moving the piston distally. Thus, the drive module may move the piston distally after end delivery of medicament to reset the auto injector making it ready for delivery of a new medicament dose when a new cassette is mounted in the auto injector.

In one or more examples, the noise reducing material, is one or more O-rings. Alternatively or complementary, the noise reducing material, is a soft material, such as rubber.

In one or more examples, the proximal end plane is extending in a direction perpendicular to the longitudinal direction of the auto injector.

In one or more examples, auto injector comprises one or more cassette interacting parts adapted for securing and fixating the cassette inside the auto injector and for facilitating administration of the medicament, wherein the one or more cassette interacting parts does not extend proximally from the proximal end plane prior to securing the cassette inside the injector.

In one or more examples, the one or more cassette interacting parts are adapted for moving in a proximal direction after a cassette has been positioned in the auto injector, whereby at least a part of one or more of the cassette interacting parts are extending proximally from the proximal end plane inside the auto injector.

In one or more examples, each of the cassette interacting parts are adapted for moving through the proximal end plane independently of another one of the cassette interacting parts.

In one or more examples, one or more cassette interacting parts includes a piston configured for proximal movement of a stopper comprised within the cassette, and one or more injector pins including:

a first cassette locking pin; and a skin sensor pin.

In one or more examples, one or more cassette interacting parts includes a cassette detection pin. The cassette detection pin may be substituted by other detection means such as a magnetic detection system, e.g. with magnets on cassette and auto injector surfaces coming in contact with each other and a corresponding Hall sensor inside the chassis. Alternatively, the cassette may have a pin, which comes in contact with a surface on the injector, whereby detection of the cassette is registered in the auto injector.

In one or more examples, the one or more injector pins further include a second cassette locking pin. The term 'first' and 'second' cassette locking pin is only meant to symbolise the presence of two pins. The pins may perform the same operation depending on the orientation of the cassette when inserted into the auto injector. Thus, both pins may e.g. function to lock the cassette into the auto injector, and/or to release cassette parts enabling delivery of medicament and/or for locking cassette parts relative to each other after delivery of medicament e.g. to prevent assess to an injection needle after delivery of medicament. If the auto injector is designed to allow insertion of a cassette only if it is orientated in a specific manner, fewer pins are needed. If the auto injector is designed to allow insertion of a cassette when orientated in a multiple manners compared to the auto injector, additional pins are normally needed. The pins may be arranged in a mirror image configuration allowing for insertion of the cassette when turning it 180 degrees around.

In one or more examples, the auto injector comprises a chassis with a proximal chassis part at a proximal end of the chassis. The proximal chassis part is normally perpendicular to the longitudinal direction of the auto injector. The proximal chassis part may be a plate having a circular shape, an elliptical shape, a square shape, a square shape with round corners, or similar. The proximal chassis part may be symmetrical around at least one mirror-image plane.

In one or more examples, the proximal chassis part comprises one or more openings adapted for allowing passage of an injector pin or the piston through each opening after or during securing of the cassette inside the auto injector. The proximal chassis part may further comprises an opening having a U-shape adapted for limiting movement of any cassette parts distally past the proximal end plane. By U-shaped is also included a U with sharp corners.

In one or more examples, one or more openings comprises:

a piston opening for allowing passage of the auto injector piston there through;

a first pin opening for allowing passage of the first cassette locking pin there through;

a third pin opening for allowing passage of the skin sensor pin of the auto injector there through.

In one or more examples, the one or more openings further comprises a second pin opening for allowing passage of a first cassette skin sensor pin comprised in the cassette.

The second pin opening may be a U-shaped opening with an end surface limiting the distal movement of the first cassette sensor pin and thereby the cassette skin sensor inside the auto injector.

In one or more examples, the one or more openings further comprises a fourth pin opening for allowing passage of the second cassette locking pin there through. As described above, the definition of 'first' and 'second' locking pin may depend and be defined by the orientation of the cassette, when the cassette is inserted into the au injector.

In one or more examples, the one or more openings further comprises a fifth opening for allowing passage of the cassette detection pin there through. The cassette detection pin may be substituted by an alternative cassette detection system and the need for the fifth opening eliminated.

In one or more examples, the auto injector comprises a drive module adapted for moving the piston in a proximal direction along the longitudinal axis. The drive module may further be adapted for moving the piston in a distal direction along the longitudinal axis In one or more examples, drive module is further configured for moving the first cassette locking pin, and/or the skin sensor pin, and/or the second cassette locking pin in the proximal direction along the longitudinal axis. Further, the first cassette locking pin and the second cassette locking pin may be locked to the piston such that the piston and the cassette locking pins move together along the longitudinal axis.

Disclosed herein in a sixth aspect is a system comprising a cassette with medicament and an auto injector for administering the medicament, wherein the cassette is removable received in the auto injector, wherein the auto injector comprises a housing extending from a proximal end to a distal end along a longitudinal axis, the housing comprising a cassette covering section covering the cassette when received inside the injector, the cassette covering section comprising at least one opening extending in the longitudinal direction of the housing;

wherein the cassette extends from a proximal end to a distal end along a longitudinal axis and comprising a cassette housing enclosing at least:

- a syringe compartment containing the medicament and adapted to be in connection with a needle for delivery of the medicament;
- a stopper movable from a distal position to a proximal position inside the syringe compartment for emptying the syringe compartment;

wherein the cassette housing comprises at least one opening extending along a longitudinal axis of the cassette housing; wherein the opening in the cassette housing and the opening in the cassette covering section are aligned when the cassette is positioned inside auto injector to facilitate inspection of the medicament in the syringe compartment.

By opening is also included an opening covered by a see-through material, i.e. a window type opening. The opening allows for easy inspection of the medicament. Further, the aligned openings allows for a user friendly assembly and guidance of the cassette into the auto injector.

In one or more examples, the cassette covering section and the cassette housing each comprise two openings, extending in the longitudinal direction on opposite sides of the housing and the cassette housing, respectively, wherein the openings, are aligned when the cassette is positioned inside auto injector to facilitate inspection of the medicament in the syringe compartment from two opposite directions. The openings may be formed as U-shaped openings extending into the housing. This allows a user to see through the entire device, thereby enabling more light to shine through the syringe compartment to provide a better view of possible miscolouring and possibly particulates in the drug contained within syringe compartment.

In one or more examples, the cassette covering section comprises interior guiding tracks in parallel with the longitudinal direction configured for guiding the cassette to a correct position when inserting the cassette into the cassette covering section. An easy guiding of the cassette inside the auto injector is ensuring correct positioning inside the injector.

In one or more examples, the cassette covering section comprises interior guiding tracks in parallel with the longitudinal direction.

In one or more examples, the interior guiding tracks forms part of the one or more openings inside the cassette covering section of auto injector housing.

The cassette receiving chassis, the piston, and the drive module are comprised inside the housing of the auto injector. The cassette is removable received in the auto injector.

Disclosed herein in a fifth aspect is a system comprising an auto injector according to any of the above aspects and a cassette comprising:

- a syringe compartment containing the medicament and extending from a proximal end to a distal end, wherein the proximal end is adapted for being in connection with a needle through which the medicament is allowed to exit the syringe compartment;
- a stopper movable from a distal position to a proximal position inside the syringe compartment by means of a piston in the auto injector moving the stopper proximally for emptying the syringe compartment; and
- a syringe holder extending around at least part of the syringe compartment.

The needle may be a hollow needle in fluid connection with the proximal end of the syringe compartment and connected to the syringe as part of the syringe. Alternatively, a luer lock needle may be connected to the syringe prior to injection of medicament. As yet a further alternative, a syringe system with a syringe terminated with a stopper at its distal end and a rubber septum at its proximal end, where a penetrating needle at a distal end pierces the septum when mounted onto the syringe while a proximal needle end penetrates into the patient skin.

In one or more examples, the cassette further comprises a hollow needle in fluid connection with the proximal end of the syringe compartment. Further, the cassette may comprise a rigid needle shield connected to the proximal end of the syringe compartment and adapted for covering a hollow needle. The hollow needle may be part of the cassette or be connected to the syringe in the cassette prior to medicament delivery. The latter may be the case if a luer lock or a needle system penetrating a septum in the syringe when connected to the cassette as described above.

In one or more examples, the cassette further comprises a cassette cap, and a cassette skin sensor. In one or more examples, the cassette cap comprises a first part positioned between the rigid needle shield and the proximal end of the syringe compartment. The first part could alternatively have a 'hook' with sharp edges, which carve into the side of the rigid needle shield instead of at the distal end of it. Other alternatives may also be possible.

The cassette may thus comprise:

- a syringe compartment containing the medicament and extending from a proximal end to a distal end;
- a hollow needle in fluid connection with the proximal end of the syringe compartment;

a rigid needle shield connected to the proximal end of the syringe compartment and covering the hollow needle;
a stopper movable from a distal position to a proximal position inside the syringe compartment by means of the piston moving the stopper proximally for emptying the syringe compartment;
a syringe holder extending around at least part of the syringe compartment;
a cassette cap having a first part positioned between the rigid needle shield and the proximal end of the syringe compartment, and
a cassette skin sensor.

In one or more examples, the syringe compartment, the hollow needle and the stopper is part of a syringe. The syringe may be fixed inside the syringe holder, at a distal end of the syringe.

In one or more examples, the cassette is interfacing with the auto injector at the distal end of the cassette sharing the same longitudinal axis. This mitigates risk of the cassette getting stuck inside in the injector and also help to make the connection as slim as possible.

In one or more examples, the cassette is adapted for being received in the auto injector by movement of the cassette and the auto injector towards each other along a shared longitudinal axis without significant rotation of the cassette around the shared longitudinal axis.

In one or more examples, when the drive module moves the first cassette locking pin proximally, the cassette is locked in auto injector. The second cassette locking pin may in addition or alternatively lock the cassette in the auto injector by proximal movement of the second cassette locking pin. The cassette locking pins may move simultaneously or individually. The cassette locking pins may also move together with the piston by e.g. locking/connecting the three pins together.

In one or more examples, when the drive module moves the first cassette locking pin further in the proximal direction, the cassette skin sensor is adapted for being distally unlocked from the syringe holder allowing for distal movement of the cassette skin sensor. The second cassette locking pin may in addition or alternatively unlock the syringe holder by further proximal movement of the second cassette locking pin. The cassette locking pins may move simultaneously or individually. The cassette locking pins may also move together with the piston by e.g. locking/connecting the three pins together. Thus, when the drive module moves the second cassette locking pin further in the proximal direction, the cassette skin sensor may be adapted for being proximally unlocked from the syringe holder allowing for proximal movement of the cassette skin sensor relative to the syringe holder.

In one or more examples, when the drive module moves the piston proximally, the second cassette locking pin is adapted for also unlocking for movement of the cassette skin sensor.

In one or more examples, the system according further comprising a skin sensor spring system adapted for pushing the skin sensor pin of auto injector against a second cassette skin sensor pin at least after release of the cassette skin sensor from the syringe holder by movement of the first cassette locking pin and/or the second cassette locking pin in a proximal direction.

In one or more examples, the skin sensor spring system is adapted for pushing the cassette skin sensor in a proximal direction into a locked position preventing movement of the cassette skin sensor in a distal direction. This ensures that the needle is not exposed after end delivery of medicament. The cassette skin sensor may be pushed into a locked position preventing distal movement of the cassette skin sensor. The distal locking may be facilitated by a cassette skin sensor arm, where a locking surface of the cassette skin sensor arm locks into an inner opening in the cassette housing. Proximal movement of the cassette skin sensor may also be prevented, e.g. by an additional set of housing-skin sensor surfaces.

In one or more examples, the syringe holder comprises a syringe holder support tube, which supports the syringe compartment.

In one or more examples, the cassette skin sensor covers at least part of the syringe holder, such as the majority of the syringe holder.

In one or more examples, the cassette skin sensor comprises at least a first skin sensor pin and/or a second skin sensor pin extending from the distal end of the cassette skin sensor.

In one or more examples, the syringe holder comprises one or more openings selected from the group of:
a first pin opening for allowing passage of a first cassette locking pin of the auto injector there through;
a second pin opening for allowing passage of the first cassette skin sensor pin;
a third pin opening for allowing passage of a skin sensor pin of the auto injector, and/or the second cassette skin sensor pin there through;
a fourth pin opening for allowing passage of a second cassette locking pin of the auto injector there through;
a piston opening for allowing passage of the auto injector piston there through.

In one or more examples, the syringe holder comprises a syringe holder plate, wherein the piston opening and/or one or more of the pin openings are positioned in the syringe holder plate.

In one or more examples, the syringe holder comprises a first syringe holder arm extending in a proximal direction from the syringe holder plate.

In one or more examples, the first syringe holder arm comprises a proximal surface, and wherein the cassette skin sensor comprises a first locking protrusion engaging with the proximal surface, wherein the engagement of the first locking protrusion and the proximal surface prevents movement of the cassette skin sensor towards the syringe holder.

In one or more examples, the first syringe holder arm is flexibly connected to the syringe holder plate.

In one or more examples, the first syringe holder arm is deflectable by proximal movement of the first cassette locking pin of the auto injector through the first pin opening in the syringe holder, wherein the deflection of the first syringe holder arm releases the cassette skin sensor allowing it to move towards the syringe holder.

In one or more examples, upon movement of the cassette skin sensor towards the syringe holder:
the first cassette skin sensor pin is brought into/extends through the second pin opening in the syringe holder, and
the second cassette skin sensor pin is brought into/extends through the third pin opening in the syringe holder.

In one or more examples, the syringe holder comprises a second syringe holder arm extending in a proximal direction from the syringe holder plate.

In one or more examples, the second syringe holder arm comprises a distal surface, and wherein the cassette skin sensor comprises a second locking protrusion against which the distal surface is resting, wherein the engagement of the second locking protrusion and the distal surface prevents movement of the cassette skin sensor away from the syringe holder.

In one or more examples, the second syringe holder arm is flexibly connected to the syringe holder plate.

In one or more examples, the second syringe holder arm is deflectable by proximal movement of the second cassette locking pin of the auto injector through the fourth pin opening in the syringe holder, wherein the deflection of the second syringe holder arm allows the cassette skin sensor it to move away from the syringe holder.

In one or more examples, the syringe holder further comprises one or more syringe locking protrusions locking the syringe in the cassette.

In one or more examples, the syringe holder and thereby the cassette is locked to the auto injector housing when the cassette is positioned in the auto injector.

In one or more examples, the syringe holder and the skin sensor are longitudinally movable relative to each other upon release of the skin sensor from the syringe holder.

In one or more examples, the cassette further comprises a cassette housing extending from a proximal to a distal end, the cassette housing enclosing at least the syringe holder and the cassette skin sensor.

In one or more examples, the cassette housing comprises one or more locking openings at the distal end into which the one or more syringe holder locking protrusions on the syringe holder locks syringe holder to the cassette housing.

In one or more examples, the cassette housing comprises one or more internal protruding rails inside the cassette housing for guiding the skin sensor inside the cassette housing.

In one or more examples, the cassette housing comprises a distal end surface with a skin sensor housing opening through which the cassette skin sensor extends.

In one or more examples, the cassette housing is oval.

In one or more examples, the cassette cap comprises an inner rigid needle shield tube with the first part and an outer an outer rigid needle shield tube, wherein:

- the outer rigid needle shield tube surrounds the inner rigid needle shield tube, and
- the inner rigid needle shield tube surrounds the rigid needle shield.

In one or more examples, the outer rigid needle shield tube abuts the distal end surface of the cassette housing, and wherein the proximal end of the cassette skin sensor is positioned between the inner rigid needle shield tube and the outer rigid needle shield tube.

In one or more examples, the cassette cap is removable from the syringe compartment, and wherein when the cassette cap is removed, the rigid needle shield follows with it, whereby the hollow needle is exposed.

In one or more examples, the cassette cap is an elongated tube positioned between the syringe and the cassette skin sensor.

In one or more examples, the cassette cap comprises at least one holder pin extending from a distal end of the cassette cap.

In one or more examples upon proximal movement of a cassette cap pin in the auto injector abutting the at least one holder pin, the cassette cap and thereby also the rigid needle shield is pushed proximally for release of the rigid needle shield.

In one or more examples, the cassette covering section comprises at least one opening extending in the longitudinal direction of the housing, wherein the cassette housing comprises at least one opening extending along a longitudinal axis of the cassette housing, wherein the at least one opening in the cassette housing and the at least one opening in the cassette covering section are aligned when the cassette is positioned inside auto injector to facilitate inspection of the medicament in the syringe compartment. By opening is also included an opening covered by a see-through material, i.e. a window type opening.

In one or more examples, the cassette covering section and the cassette housing each comprise two openings, extending in the longitudinal direction on opposite sides of the housing and the cassette housing, respectively, wherein the openings, are aligned when the cassette is positioned inside auto injector to facilitate inspection of the medicament in the syringe compartment from two opposite directions. The openings may be formed as U-shaped openings extending into the housing. This allows a user to see through the entire device, thereby enabling more light to shine through the syringe compartment to provide a better view of possible miscolouring and possibly particulates in the drug contained within syringe compartment.

In one or more examples, the cassette and auto injector housing have cross sectional planes perpendicular to the longitudinal axis of the cassette housing and the auto injector housing, wherein the cross sectional planes are non-circular in shape, such as oval or square in shape. By cross sectional planes are meant planes perpendicular to the longitudinal axis. The oval shape includes cross-sectional planes where two perpendicular radius differs by at least 10% such as 20% such as 30%. Max 50%

In one or more examples, the cassette covering section comprises interior guiding tracks in parallel with the longitudinal direction configured for guiding the cassette to a correct position when inserting the cassette into the cassette covering section. Easy guiding of the cassette inside auto injector ensuring correct positioning inside the injector.

In one or more examples, the interior guiding tracks forms part of the openings inside the cassette covering section of auto injector housing.

In one or more examples, the cassette receiving chassis is a cassette receiving chassis extending from a proximal end to a distal end, wherein the proximal end of the chassis comprises a proximal chassis part with one or more openings selected from the group of:

- a piston opening for allowing passage of the auto injector piston there through;
- a first pin opening for allowing passage of the first cassette locking pin there through;
- a second pin opening for allowing passage of the first cassette skin sensor pin;
- a third pin opening for allowing passage of:
  - the skin sensor pin of the auto injector, and/or
  - the second cassette skin sensor pin there through;
- a fourth pin opening for allowing passage of the second cassette locking pin there through;
- a fifth opening for allowing passage of the cassette detection pin there through.

In one or more examples, the second pin opening is a well-shaped opening with an end surface limiting the distal movement of the first cassette sensor pin and thereby the cassette skin sensor inside the auto injector.

In one or more examples, drive module is further configured for moving the first cassette locking pin, the skin sensor pin, the second cassette locking pin, and the cassette detection pin proximally.

In one or more examples, when the drive module moves the first cassette locking pin proximally, the cassette skin sensor is distally unlocked from the syringe holder allowing for distal movement of the cassette skin sensor, wherein the unlocking of the cassette skin sensor locks the cassette in the auto injector.

In one or more examples, when the drive module moves the piston proximally for delivery of medicament, the second cassette locking pin is also unlocked for movement of the cassette skin sensor proximally after delivery of medicament and/or removal of the auto injector from the patient's skin.

In one or more examples, the auto injector further comprising a skin sensor spring system pushing the skin sensor pin of the auto injector against the second cassette skin sensor pin at least after release of the cassette skin sensor from the syringe holder by proximal movement of the first cassette locking pin and the second cassette locking pin.

In one or more examples, the skin sensor spring system pushes the cassette skin sensor proximally in a locked position preventing distal movement of the cassette skin sensor.

In one or more examples, the housing is in one piece with a proximal opening for receiving the cassette.

Disclosed herein in a seventh aspect is a method for assembling a cassette for use in an auto injector, the method comprising:

- assembling an outer cassette part comprising a cassette housing and a cassette cap by connecting a proximal end of the cassette housing to a distal end of the cassette cap;
- inserting a proximal end of an inner cassette part into a distal end of the outer cassette part and pushing the inner cassette part into the outer cassette part such that the majority of the inner cassette part is covered by the outer cassette part.

The method allows for very easy assembly of the cassette, which may be unscaled and atomized. Also, the method allows for assembly of the cassette at one location from where the cassette can be shipped to a different location for a subsequent step of inserting a syringe into the cassette. This allows the cassette to be used with a variety of syringes containing different medicament.

In one or more examples, the inner cassette part comprises a comprising a syringe holder. In one or more examples, the method is further comprising assembling the inner cassette part comprising the syringe holder and a cassette skin sensor by inserting a proximal end of the syringe holder into a distal end of the cassette skin sensor and pushing the syringe holder into the cassette skin sensor such that a part of the syringe holder is covered by the cassette skin sensor. Assembling of the outer cassette part and inner cassette part may be performed simultaneously or in random order.

In one or more examples, the part of the syringe holder covered by the cassette skin sensor constitutes at least 10%, such as at least 20%, such as at least 30%, such as at least 40%, such as at least 50%.

In one or more examples, the cassette cap is extending from the distal end to a proximal end along a longitudinal axis, wherein the method further comprises positioning the cassette cap in a first mount with the longitudinal axis positioned in an upwards direction such that the distal end is positioned above the proximal end prior to the assembling of the outer cassette part.

In one or more examples, the cassette cap is maintained positioned in the position in the first mount while assembling the outer cassette part.

In one or more examples, the cassette skin sensor is extending from the distal end to a proximal end along a longitudinal axis, wherein the method further comprises comprising positioning the cassette skin sensor in a second mount with the distal end in an upwards direction such that the distal end is positioned above the proximal end prior to the assembling of the inner cassette part.

In one or more examples, the cassette skin sensor is maintained positioned in the second mount while assembling the inner cassette part.

In one or more examples, the inner cassette part is inserted into the outer cassette part while the outer cassette part is positioned in the first mount. The first and second mount may be an integrate mount or separate mounts. The first mount may e.g. by a first part of a mount and the second mount a second part of the same mount. By using mounts, a large batch of parts can be assembled at once.

The cassette housing may be extending from a distal end to the proximal end along a longitudinal axis. The method may also include positioning the cassette housing in an upwards direction such that the proximal end is positioned above the distal end prior to the assembling of the outer cassette part, and flipping the cassette housing around to have the distal end point in the upwards for assembling of the cassette housing and the cassette cap.

In one or more examples, the syringe holder comprises one or more syringe locking protrusions, wherein the method further comprises fixating a syringe inside the inner cassette part by inserting a proximal end of the syringe into the distal end of the inner cassette part, pushing the syringe into the inner cassette part, and moving the one or more syringe locking protrusions to lock the syringe inside the inner cassette. If the cassette housing is without the cassette locking protrusions, the syringe may be fixed in the syringe holder be frictional force.

In one or more examples, syringe extends from a proximal end to a distal end and comprises:

- a syringe compartment containing medicament, and extending from a proximal end to a distal end, wherein the proximal end is adapted for being in connection with a needle through which the medicament is allowed to exit the syringe compartment;
- a stopper adapted for being moved from a distal position to a proximal position inside the syringe compartment.

The needle may be a hollow needle in fluid connection with the proximal end of the syringe compartment and connected to the syringe as part of the syringe. Alternatively, a luer lock needle may be connected to the syringe prior to injection of medicament. As yet a further alternative, a syringe system with a cartridge terminated with a stopper at its distal end and a rubber septum at its proximal end, where a penetrating needle at a distal end pierces the septum when mounted onto the cartridge while a proximal needle end penetrates into the patient skin.

In one or more examples, the syringe further comprises a hollow needle in fluid connection with the proximal end of the syringe compartment. The syringe may also comprise a rigid needle shield connected to the proximal end of the syringe compartment and adapted for covering the hollow needle. The hollow needle may be part of the cassette or be connected to the syringe in the cassette prior to medicament delivery. The latter may be the case if a luer lock or a needle system penetrating a septum in the syringe when connected to the cassette as described above.

The syringe may in this example for example be a 2.25 ml syringe.

In one or more examples, the method further comprises inserting a proximal end of a cassette sleeve into the distal end of the syringe holder and pushing the cassette sleeve into the syringe holder such that the majority of the cassette sleeve is covered by the syringe holder prior to or directly after inserting the syringe holder into the cassette skin sensor, the cassette sleeve thereby constituting a part of the inner cassette part.

In one or more examples, the cassette sleeve comprises proximal extending deflectable sleeve arms.

In one or more examples, the syringe comprises the hollow needle, and a rigid needle shield, wherein the deflectable sleeve arms deflects into openings in the syringe holder and cassette skin sensor when the syringe is inserted into the inner cassette part allowing the rigid needle shield to pass the deflectable sleeve arms.

In one or more examples, the deflectable sleeve arms relax into a position between the rigid needle shield and the syringe compartment after the rigid needle shield has passed the deflectable sleeve arms.

In one or more examples, after the deflectable sleeve arms has relaxed into a position between the rigid needle shield and the syringe compartment, and the syringe is pushed further proximally before locking it to the cassette, the cassette sleeve rotates into a position from where the sleeve arms cannot deflect. The cassette sleeve may comprises at least one sleeve locking protrusion coming in contact with at least one inner helical surface part inside the syringe holder when the syringe is pushed proximally. The helical shape of the at least one inner helical surface part forces the cassette sleeve to rotate. The rotation may be between 70-110 degrees, such as 80-100 degrees, such as 85-95 degrees, such as approximately 90 degrees.

In one or more examples, the rotation of the cassette sleeve rotates it into a position allowing a viewer to view the medicament inside the syringe.

In one or more examples, the syringe is inserted in the inner cassette part while the outer cassette part assembled with the inner cassette part is positioned in the first mount.

The cassette cap may comprise a first part positioned between the rigid needle shield and the proximal end of the syringe compartment when the syringe is positioned inside the inner cassette part, and an inner rigid needle shield tube with the first part and an outer rigid needle shield tube, wherein the outer rigid needle shield tube surrounds the inner rigid needle shield tube, and the inner rigid needle shield tube surrounds the rigid needle shield.

The first part of the cassette cap may extend inside the cassette housing opening when the outer cassette part is assembled.

Any of the above features described in conjunction with a particular aspect/example is not limited to that aspect/example and can be practiced in any other examples even if not so illustrated, or if not so explicitly described.

BRIEF DESCRIPTION OF THE DRAWINGS

Various examples are described hereinafter with reference to the figures. Like reference numerals refer to like elements throughout. Like elements will, thus, not be described in detail with respect to the description of each figure. It should also be noted that the figures are only intended to facilitate the description of the examples. They are not intended as an exhaustive description of the claimed invention or as a limitation on the scope of the claimed invention. In addition, an illustrated example needs not have all the aspects or advantages shown. An aspect or an advantage described in conjunction with a particular example is not necessarily limited to that example and can be practiced in any other examples even if not so illustrated, or if not so explicitly described.

in FIGS. 1-2, where the auto injector is shown in an exploded view.

FIG. 8A-B show an assembly of an outer cassette part.

FIG. 9A-C show an assembly of an inner cassette part.

FIGS. 14A-E show the assembling of a syringe into a cassette having a cassette sleeve as shown in FIGS. 12A-B included.

in FIGS. 1-2 or FIGS. 8-15, where the auto injector is shown in an exploded view.

DESCRIPTION OF DRAWINGS

Figure 1A:
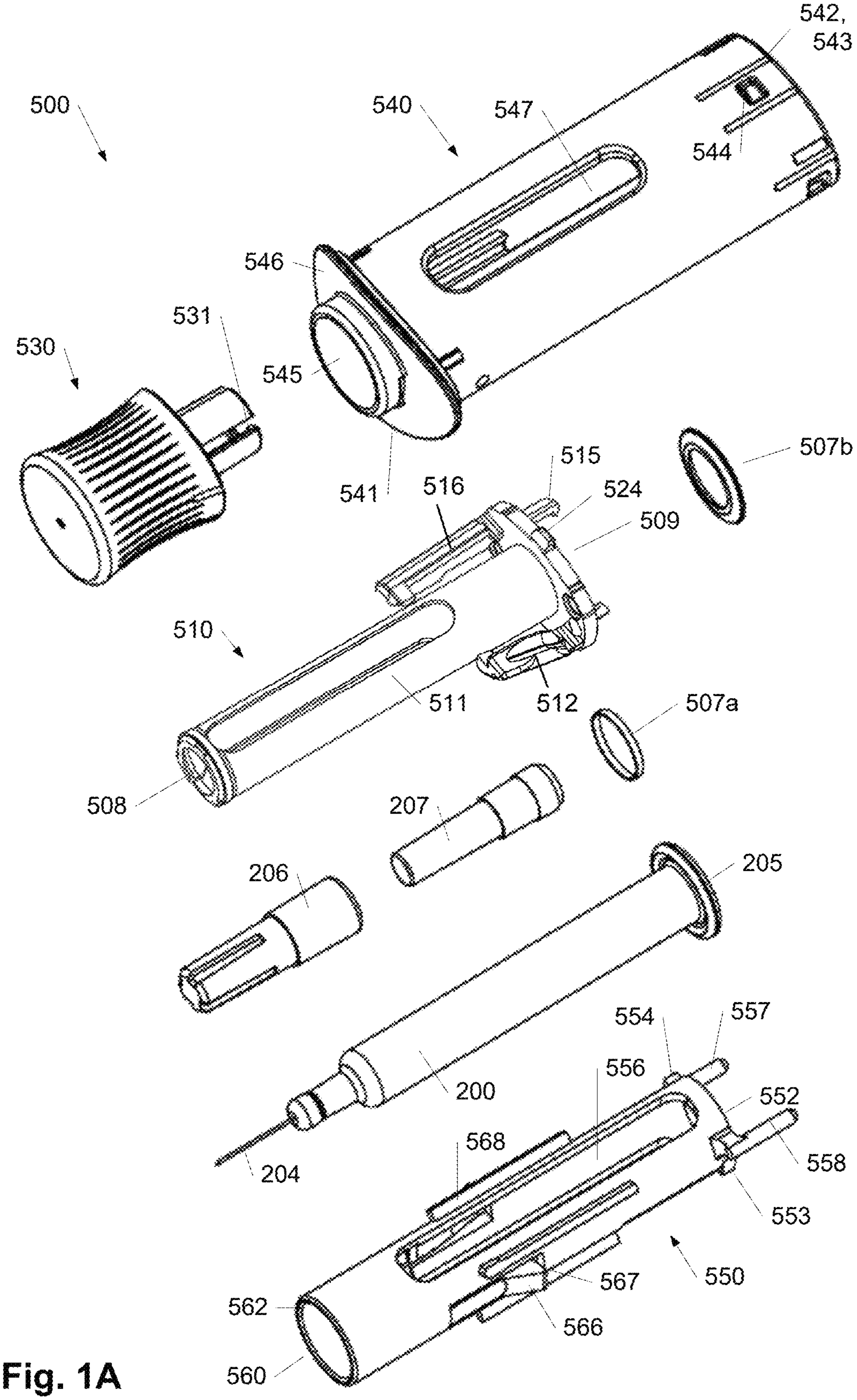
FIG. 1A shows an example of a cassette in an exploded view.

Exemplary examples will now be described more fully hereinafter with reference to the accompanying drawings. In this regard, the present examples may have different forms and should not be construed as being limited to the descriptions set forth herein. Accordingly, the examples are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

In the drawings, thicknesses of a plurality of layers and areas are illustrated in an enlarged manner for clarity and ease of description thereof. When a layer, area, element, or plate is referred to as being "on" another layer, area, element, or plate, it may be directly on the other layer, area, element, or plate, or intervening layers, areas, elements, or plates may be present therebetween. Conversely, when a layer, area, element, or plate is referred to as being "directly on" another layer, area, element, or plate, there are no intervening layers, areas, elements, or plates therebetween. Further when a layer, area, element, or plate is referred to as being "below" another layer, area, element, or plate, it may be directly below the other layer, area, element, or plate, or intervening layers, areas, elements, or plates may be present therebetween. Conversely, when a layer, area, element, or plate is referred to as being "directly below" another layer, area, element, or plate, there are no intervening layers, areas, elements, or plates therebetween.

The spatially relative terms "lower" or "bottom" and "upper" or "top", "below", "beneath", "less", "above", and the like, may be used herein for ease of description to describe the relationship between one element or component and another element or component as illustrated in the drawings. It will be understood that the spatially relative terms are intended to encompass different orientations of the device in use or operation, in addition to the orientation depicted in the drawings. For example, in the case where a device illustrated in the drawings is turned over, elements described as being on the "lower" side of other elements, or "below" or "beneath" another element would then be oriented on "upper" sides of the other elements, or "above" another element. Accordingly, the illustrative term "below" or "beneath" may include both the "lower" and "upper" orientation positions, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below, and thus the spatially relative terms may be interpreted differently depending on the orientations described.

Throughout the specification, when an element is referred to as being "connected" to another element, the element is "directly connected" to the other element, or "electrically connected" to the other element with one or more intervening elements interposed therebetween.

The terminology used herein is for the purpose of describing particular examples only and is not intended to be limiting. As used herein, the singular forms "a," "an," and "the" are intended to include the plural forms, including "at least one," unless the content clearly indicates otherwise. "At least one" is not to be construed as limiting "a" or "an." It will be further understood that the terms "comprises," "comprising," "includes" and/or "including," when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," and the like may be used herein to describe various elements, these elements should not be limited by these terms. These terms are only used to distinguish one element from another element. Thus, "a first element" discussed below could be termed "a second element" or "a third element," and "a second element" and "a third element" may be termed likewise without departing from the teachings herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" may mean within one or more standard deviations, or within ±30%, 20%, 10%, 5% of the stated value.

Unless otherwise defined, all terms used herein (including technical and scientific terms) have the same meaning as commonly understood by those skilled in the art to which this invention pertains. It will be further understood that terms, such as those defined in commonly used dictionaries, should be interpreted as having a meaning that is consistent with their meaning in the context of the relevant art and will not be interpreted in an idealized or overly formal sense unless expressly so defined in the present specification.

Exemplary examples are described herein with reference to cross section illustrations that are schematic illustrations of idealized examples, wherein like reference numerals refer to like elements throughout the specification. As such, variations from the shapes of the illustrations as a result, for example, of manufacturing techniques and/or tolerances, are to be expected. Thus, examples described herein should not be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. Some of the parts which are not associated with the description may not be provided in order to specifically describe exemplary examples of the present disclosure.

All references to the proximal direction or proximal surfaces refer to parts, surfaces and similar oriented in the direction of insertion, i.e. in the direction of the insertion needle and the outer part of the auto injector touching the skin during injection of the medicament.

Likewise, all references to the distal direction or distal surfaces refer to parts, surfaces and similar oriented in the direction away from the direction of the insertion needle, i.e. in the direction of the user.

Figure 3:
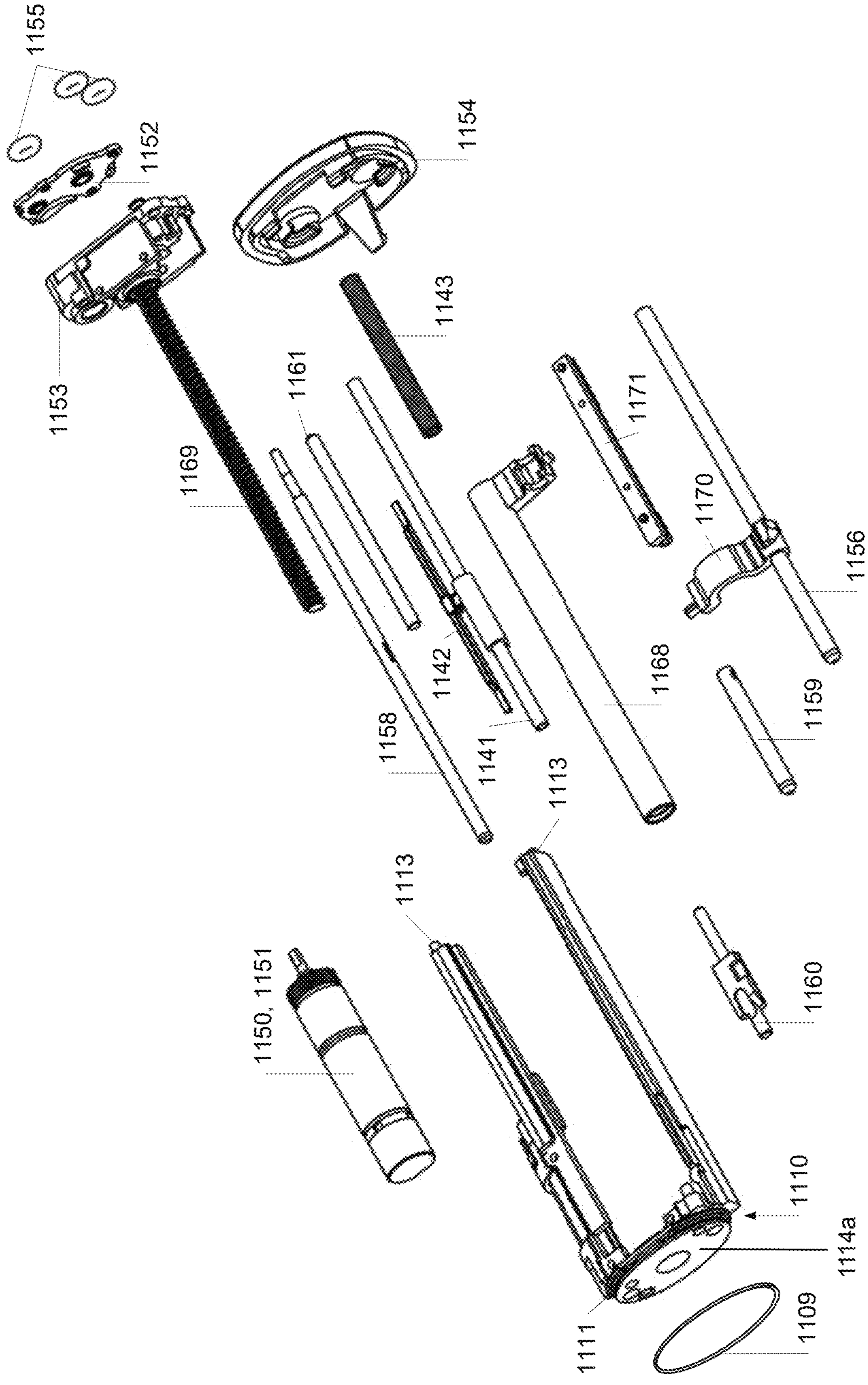
FIG. 3 shows an example of an auto injector for receiving a cassette as shown e.g.

FIG. 1A shows an example of a cassette 500 in an exploded view. An auto injector 1000 for receiving the cassette 500 is shown in FIGS. 3-5. The cassette comprises a syringe 200 with a syringe compartment 202 containing the medicament, a hollow needle 204 in fluid connection with the syringe compartment, a rigid needle shield 206 connected to the proximal end of the syringe compartment and covering the hollow needle, and a stopper 208 movable from a distal position to a proximal position inside the syringe compartment 202 by means of a piston in the auto injector.

The needle shield 206 shown in FIG. 1A has both an outer part 206, and an inner part 207. The parts may normally be a connected or even produced as a one-piece item.

Positioned around the syringe 200 is a syringe holder 510 extending around at least part of the syringe compartment 202. The syringe holder 510 (see further details in FIGS. 1B-C) has a syringe holder support tube 511, which supports the syringe compartment 202. The tube 511 has an opening for inspection of the medicament in the syringe compartment 202. The syringe 200 is fixed inside the syringe holder 510 at the distal end 205 of the syringe 200, which has a collar-like shape. Syringe holder rings 507*a*, 507*b* may be used for further securing the syringe 200 inside the syringe holder 510. These may also be omitted.

The cassette 500 comprises a cassette housing 540 extending from a proximal 541 to a distal end 542. The cassette housing 540 is oval, which helps ensure an accurate positioning of the cassette 500 inside the auto injector 1000. The oval shape may also make the cassette more compact. Alternative shapes such as square shape may also be imagined.

The cassette housing 540 is enclosing a cassette skin sensor 550. At the proximal end 541 of the cassette housing 540 is a housing shoulder 546 with an opening 545 through which the cassette skin sensor 540 can extend. The cassette housing 540 have internal protruding rails 548 (not shown in the figure) on its inside for guiding the skin sensor 550. The two parts 540, 550 are movable in relation to each other in an unlocked configuration. The cassette skin sensor 550 is positioned such that it extends proximally from the cassette housing 540.

The cassette housing 540 has a distal end surface 543 with a skin sensor housing opening 545 through which the cassette skin sensor 550 extends. This is most clearly seen in the cut-through images, e.g. in FIG. 2. The cassette housing 540 has an opening 547 in the longitudinal direction for inspection of the medicament in the cassette 500.

The cassette skin sensor 550 has two pins; a first skin sensor pin 557 and a second skin sensor pin 558, extending from the distal end 552 of the cassette skin sensor 550.

Figure 1B:
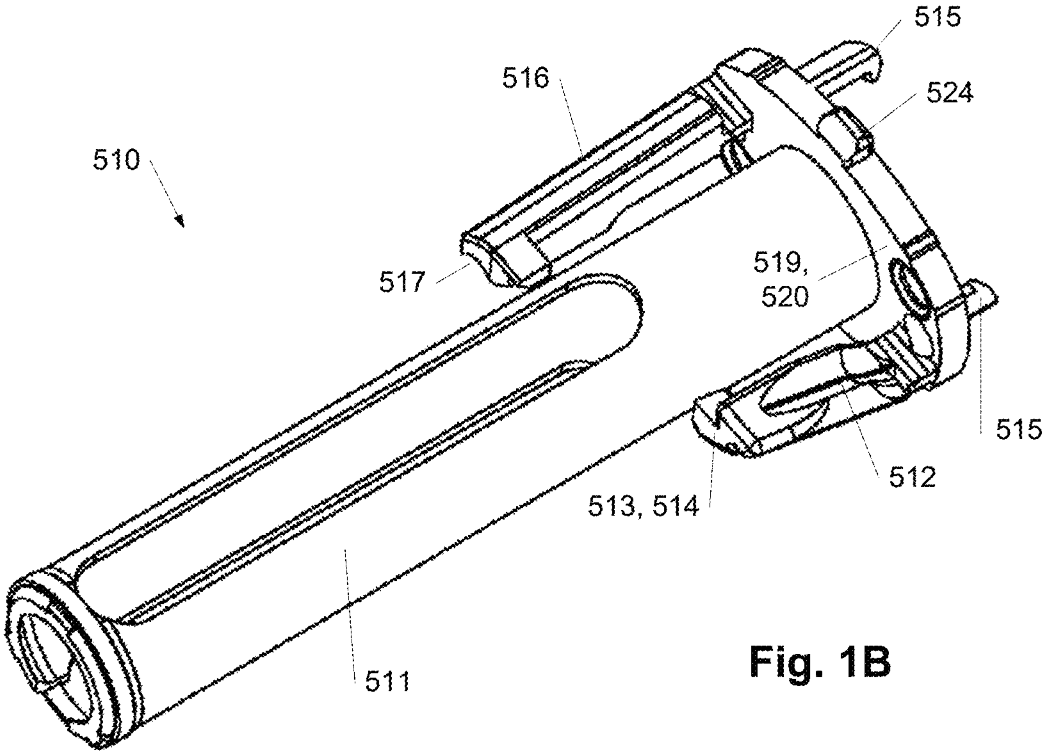
FIGS. 1B-C show a close-up of a syringe holder in the cassette in FIG. 1A seen from two different directions.
Figure 1C:
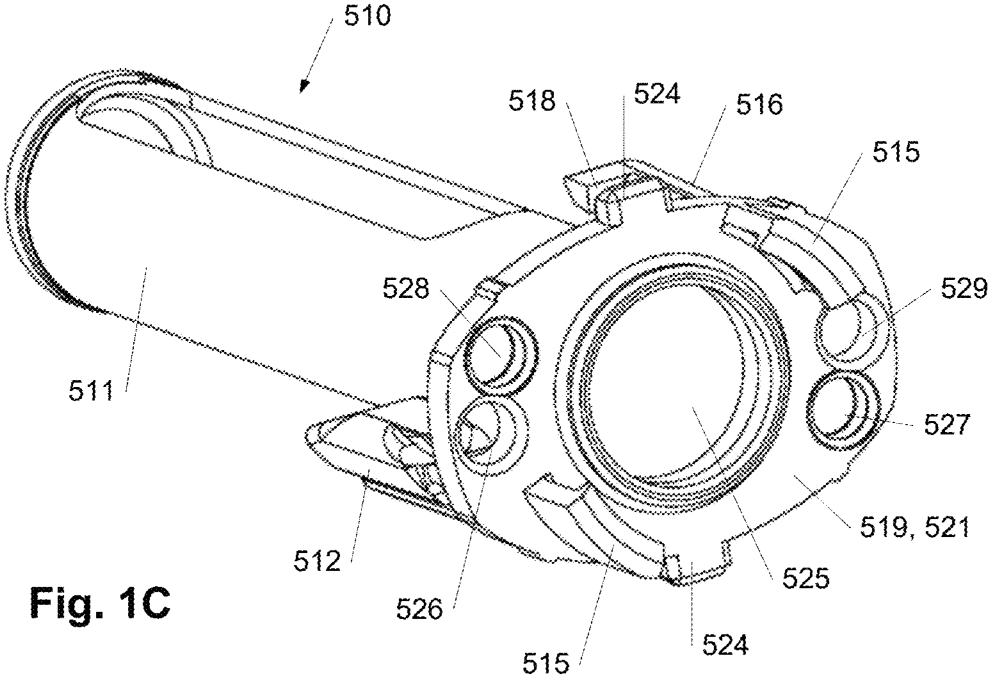

The cassette skin sensor 550 covers at least part if not the majority of a syringe holder 510, which is shown in more details in FIGS. 1B-C in a front-end and a rear-end perspective view. The syringe holder 510 has an elongated tubular part 511 with an opening for inspection of the medicament. At the distal end 509 of the syringe holder 510 is a syringe holder plate 519, which has a number of openings including: a first pin opening 526, a second pin opening 527, a third pin opening 528, a fourth pin opening 529, and a piston opening 525. It is through the piston opening 525 that the auto injector piston 1168 extends when medicament is delivered to the patient. The openings are normally circular, but may also have different shapes mimicking the shape of the pins extending there through. The openings may be positioned at the peripheral edge of the syringe holder plate 519 such that only part of the circular opening extends into the syringe holder plate 519. This is shown in the example in FIGS. 11C-D.

The syringe holder 510 also comprises a first syringe holder arm 512 extending in a proximal direction from the syringe holder plate 519. The first syringe holder arm 512 has a proximal surface 514 at the proximal end of the arm 512. When the cassette skin sensor 550 and the syringe holder 510 are in a first position, a first locking protrusion 553 on the cassette skin sensor 550 engages with the proximal surface 514. This engagement of the first locking protrusion 553 and the proximal surface 514 prevents movement of the cassette skin sensor 550 towards the syringe holder 510. The first syringe holder arm 512 is flexibly connected to the syringe holder plate 519.

The syringe holder 510 may also comprise a syringe holder ring 507*a*, which locks the syringe 200 inside the syringe holder 510.

When the cassette 500 is positioned in the auto injector 1000, the first pin opening 526 allows for passage of a first cassette locking pin 1156 of the auto injector 1000 there through. This is seen and described in connection with e.g. FIGS. 7A-F. When the first cassette locking pin 1156 of the auto injector 1000 passes through the first pin opening 526 in the syringe holder 510, it comes in contact with the first syringe holder arm 512 and deflects it. This causes a release of the cassette skin sensor 550 allowing it to move towards the syringe holder 510, i.e. a distal direction movement of the cassette skin sensor 550. Upon movement of the cassette skin sensor 550 towards the syringe holder 510, the first cassette skin sensor pin 557 moves towards—and possibly through—the second pin opening 527 in the syringe holder 510. Similarly, the second cassette skin sensor pin 558 moves towards—and possibly through—the third pin opening 528 in the syringe holder 510 when the cassette skin sensor 558 moves distally.

The syringe holder 510 and the skin sensor 550 are longitudinally movable relative to each other upon release of the skin sensor 550 from the syringe holder 510.

Figure 7A:
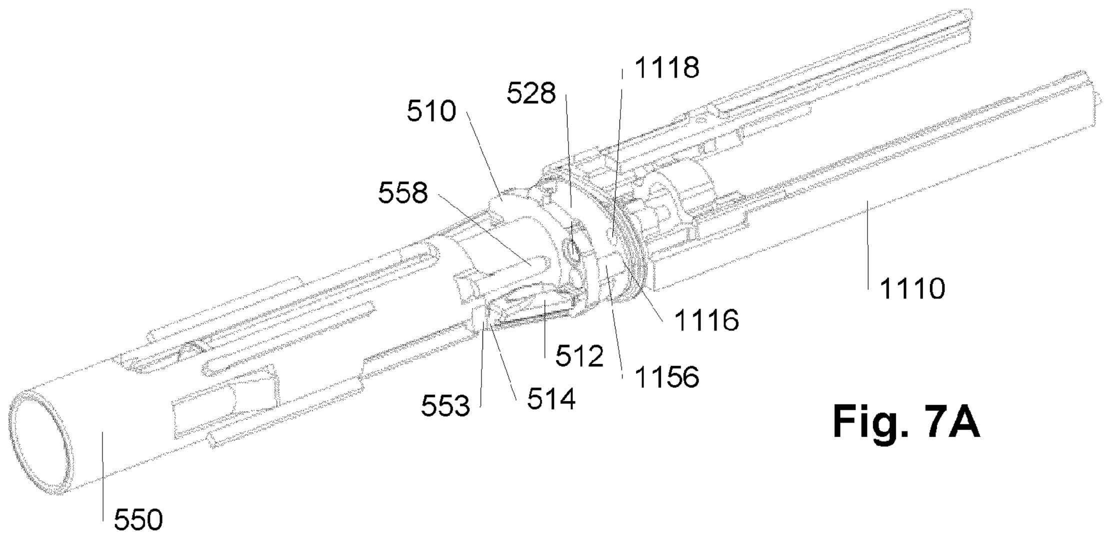
FIGS. 7A-C show the steps in releasing the cassette skin sensor from the syringe holder in the cassette of FIGS. 1-2 by means of the auto injector of FIGS. 3-5, FIGS. 7D-F show the locking of the cassette skin sensor in a proximal position after delivery of medicament.
Figure 7B:
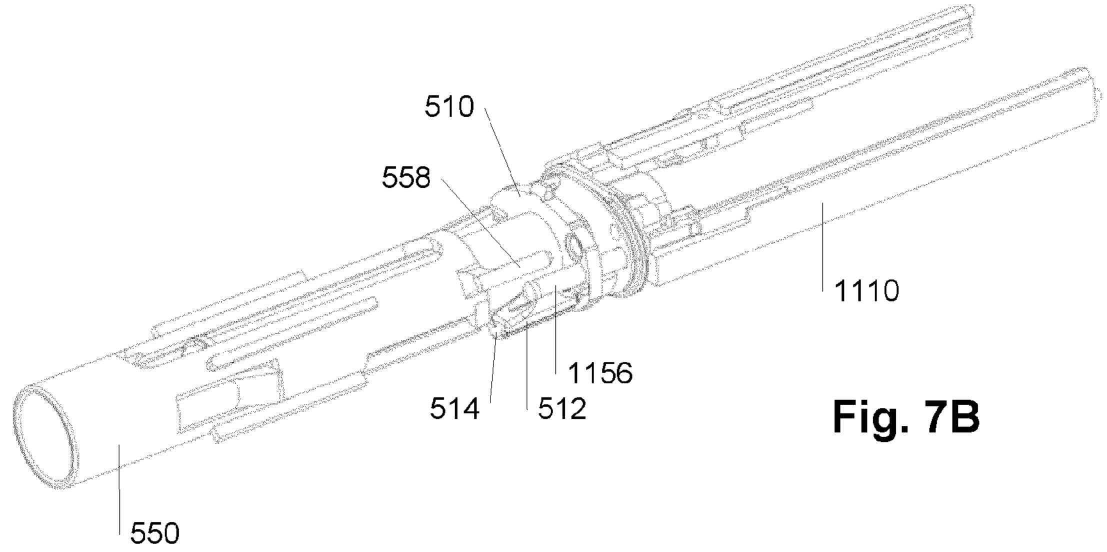
Figure 7C:
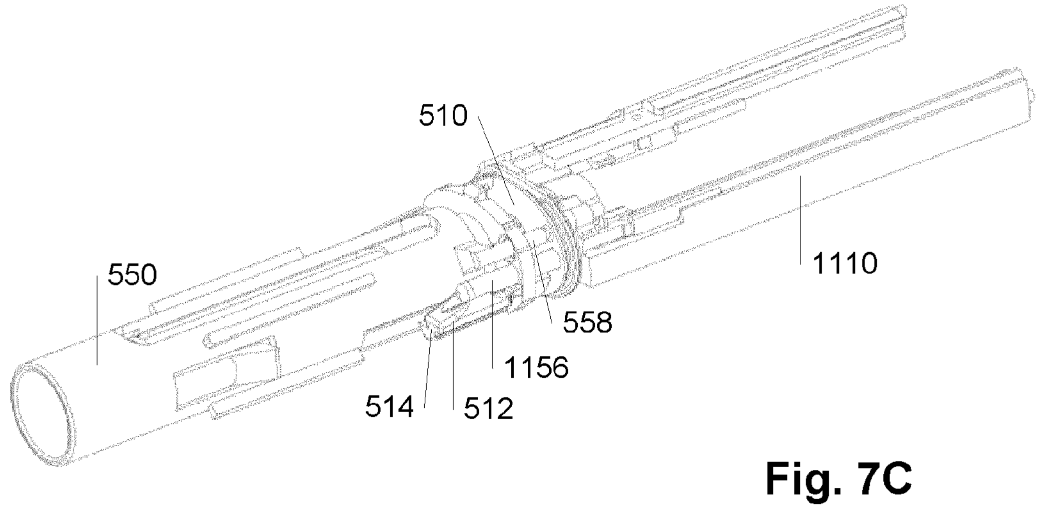
Figure 7D:
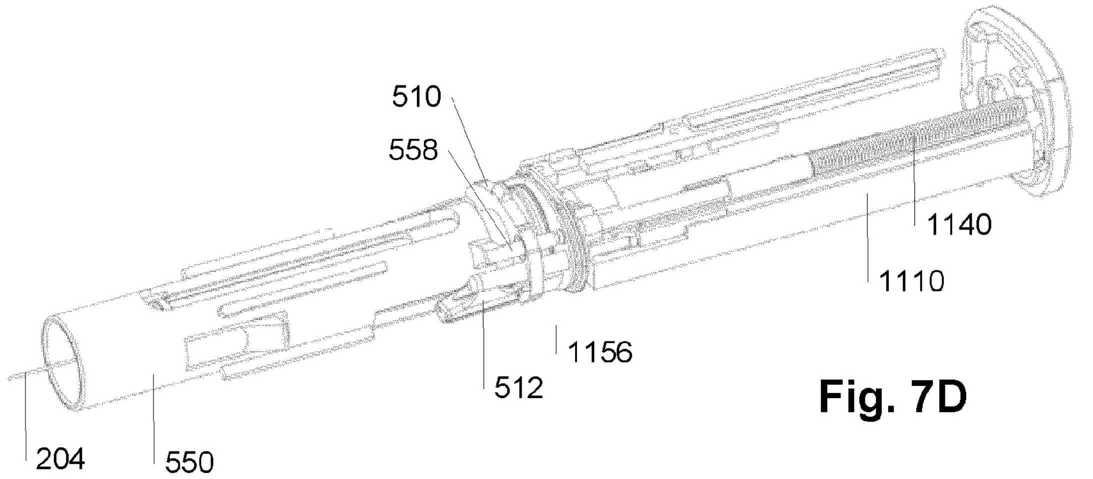
FIG. 7G shows the cassette skin sensor seen from a different angle compared to FIGS. 7A-F.
Figure 7E:
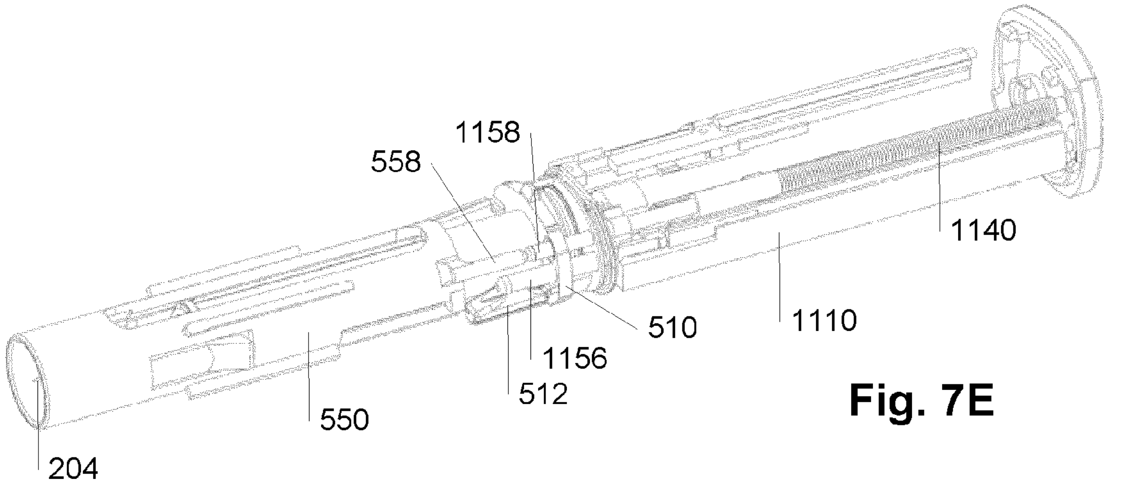
Figure 7F:
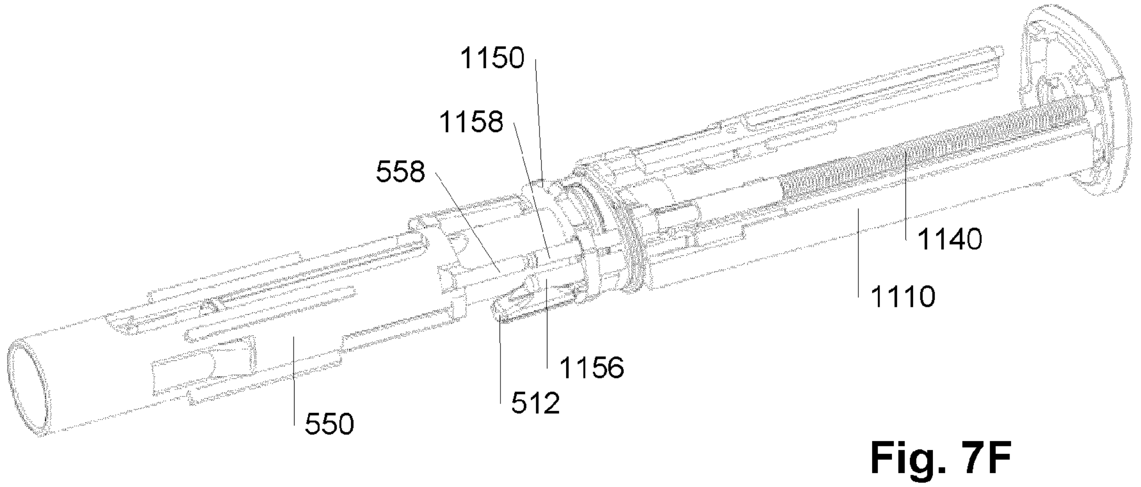
Figure 7G:
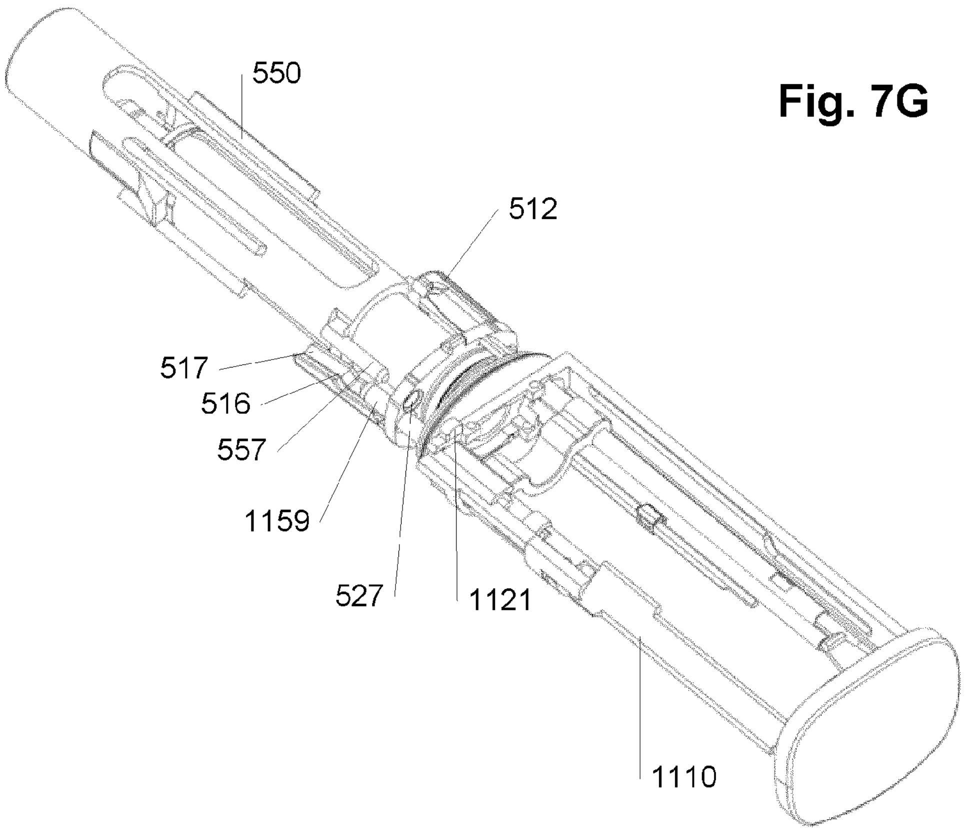

The syringe holder 510 also has a second syringe holder arm 516 extending in a proximal direction from the syringe holder plate 519 (see FIG. 7G). The second syringe holder arm 516 comprises a distal surface 518 at the proximal end of the arm. The distal surface 518 is resting against a second locking protrusion 554 on the cassette skin sensor 550. This engagement prevents movement of the cassette skin sensor 550 away from the syringe holder 510. Before unlocking the cassette skin sensor 550 and the syringe holder 510 by deflection of the first syringe holder arm 512, the two parts are thus prevented from both moving towards and away from each other.

The second syringe holder arm 516 is also flexibly connected to the syringe holder plate 519. When a second cassette locking pin 1159 of the auto injector 1000 is pushed through the fourth pin opening 529, it comes in contact with the second syringe holder arm 516 (see FIG. 7G). This results in a deflection of the second syringe holder arm 516, which in turn releases the cassette skin sensor 550 again, this time allowing it to move away from the syringe holder 510 in the proximal direction.

The third pin opening 528 allows passage of a skin sensor pin 1158 of the auto injector 1000 (see FIGS. 7A-F), which pushes on the second cassette skin sensor pin 558 of the cassette skin sensor 550. The second cassette skin sensor pin 558 may also pass through the third pin opening 528 before coming in contact with the skin sensor pin 1158.

The syringe holder 510 has two syringe holder locking protrusions 524 fitting into openings 544 at the distal end 541 of the cassette housing 540. This locks the syringe holder 510 and the cassette housing 540 together. More locking protrusions/openings could also be imagined.

The syringe holder 510 further comprises one or more syringe locking protrusions 515 locking the syringe 200 to the cassette 500.

The cassette 500 further has a cassette cap 530 having a first part 531 positioned between the rigid needle shield 206 and the proximal end of the syringe compartment 201. The cassette cap 530 comprises an inner rigid needle shield tube 535 with the first part 531 and an outer rigid needle shield tube 536. This is most clearly seen in FIGS. 6A-C. The outer rigid needle shield tube 536 surrounds the inner rigid needle shield tube 535, and the inner rigid needle shield tube 535 surrounds the rigid needle shield 206.

The outer rigid needle shield tube 536 abuts the housing shoulder 546 of the cassette housing 540 as shown in FIG.

Figure 2:
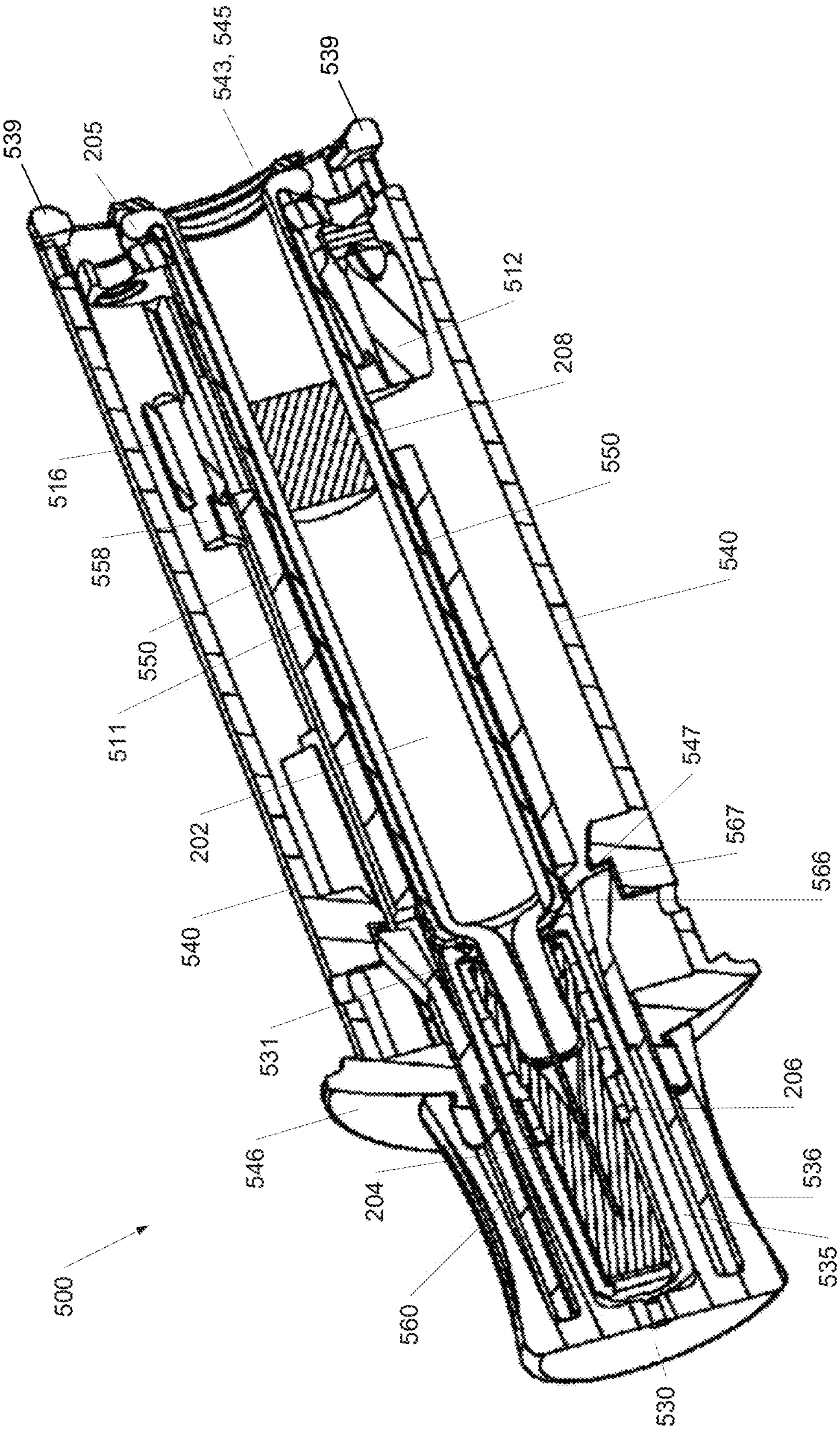
FIG. 2 shows a cut-through of the assembled cassette of FIG. 1A.

2. The proximal end 560 of the cassette skin sensor 550 is positioned between the inner rigid needle shield tube 535 and the outer rigid needle shield tube 536 as shown in FIG. 2. The cassette cap 530 is removable from the syringe compartment 202, and when the cassette cap 530 is removed, the rigid needle shield 206 follows with it, whereby the hollow needle 204 is exposed.

Figure 4A:
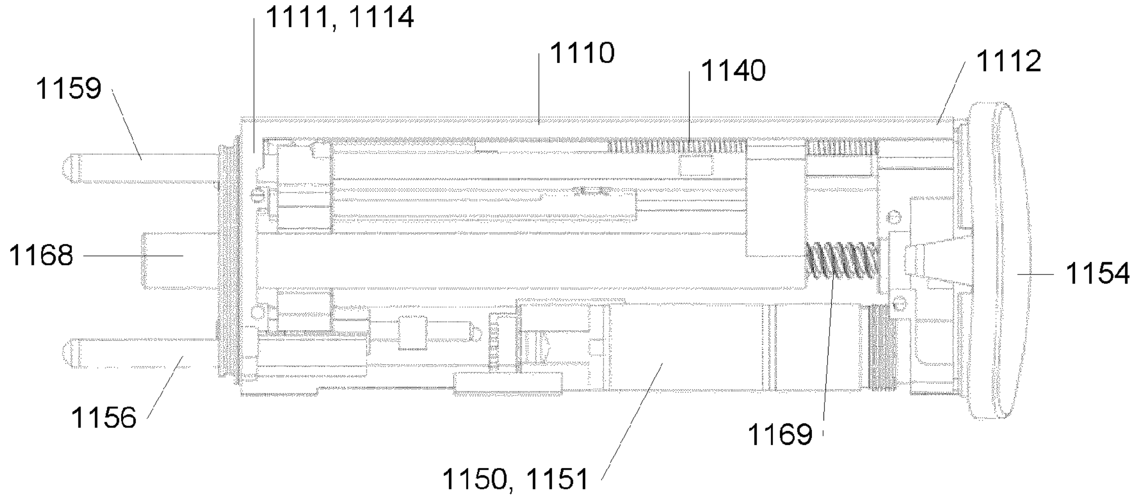
FIG. 4A shows a cut-through view and FIG. 4B a side-view of the of the auto injector of FIG. 3.
Figure 4B:
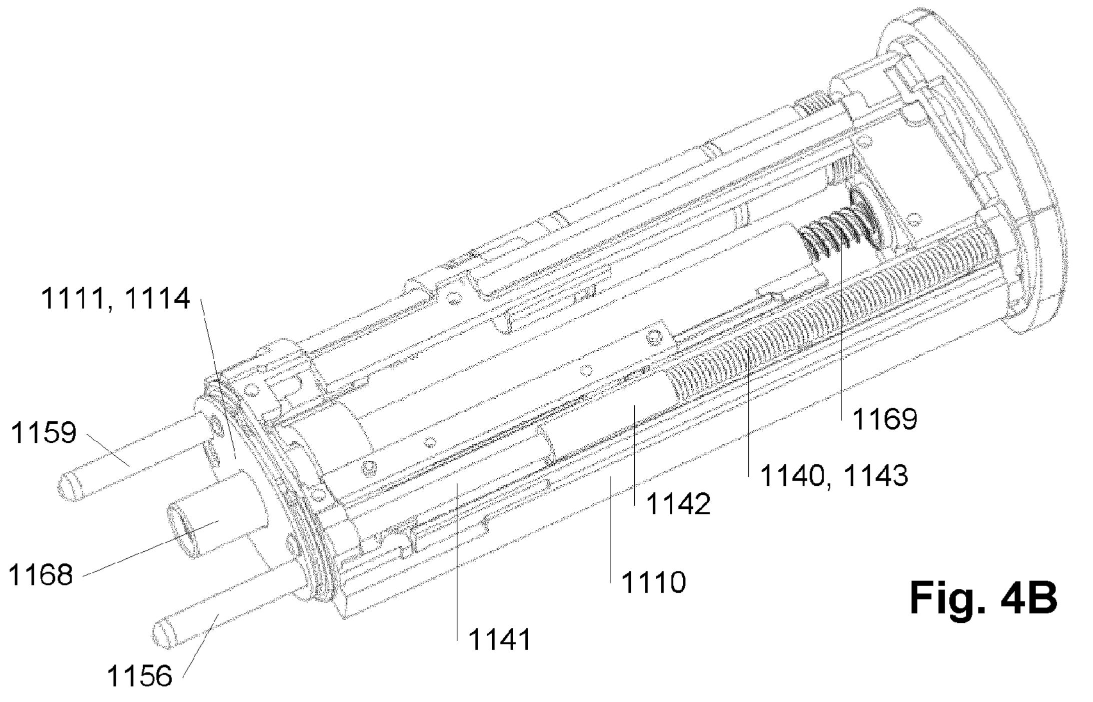
Figure 5:
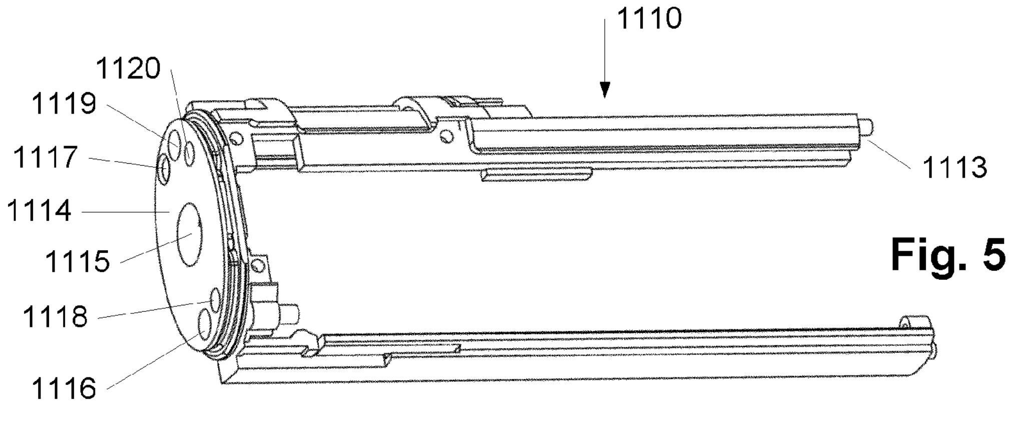
FIG. 5 shows a close-up of the chassis shown in FIG. 3.

FIGS. 3-4 show an example of an auto injector 1000 for receiving the cassette of FIGS. 1-2. The auto injector 1000 is shown in an exploded view in FIG. 3, whereas FIG. 4A-B show the assembled auto injector 1000. For obtaining a clear view inside the auto injector, the outer housing 1102 has been omitted. The outer housing 1102 can be seen in FIGS. 6A-D.

The auto injector 1000 extends from a proximal end to a distal end and comprises the housing 1102 extending from a proximal end 1103 to a distal end 1104. The housing is in one piece in this example of the auto injector. The cassette 500 is loaded into the auto injector 1000 in a front-loading configuration.

The auto injector 1000 comprises a cassette receiving chassis 1110 configured to receive the cassette 500. The cassette 500 is interfacing with the auto injector 1000 at the distal end of the cassette 500, whereby the two parts are sharing the same longitudinal axis. This mitigates the risk of the cassette getting stuck inside in the auto injector. Further, it makes the connection as slim as possible. The only auto injector element, which extends in parallel with the cassette 500 is normally the injector housing 1102. The injector housing may therefore be seen as having two sections; a cassette covering section 1108 and a distal section 1106 covering internal injector parts inside the auto injector 1000 (see the auto injector example in FIGS. 18A-B). The internal injector parts includes a drive module 1150, which is adapted to move a piston 1168. The piston 1168 is moved proximally pushing on the stopper 208 inside the syringe whereby medicament can be expelled from the syringe 200. The piston 1168 has an inner threading (not shown in the figure), which engages with an outer threading on a led screw 1169. When the lead screw 1169 is rotated by the drive element 1150, the piston 1168 moves proximally. The drive module 1150 includes a motor 1151, which through a gear assembly 1153, rotates the led screw 1151. The gear assembly 1153 is covered by a gear cover 1152, some O-rings 1155 and a chassis cover 1154. The O-rings may be seen as a noise reducing material, which dampers any noise may by the internal parts inside the auto injector during use. A similar noise reducing material is found at the proximal end of the internal parts shown here in the form of a larger O-ring 1109.

The drive element 1150 also controls the movement of a number of pins comprised in the auto injector 1000. As shown in FIG. 3, the number of pins include; a first cassette locking pin 1156, a skin sensor pin 1158, a second cassette locking pin 1159, and a cassette detection pin 1160. Thus, the drive module 1150 is further configured for moving the first cassette locking pin 1156, the skin sensor pin 1158, the second cassette locking pin 1159, and the cassette detection pin 1160 proximally. The pins and the piston may also be referred to as cassette interacting parts adapted for securing and locking the cassette 500 inside the auto injector 1000 and for facilitating administering of the medicament. In common for the cassette interacting parts shown in FIG. 3 is that they move in parallel with the longitudinal axis of the auto injector 1000.

Acting on the skin sensor pin 1158, which pushes the cassette skin sensor 550 proximally after delivery of medicament, is a spring system 1140. The spring system 1140 includes a spring guidance pin 1141 around which a supporting chassis 1142 connected to the skin sensor pin 1158 is found. Extending around the guidance pin 1141 is also a spring 1143. When the spring 1143 is allowed to relax, it pushes the supporting chassis 1142 forward, which in turn pushes the skin sensor pin 1158 proximally. Inside the skin sensor pin 1158 at the distal end thereof is a guide pin 1161 for the skin sensor pin 1158. When the skin sensor spring system 1140 pushes the cassette skin sensor 550 proximally after delivery of medicament, it is pushed into a locked position preventing distal movement of the cassette skin sensor 550. Proximal movement of the cassette skin sensor 550 may also be prevented in this locked position.

The auto injector 1000 also comprises a cassette receiving chassis 1110 configured to receive a cassette 500. The cassette receiving chassis 1110 is in the shape of a chassis as seen in FIGS. 3 and 5, the latter showing an enlarged view of the cassette receiving chassis 1110. The cassette receiving chassis 1110 is extending from a proximal end 1111 to a distal end 1112. At the proximal end 1111 of the chassis 1110, is a proximal chassis part 1114 with a number of openings including a piston opening 1115, a first pin opening 1116, a second pin opening 1117, a third pin opening 1118, a fourth pin opening 1119, and a fifth opening 1120. Depending on the number of pins in the auto injector, fewer openings could also be used. The openings are round circular openings in this shown example in FIG. 5, but may also have a different shape mimicking the shape of the pins if they are not round.

When the cassette 500 is positioned in the auto injector 1000, the piston opening 1115 is aligned with piston opening 525 in the syringe holder 510 to allow the auto injector piston 1168 to extend there through. Likewise, the first pin opening 526 in the syringe holder 510 is aligned with the first pin opening 1116 such that the first cassette locking pin 1156 can pass through both openings to deflect the first syringe holder arm 512 thereby unlocking the cassette skin sensor 550 from the syringe holder 510.

The second pin opening 1117 in the proximal chassis part 1114 is aligned with the second pin opening 527 in the syringe holder 510 for allowing passage of the first cassette skin sensor pin 557 of the cassette skin sensor 550 to pass there through. The second pin opening 1117 does not extend all the way through, but instead has an end surface 1121 (see FIG. 7G), which stops the first cassette skin sensor pin 557 of the cassette skin sensor 550 in its distal movement towards the auto injector. Thus, the second pin opening 1117 is a well-shaped opening with an end surface 1121 limiting the distal movement of the first cassette sensor pin 557 and thereby the cassette skin sensor 550 inside the auto injector 1000.

The third pin opening 1118 is aligned with the third pin opening 528 in the syringe holder 510 for allowing passage of the skin sensor pin 1158, and/or the second cassette skin sensor pin 558 there through. This is shown in details in FIGS. 7A-F. The fourth pin opening 1119 is aligned with the fourth pin opening 529 in the syringe holder 510 for allowing passage of the second cassette locking pin 1159 there through.

The fifth opening 1120 does not have a corresponding opening in the syringe holder. Instead, through the fifth opening 1120 cassette detection pin 1160 extends. The cassette detection pin 1160 detects when a cassette 500 is connected to the auto injector 1000. The release of the cassette skin sensor 550 will not occur if there is no detection of a cassette by the cassette detection pin 1160. Instead of a cassette detection pin, a detection system based on e.g. magnets on cassette and auto injector surfaces coming in contact with each other and a corresponding Hall sensor inside the chassis may be used elimination the need for a detection pin and a corresponding opening in the proximal chassis part 1114. Alternatively, the cassette may have a pin, which comes in contact with a surface on the injector, whereby detection of the cassette is registered in the auto injector.

The cassette receiving chassis 1110, the piston 1168 and the drive module 1150 are comprised inside the housing 1102 of the auto injector 1000, and the cassette 500 is removable received in the auto injector 1000. By removable received is meant is meant that the cassette is a disposable cassette, which may be received in a reusable auto injector. The disposable cassette may be a one-time use cassette, or a cassette comprising multiple doses for multiple individual injections.

Figure 6A:
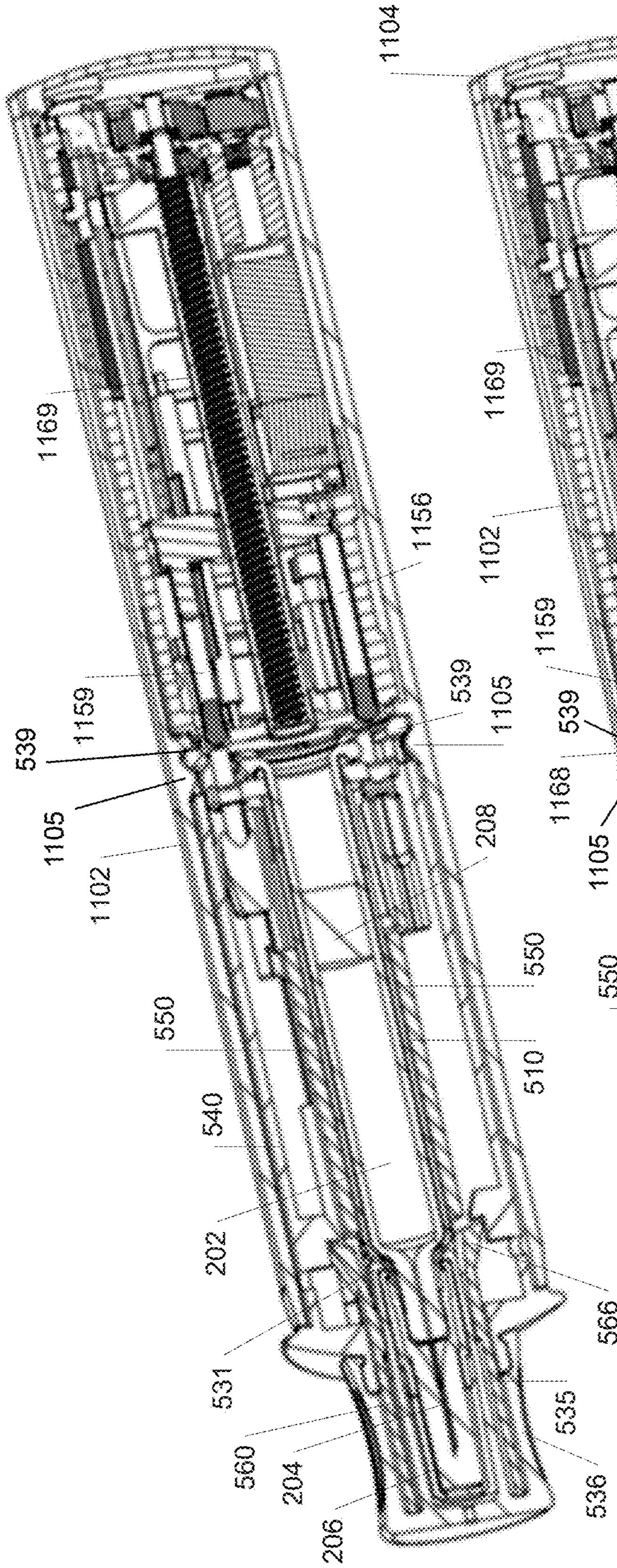
FIGS. 6A-C show cut-through views of the auto injector of FIGS. 3-5 with a cassette as shown in FIGS. 1-2 in different positions during loading and locking of the cassette in the auto injector, and FIG. 6D show the auto injector with the cassette in a perspective view.
Figure 6B:
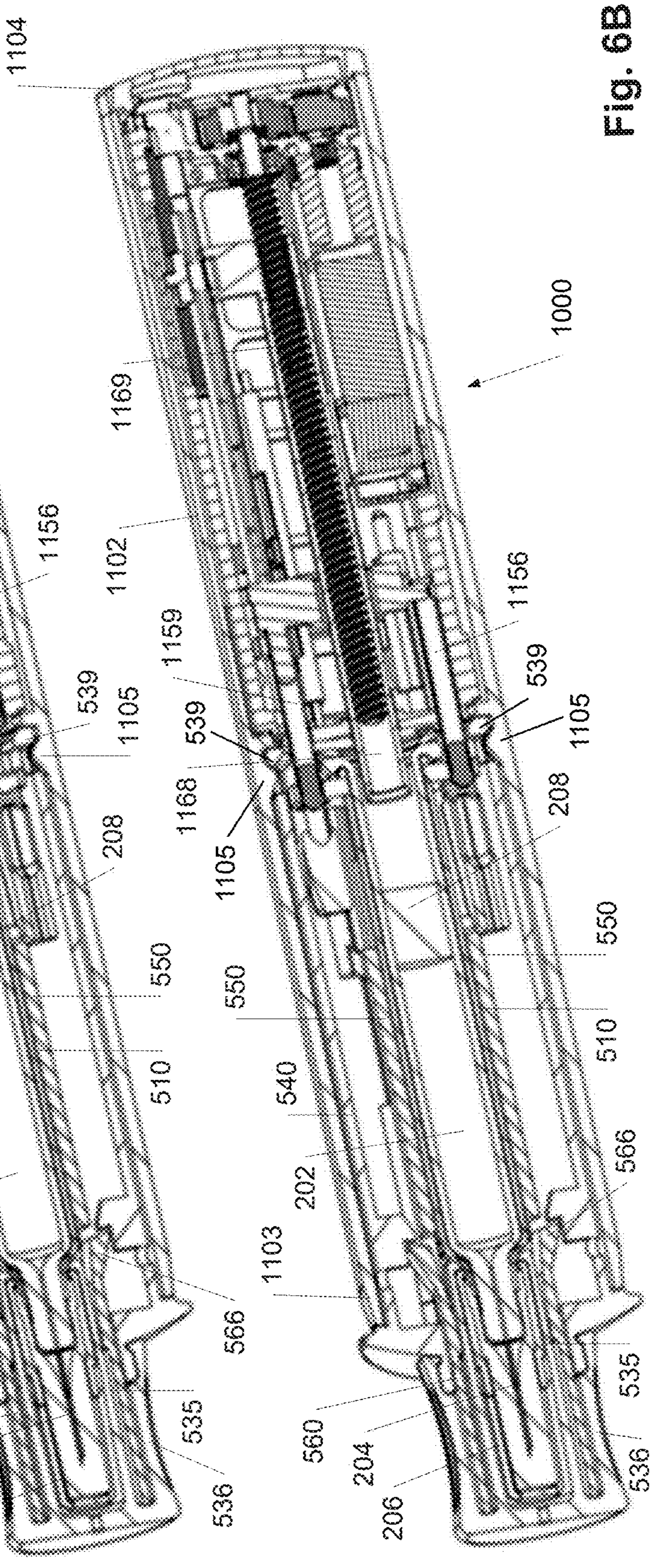
Figure 6C:
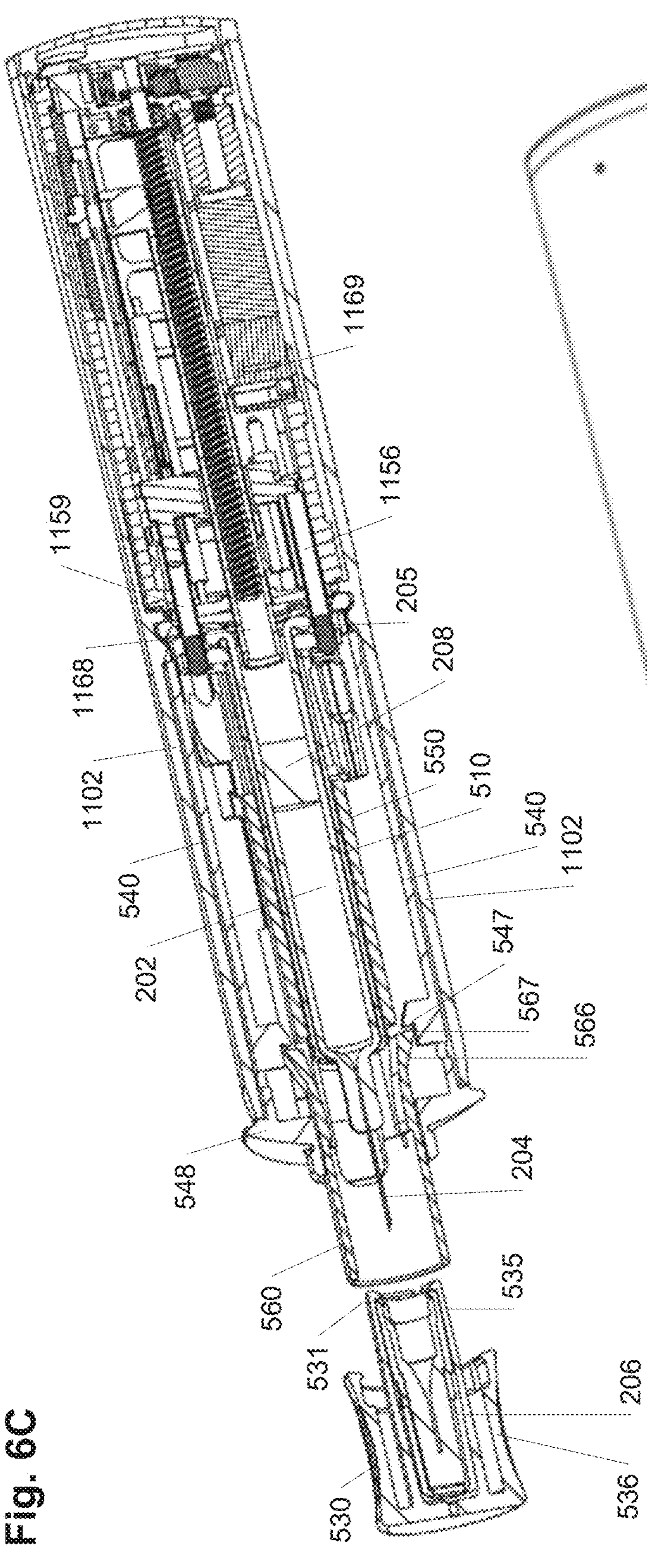
Figure 6D:
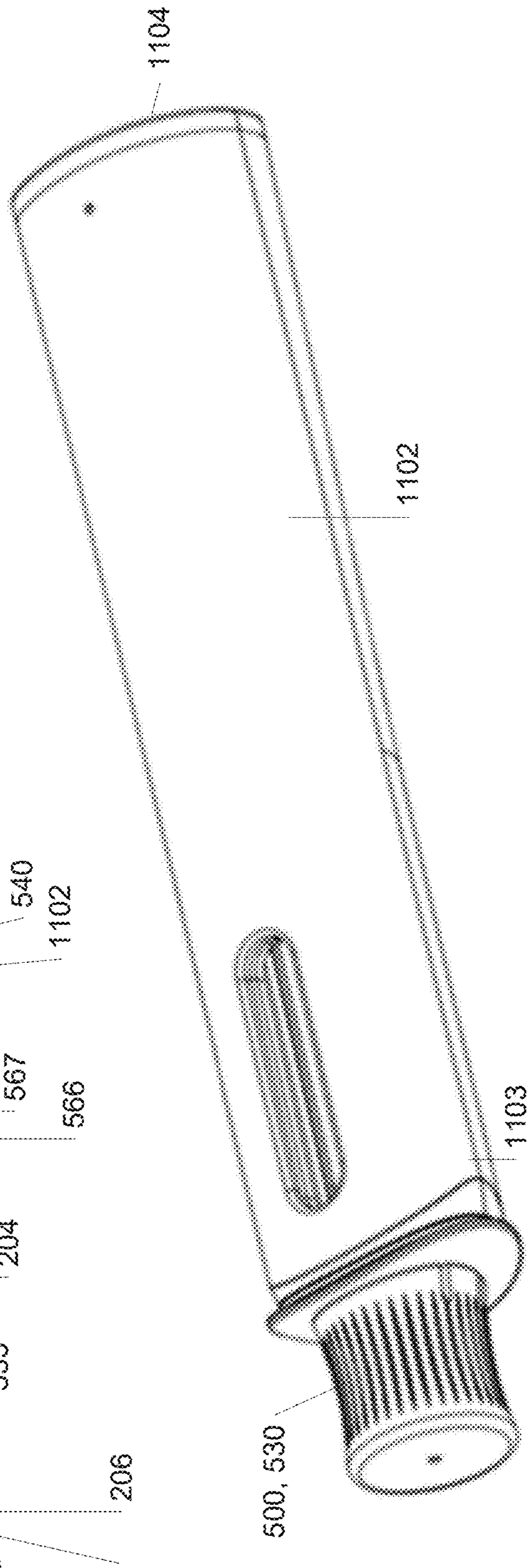

FIGS. 6A-C show cut-through views of the auto injector 1000 with the cassette 500 during the loading and locking of the cassette 500 in the auto injector 1000. In FIG. 6A, the cassette 500 has been received inside the auto injector housing 1102. As seen in FIGS. 6A-C, the injector housing 1102 has protruding tabs 1105 on its inside. When the cassette 500 is positioned in the auto injector 1000, cassette locking protrusions 539 are positioned near the protruding tabs 1105. The auto injector then moves the cassette locking pins 1156, 1159 forward along with the piston 1168 as seen when comparing FIGS. 6A and 6B. The cassette locking protrusions 539 are now prevented from deflecting by the protruding tabs 1105, thereby locking the cassette 500 to the auto injector 1000. As the cassette 500 is now firmly locked inside the auto injector 1000, the cassette cap 530 can now be manually removed from the cassette 500. This also removes the rigid needle shield 206 exposing the needle 204.

By further proximal movement of at least the first cassette locking pin 1156, the cassette skin sensor 500 is released from the syringe holder 510. This process is shown in FIGS. 7A-C illustrating the steps in releasing the cassette skin sensor 550 from the syringe holder 510 by means of moving the first cassette locking pin 1156 proximally. As seen in FIG. 7B, the first locking protrusion 553 and the proximal surface 514 of the arm 512 no longer engage. The auto injector is now ready for insertion of the needle 204 into a patient. This is done by pressing the cassette 500 towards the skin of the patient thereby pushing the cassette skin sensor 550 distally as shown in FIGS. 7C and 7D. Thus, when the drive module 1150 moves the first cassette locking pin 1156 proximally, the cassette skin sensor 550 is distally unlocked from the syringe holder 510 allowing for distal movement of the cassette skin sensor 550, wherein the unlocking of the cassette skin sensor 550 locks the cassette 500 in the auto injector 1000.

When the drive module 1150 moves the piston 1168 proximally for delivery of medicament, the second cassette locking pin 1156 is also unlocked for movement of the cassette skin sensor 550 proximally after delivery of medicament and/or removal of the auto injector 1000 from the patient's skin.

FIGS. 7D-E show the locking of the cassette skin sensor 550 in a proximal position after delivery of medicament. FIG. 7D illustrates delivery position. In this position, the skin sensor pin 1158 exerts a pressure on the second cassette skin sensor pin 558 by the spring system 1140. In FIG. 7E, the auto injector has been lifted from the skin of the patient. By doing so, the spring system 1140 pushes the cassette skin sensor 550 forward in the proximal direction. As the cassette skin sensor 550 has been unlocked for movement in the proximal direction by second cassette locking pin 1159, the cassette skin sensor 550 can be locked in a forward position where contact with the needle is prevented by e.g. a protrusion inside the cassette housing engaging with the cassette skin sensor protrusion.

After delivery of medicament, the drive module retracts the piston and the skin sensor release pins 1156, 1157, which unlocks the cassette from the auto injector allowing the user to remove the cassette. The rigid needle shield and the cassette cap cannot be connected to the cassette after use, which ensures that the user will not mistake a used cassette for a non-used.

In FIGS. 8A-B and FIGS. 9A-C is shown the assembly of a cassette 500 comprising similar parts as shown and discussed in the previous figures. FIG. 8A show a cassette housing 540 and a cassette cap 530, which is assembled in FIG. 8B to form an outer cassette part 504 by connecting a proximal end 541 of the cassette housing 540 to a distal end 534 of the cassette cap 530. Compared to the corresponding cassette housing 540 in FIGS. 1A, 2, and 6A-D, the cassette housing in FIGS. 8A-B is absent of a housing shoulder 546.

The cassette cap 530 comprises a first part 531 at the distal end 534 of the cassette cap 530. The first part 531 may be part of an inner rigid needle shield tube 535 surrounded by an outer rigid needle shield tube 536. If a syringe comprising a rigid needle shield is positioned in the cassette 500, the first part 531 will normally be positioned between the rigid needle shield 206 and the proximal end of the syringe compartment or around the rigid needle shield 206 as shown in FIG. 15D, where the first part 531 is positioned around the distal end of the rigid needle shield. The first part 531 of the cassette cap 530 extend inside the cassette housing opening 545 when the outer cassette part 504 is assembled as shown in FIG. 8B.

Figure 9D:
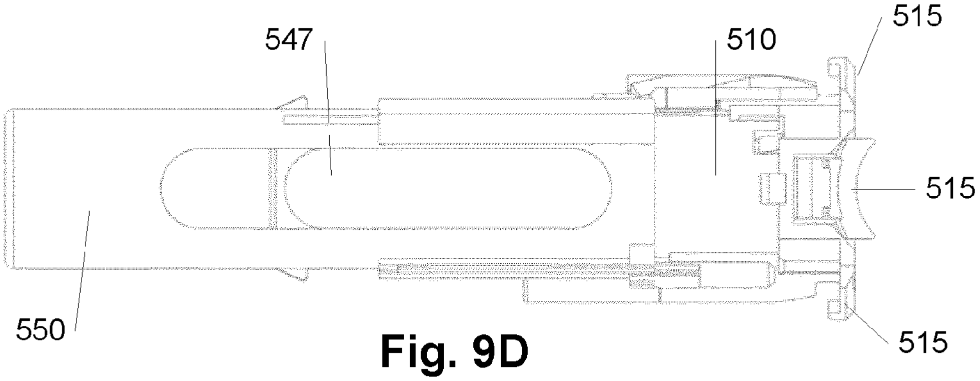
FIG. 9D shows a cut-through of the inner cassette part of FIG. 9C.

FIGS. 9A-C show the assembling of an inner cassette part 501 comprising a syringe holder 510 and a cassette skin sensor 550. In FIG. 9A, the two parts are shown as separate parts before assembling by inserting a proximal end 508 of the syringe holder 510 into a distal end 552 of the cassette skin sensor 550. In FIG. 9B, the syringe holder 510 has been pushed part of the way into a distal end 552 of the cassette skin sensor 550, and in FIGS. 9C-D, the two parts have been assembled such that a part of the syringe holder 510 is covered by the cassette skin sensor 550. The part of the syringe holder 510 covered by the cassette skin sensor 550 constitutes at least 10%, such as at least 20%, such as at least 30%, such as at least 40%, such as at least 50%.

Figure 10A:
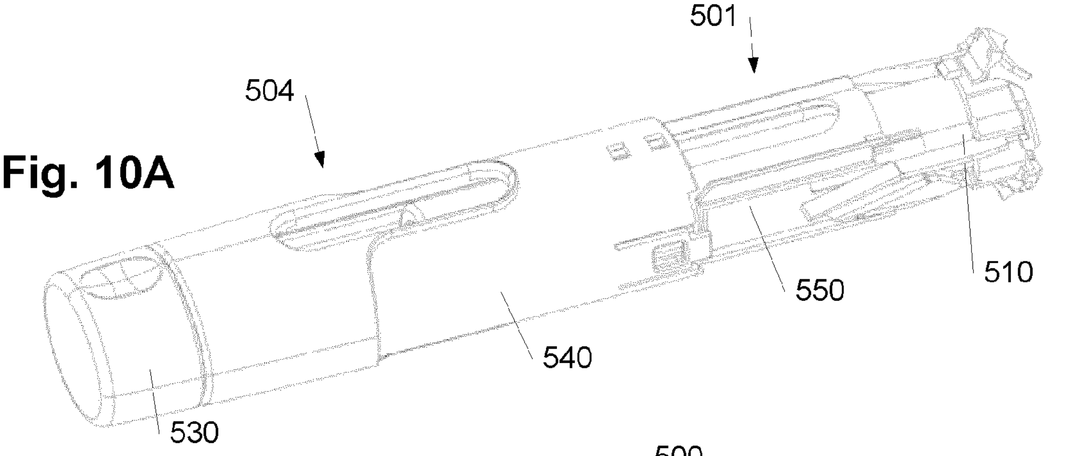
FIGS. 10A-C show the assembly of a cassette comprising the outer cassette part of FIGS. 8A-C and the inner cassette part of FIGS. 9A-D.
Figure 10B:
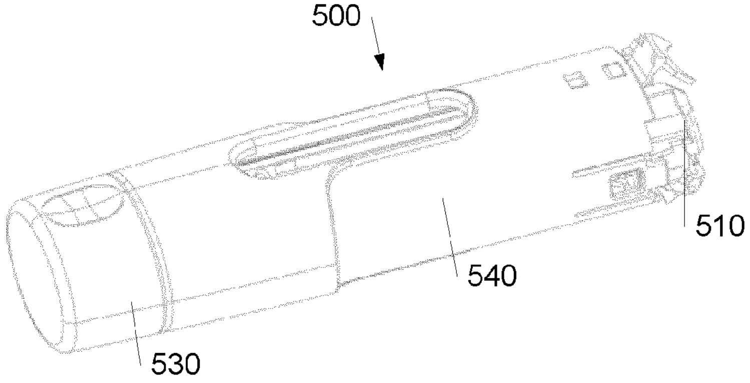
Figure 10C:
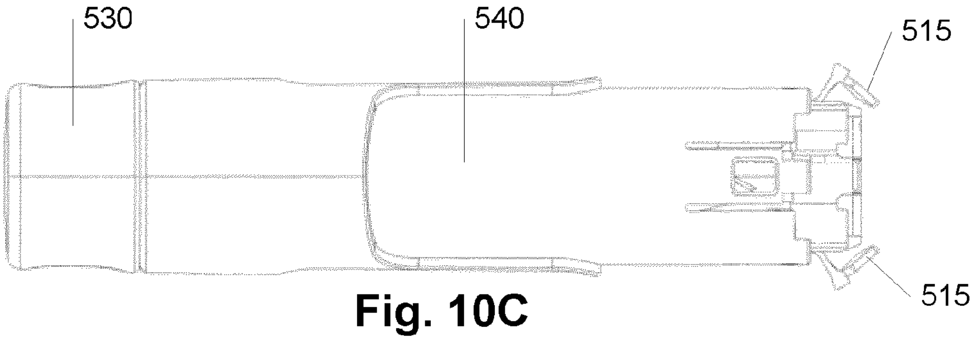

The inner and outer cassette parts are assembled by inserting a proximal end 502 of the inner cassette part 501 into a distal end 506 of the outer cassette part 504 and pushing the inner cassette part 501 into the outer cassette part 504 such that the majority of the inner cassette part 501 is covered by the outer cassette part 504. This is shown in FIGS. 10A-B, where FIG. 10A shows the initial position of the cassette parts before they have been completely assembled in FIGS. 10B-C.

Figure 11A:
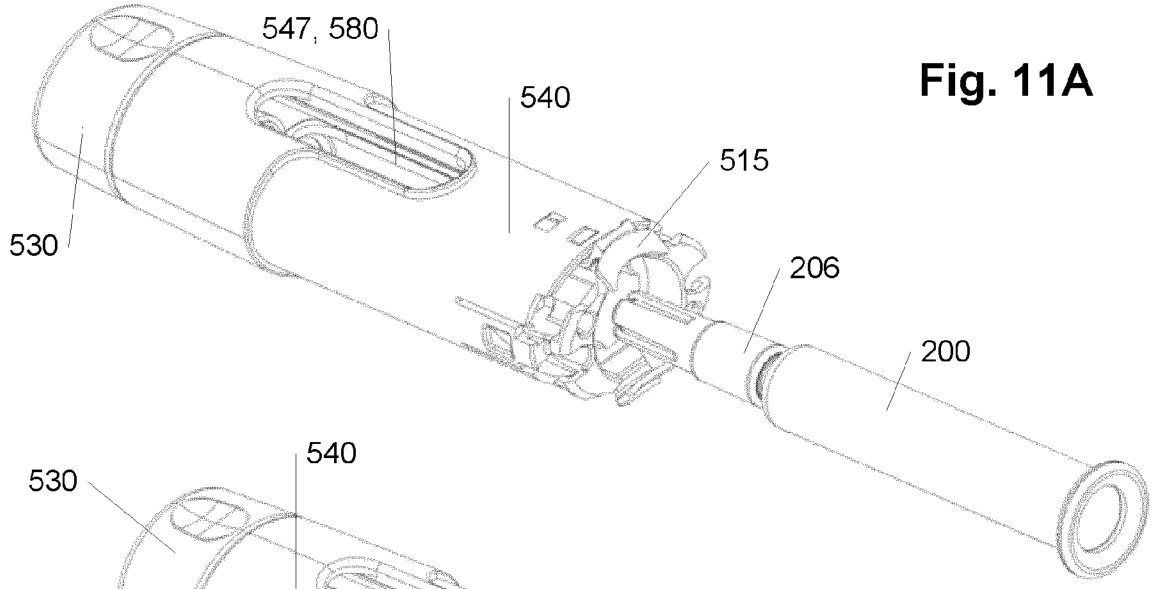
FIGS. 11A-D show the assembly of the cassette of FIGS. 10B-C with a syringe.
Figure 11B:
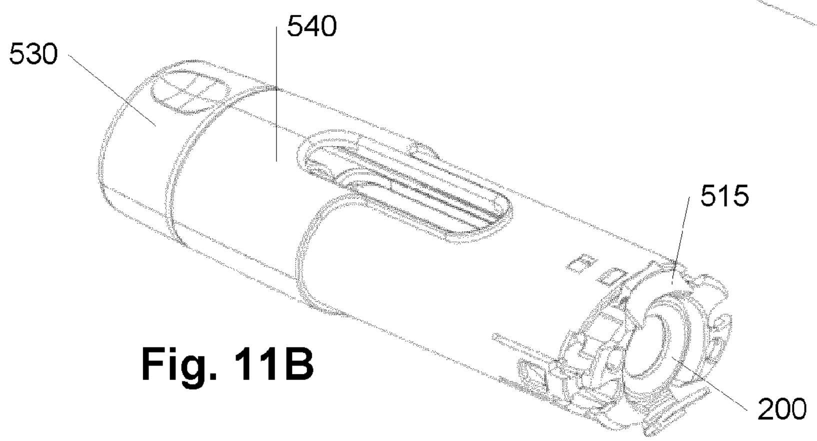
Figure 11C:
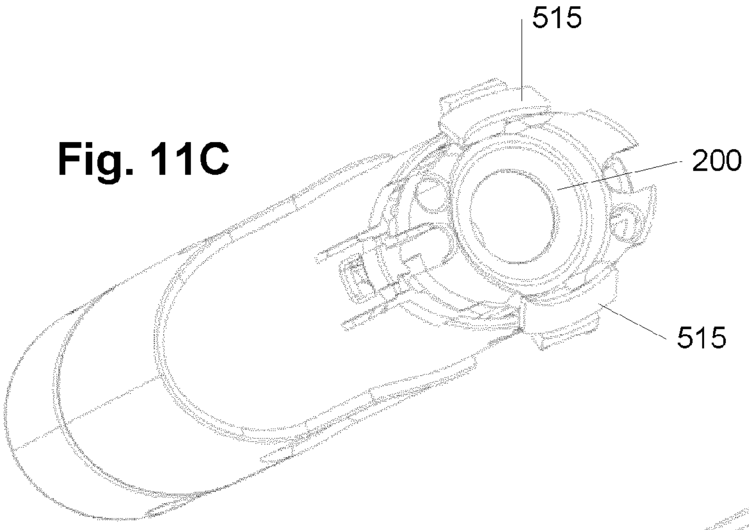
Figure 11D:
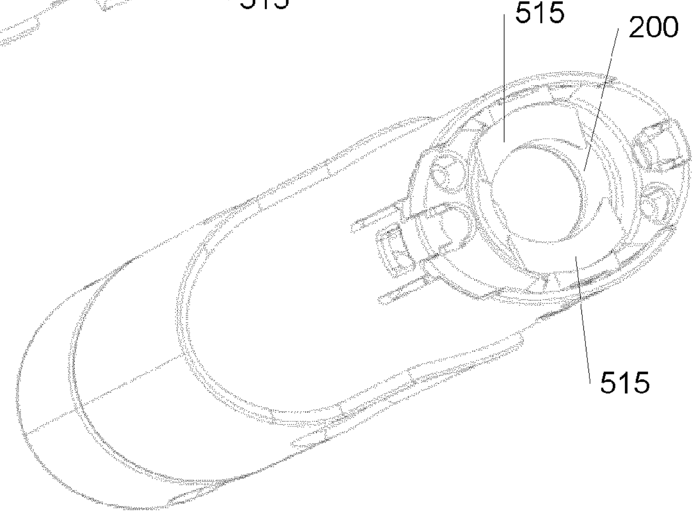

FIGS. 11A-D shows the insertion and fixation of a syringe 200 inside the cassette 500. The cassette parts can be assembled on one location and the syringe inserted at a different location. In FIG. 11A, the syringe 200 is ready for insertion into the cassette 500 by inserting a proximal end of the syringe 200 into the distal end 503 of the inner cassette part 501, and pushing the syringe 200 into the inner cassette part 501 as shown in FIGS. 11B-C.

The syringe holder 510 shown in FIGS. 9A-11D comprises one or more syringe locking protrusions 515. By moving the one or more syringe locking protrusions 515 centrally, the syringe 200 is locked inside the inner cassette 501. This is seen by comparing FIGS. 11C and 11D. If the cassette housing is without the cassette locking protrusions, the syringe may be fixed in the syringe holder 510 be frictional force.

The syringe 200 extends from a proximal end 201 to a distal end 203 and comprises a syringe compartment 202 containing medicament where a proximal end is adapted for being in connection with a needle through which the medicament is allowed to exit the syringe compartment 202. In FIG. 11A, the needle is shown as a hollow needle 204 in fluid connection with the proximal end of the syringe compartment, i.e. connected to the syringe as part of the syringe. Alternatively, a luer lock needle may be connected to the syringe prior to injection of medicament. As yet a further alternative, a syringe system with a cartridge terminated with a stopper at its distal end and a rubber septum at its proximal end, where a penetrating needle at a distal end pierces the septum when mounted onto the cartridge while a proximal needle end penetrates into the patient skin. Inside the syringe compartment 202 is a stopper 208 adapted for being moved from a distal position to a proximal position inside the syringe compartment 202. This forces the medicament out of the syringe.

The syringe 200 shown in FIG. 11A also comprises a rigid needle shield 206 connected to the proximal end of the syringe compartment and covering the hollow needle 204. If the hollow needle is not part of the syringe, but instead connected thereto prior to medicament delivery, e.g. by a luer lock or a needle system penetrating a septum in the syringe when connected to the cassette, the rigid needle shield 206 may still be present as part of the cassette and used after medicament delivery for shielding the used needle for the user.

Figure 12A:
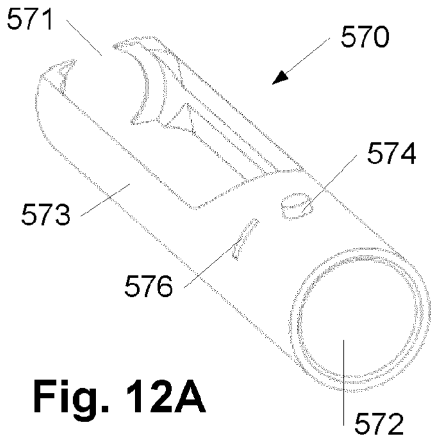
FIGS. 12A-B show a cassette sleeve.
Figure 12B:
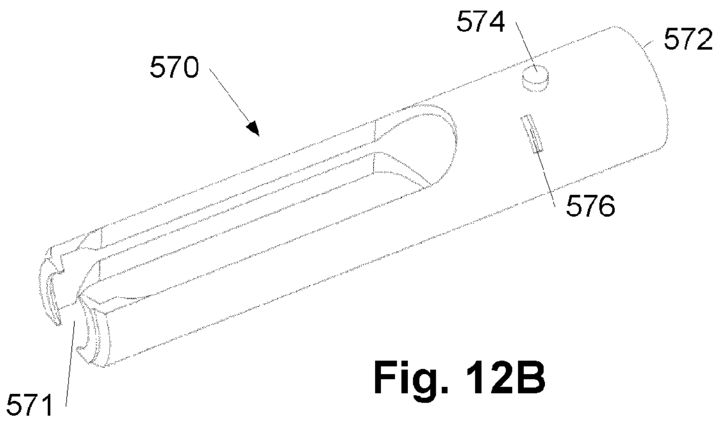

The syringe may contain different amounts of medicament such as e.g. 1.00 ml or 2.25 ml medicament. When using the cassette 500 for smaller syringes, a cassette sleeve 570 may be included inside the syringe holder 510 to ensure that a thin syringe 200 is kept inside the syringe holder 510. An example of a cassette sleeve is shown in FIGS. 12A-B. Prior to inserting a syringe 200 into a cassette 500 comprising the cassette sleeve 570, a proximal end 571 of the cassette sleeve 570 is inserted into the distal end 509 of the syringe holder 510 and pushed into the syringe holder 510 such that the majority of the cassette sleeve 570 is covered by the syringe holder 510 prior to or directly after inserting the syringe holder 510 into the cassette skin sensor 550. The cassette sleeve 570 thereby constituting a part of the inner cassette part 501 is shown as an included part in the cassette 500 in FIG. 14A. The sleeve 570 is secured in the syringe holder 510 by a small tap inside the syringe holder, which fits into the small opening 576 in the cassette sleeve 570.

The cassette sleeve 570 comprises proximal extending deflectable sleeve arms 573 (see FIGS. 12A-B). The deflectable sleeve arms 573 can deflect through an opening 580 in the syringe holder 510.

Figure 15A:
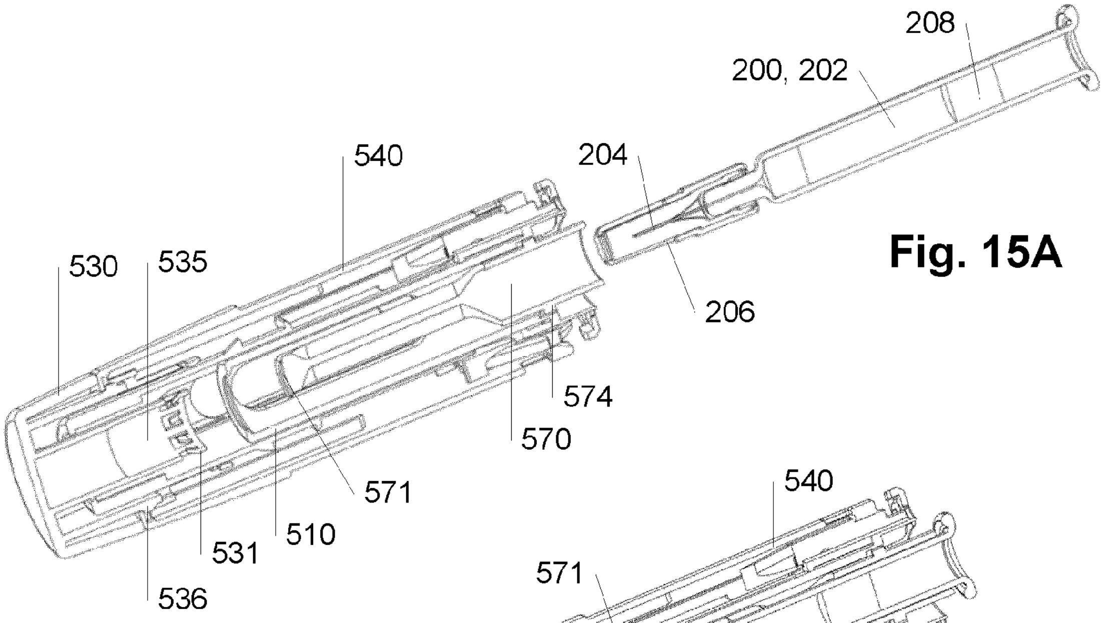
FIGS. 15A-D show the assembling of a syringe into a cassette having a cassette sleeve as shown in FIGS. 12A-B included in a cut-through view as compared to FIGS. 14A-E.
Figure 15B:
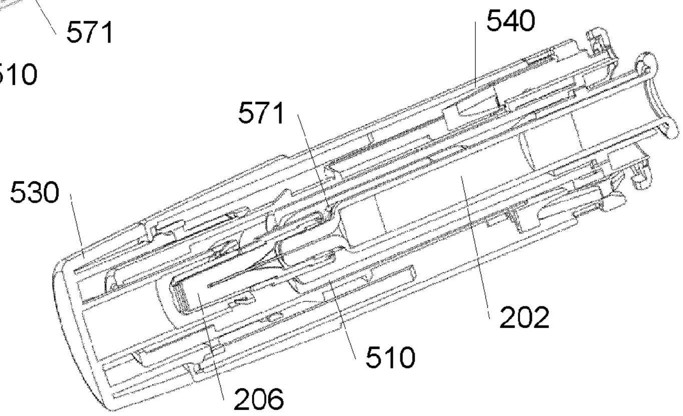
Figure 15C:
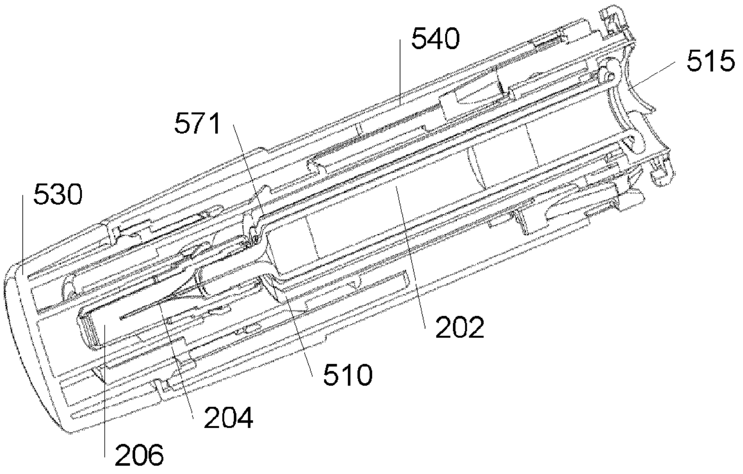
Figure 15D:
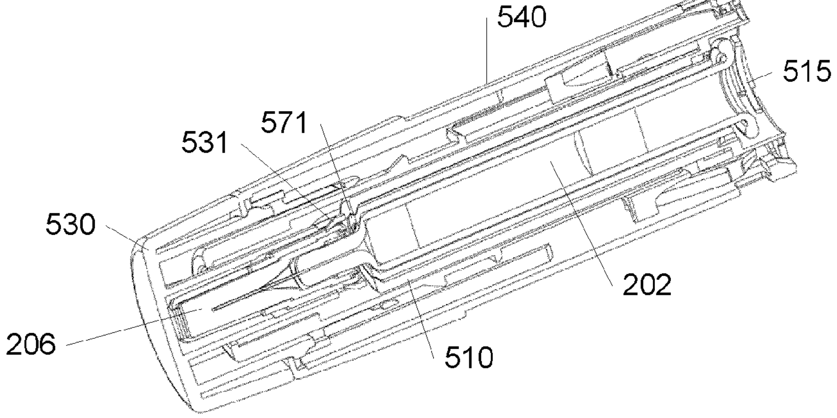

In FIGS. 14A-E and 15A-D, inserting a syringe 200 inside a cassette 500 comprising the cassette sleeve 570 is shown. When inserting a syringe 200 comprises the hollow needle 204 and a rigid needle shield 206, the deflectable sleeve arms 573 deflects into openings in the syringe holder 510 and cassette skin sensor 550 allows the rigid needle shield 206 to pass the deflectable sleeve arms 573. By this motion, the locking in the opening 576 in the cassette sleeve 570 is unlocked. Further, the deflectable sleeve arms 573 relax into a position between the rigid needle shield 206 and the syringe compartment 202 after the rigid needle shield 206 has passed the deflectable sleeve arms 573. This is seen in FIGS. 14B and 15B, where the rigid needle shield 206 is shown after having passed the deflectable sleeve arms 573.

After the deflectable sleeve arms 573 has relaxed into a position between the rigid needle shield 206 and the syringe compartment 202, and the syringe 200 is pushed further proximally before locking it to the cassette 500, the cassette sleeve 570 rotates into a position from where the sleeve arms 573 cannot deflect. The rotation of the cassette sleeve 570 is seen in FIGS. 14B-14D, with FIG. 14B showing the sleeve 570 prior to rotation, FIG. 14C showing the sleeve 570 halfway rotated and FIG. 14D showing the sleeve 570 fully rotated. The rotation may also be seen in the cut-through illustrations in FIGS. 15B-D. The rotation of the cassette sleeve 570 rotates it into a position allowing a viewer to view the medicament inside the syringe 200.

Figure 13A:
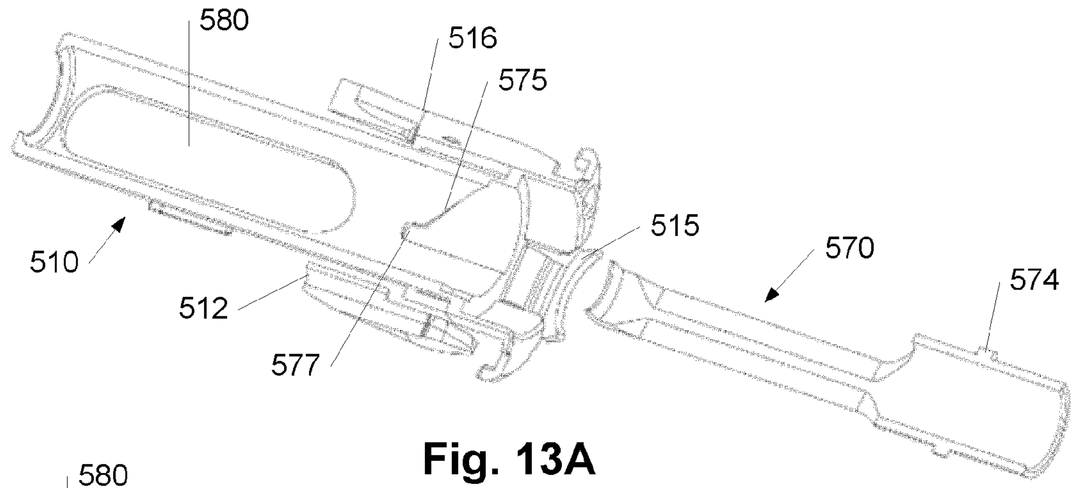
FIG. 13A-B show a cassette sleeve and the inside of a syringe holder.
Figure 13B:
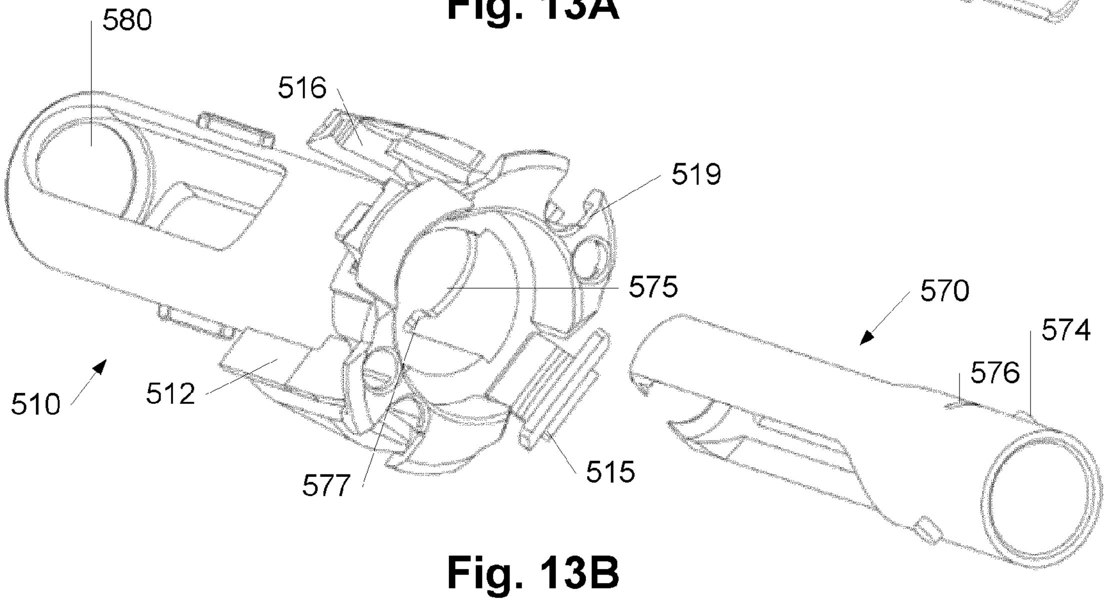

The cassette sleeve 570 comprises at least one sleeve locking protrusion 574 as shown in FIGS. 12A-B. When the sleeve locking protrusion(s) 574 comes in contact with an inner helical surface part 575 inside the syringe holder 510 as the syringe 200 is pushed proximally, the helical shape of the at least one inner helical surface part 575 forces the cassette sleeve 570 to rotate. The rotation is approximately 90 degrees. The inner helical surface part 575 is shown in FIGS. 13A-B. When the syringe 200 has been inserted in the cassette 500 and the syringe locking protrusions 515 locked around the syringe 200 preventing it and thereby the also the cassette sleeve 570 from moving in the distal direction, the cassette sleeve 570 cannot rotate backwards as this rotational motion would require that the cassette sleeve 570 moves in the distal direction due to the interaction of the inner helical surface part 575 and the sleeve locking protrusion 574. Thus, backwards rotation of the cassette sleeve 570 is prevented by the locking of the syringe 200 in the cassette 500. Further rotational movement of the sleeve 570 is also prevented as the inner helical surface part 575 has an end surface point 577 stopping the rotational motion in the first direction. The end surface point 577 may be a small opening into which the sleeve locking protrusion 574 enters without the option to move away again.

Figure 16:
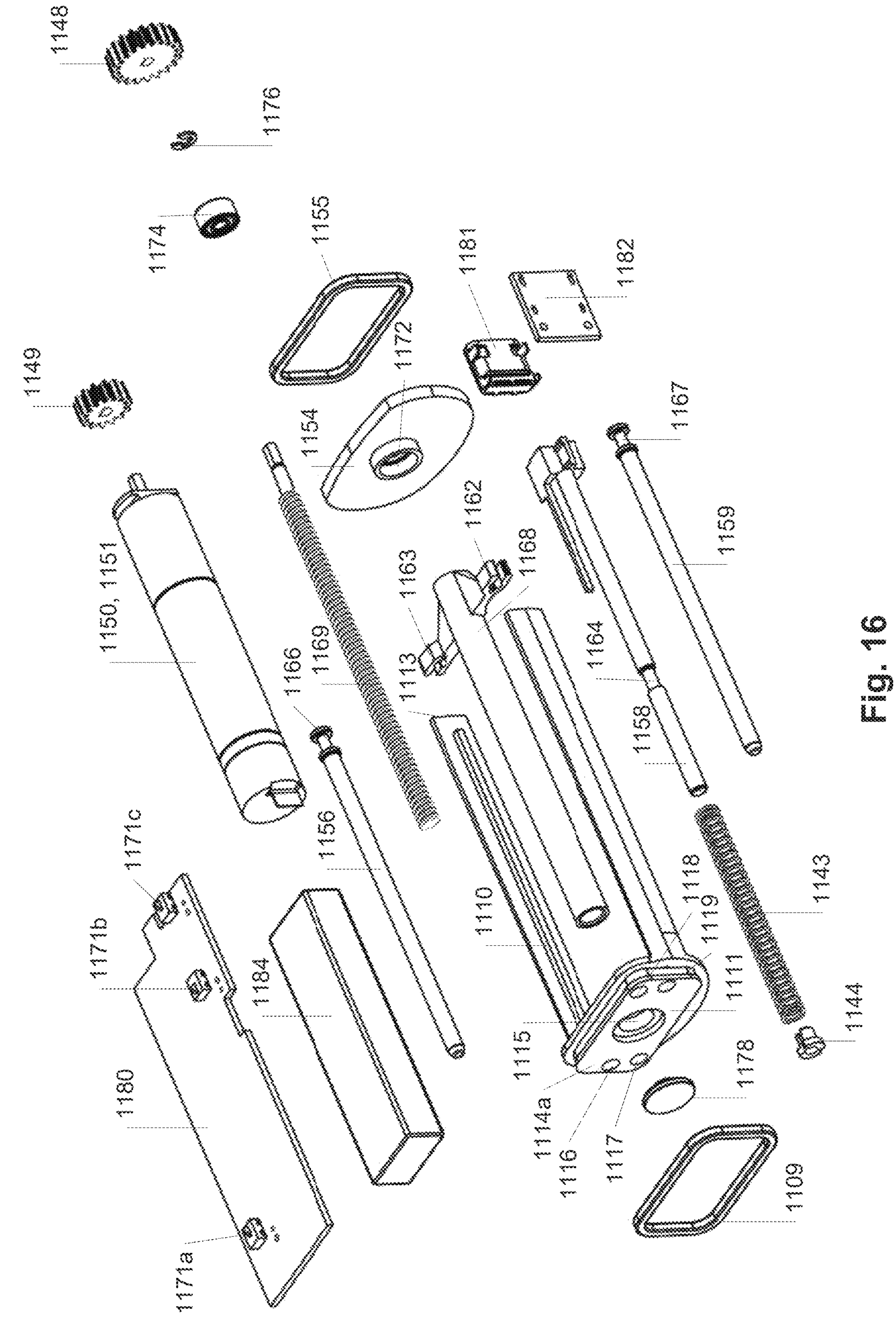
FIG. 16 shows an example of an auto injector for receiving a cassette as shown e.g.
Figure 17:
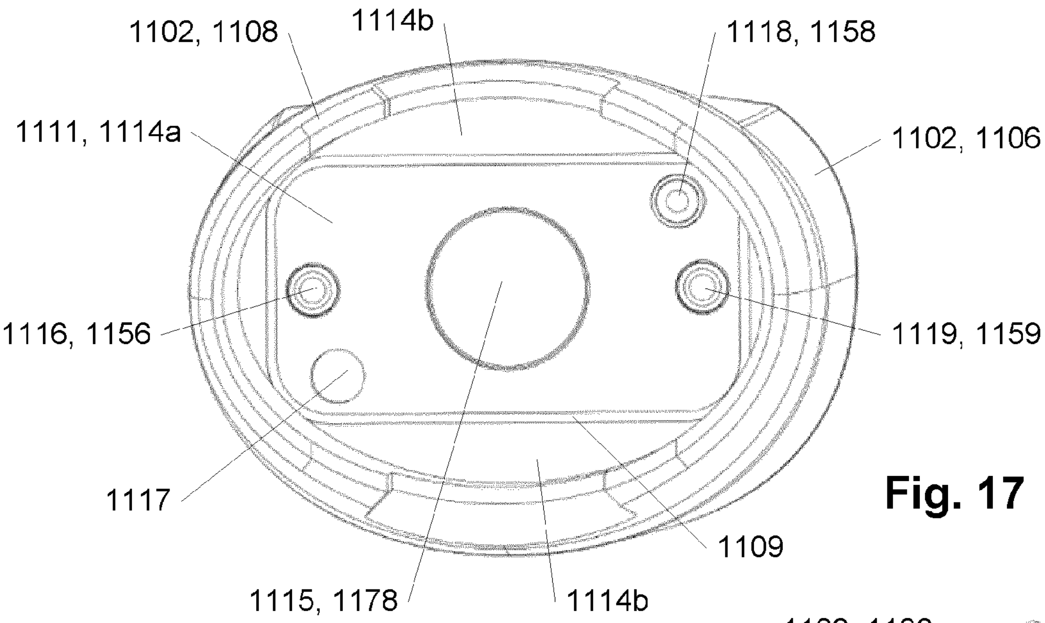
FIG. 17 shows a view into an assembled auto injector as shown in FIG. 16.
Figure 18A:
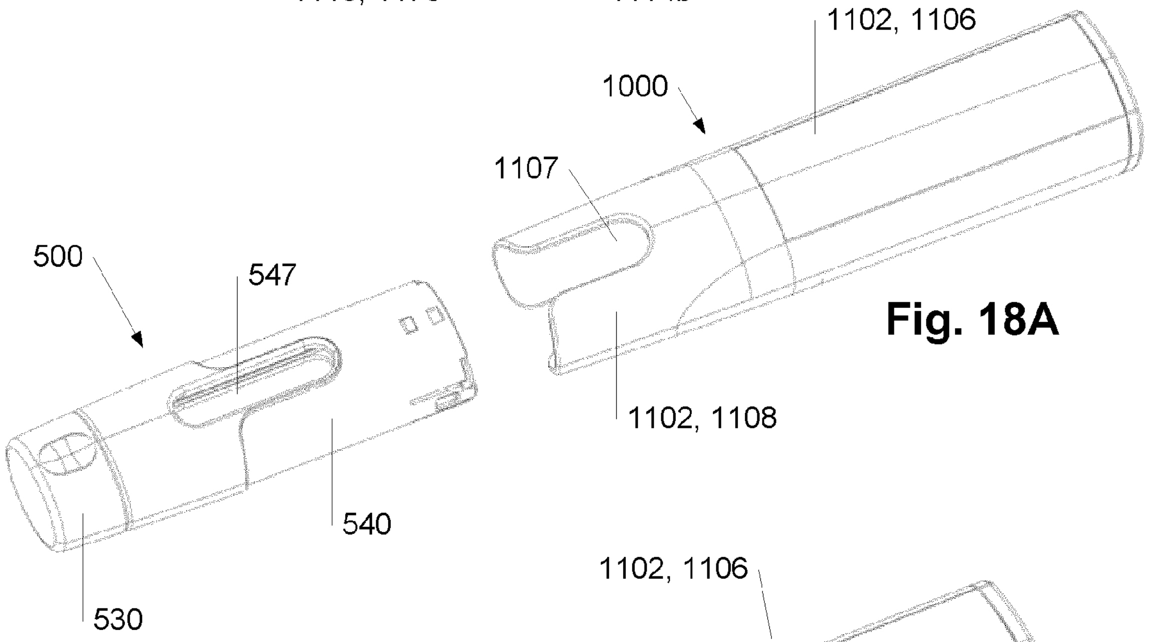
FIGS. 18A-B show the assembling of a cassette and an auto injector.
Figure 18B:
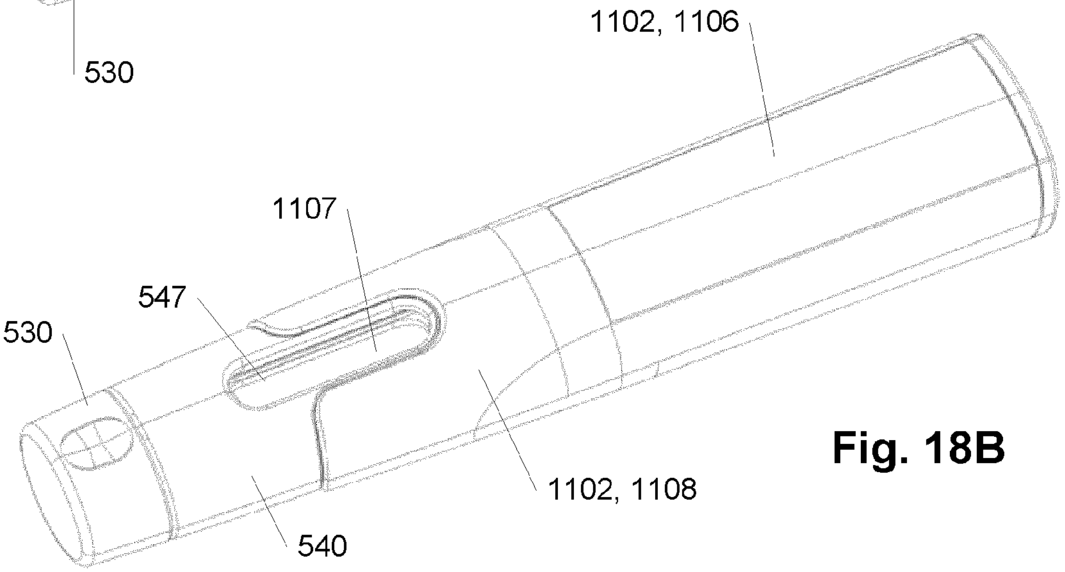
Figure 19:
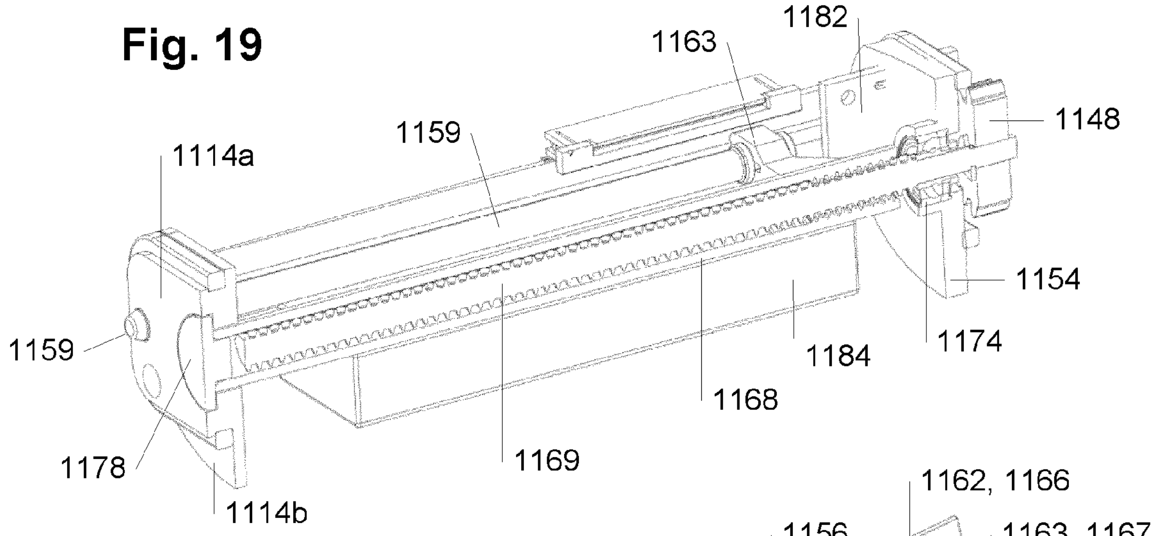
FIG. 19 shows a cut-through of the internal parts in the auto injector of FIGS. 16-18.
Figure 20A:
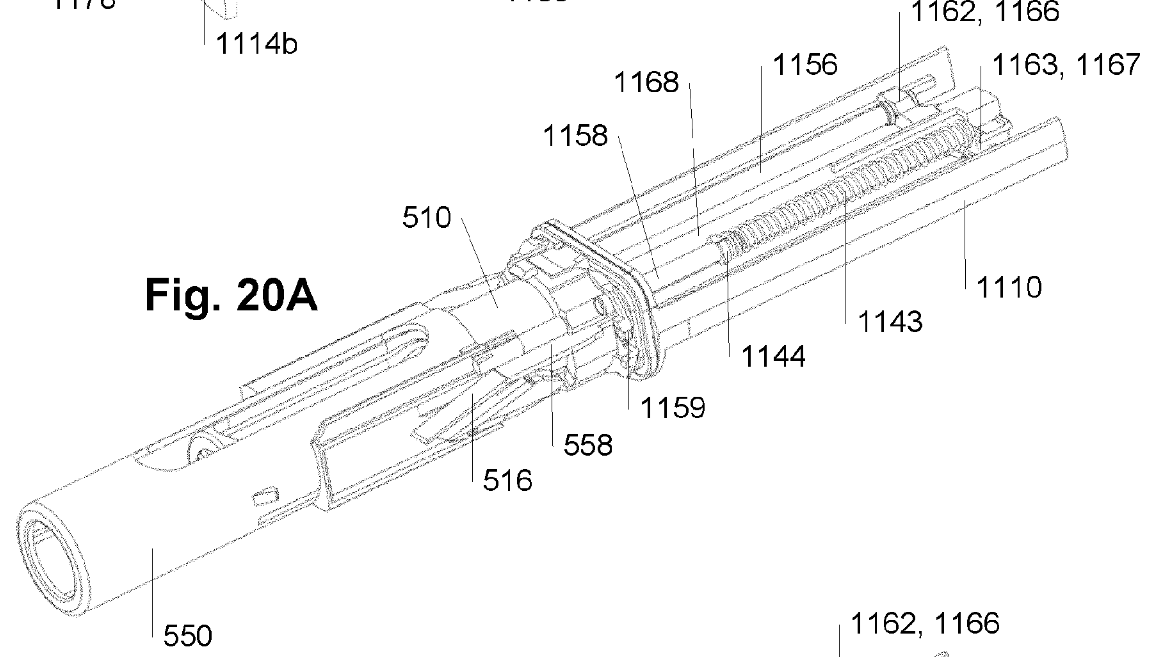
FIGS. 20A-I show the steps in releasing the cassette skin sensor from the syringe holder in the cassette, and locking of the cassette skin sensor in a proximal position after delivery of medicament.
Figure 20B:
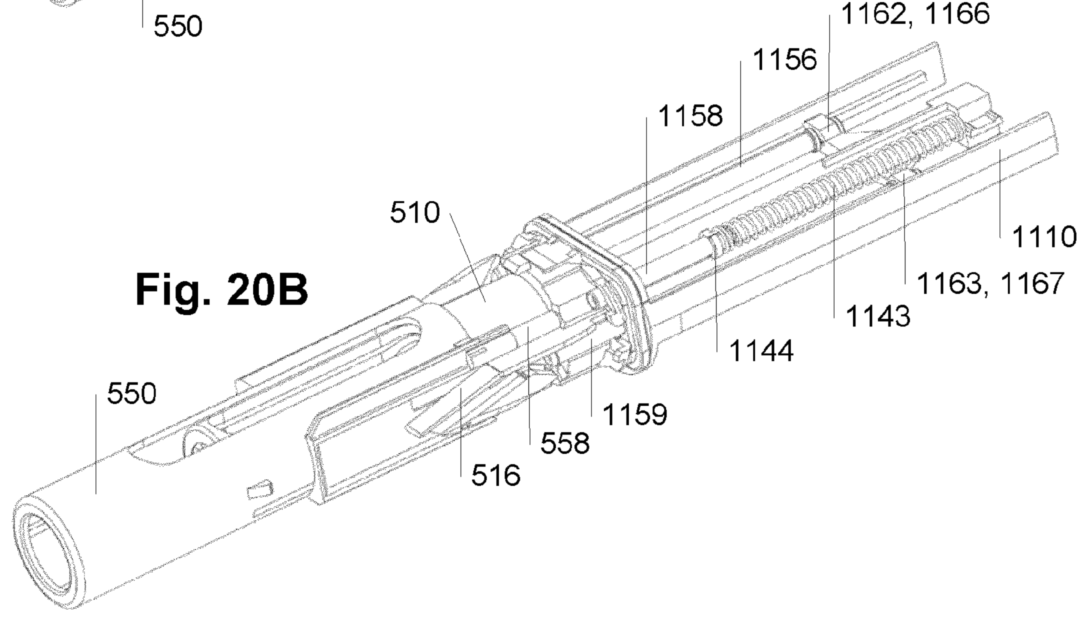
Figure 20C:
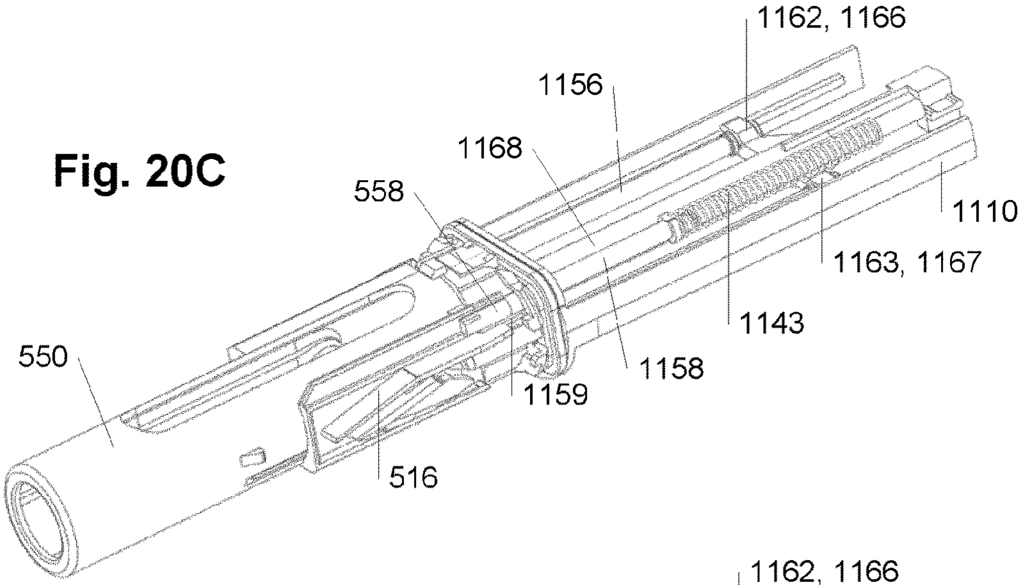
Figure 20D:
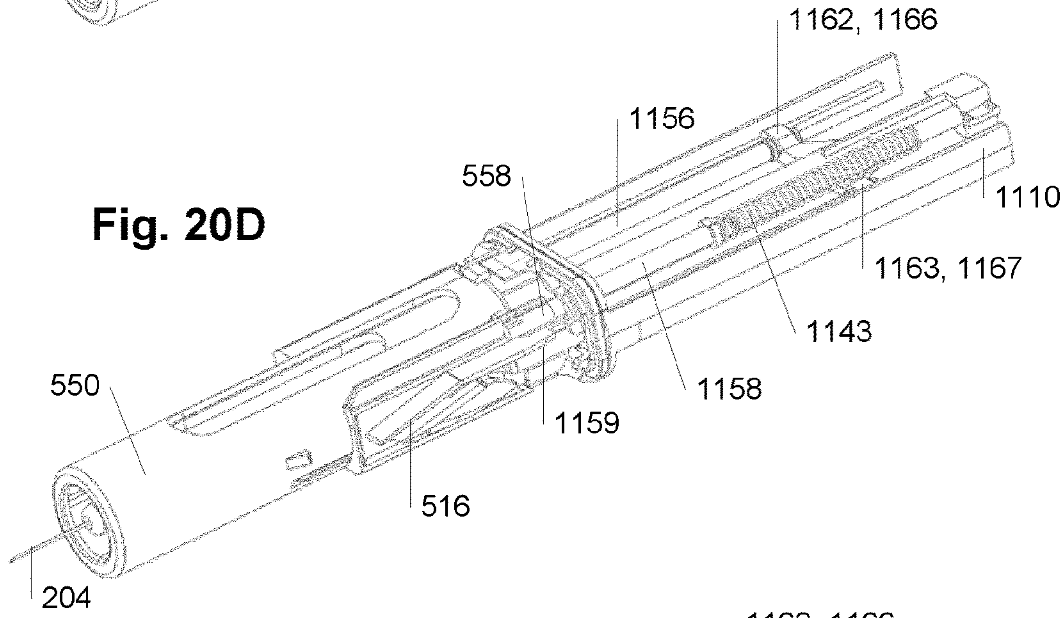
Figure 20E:
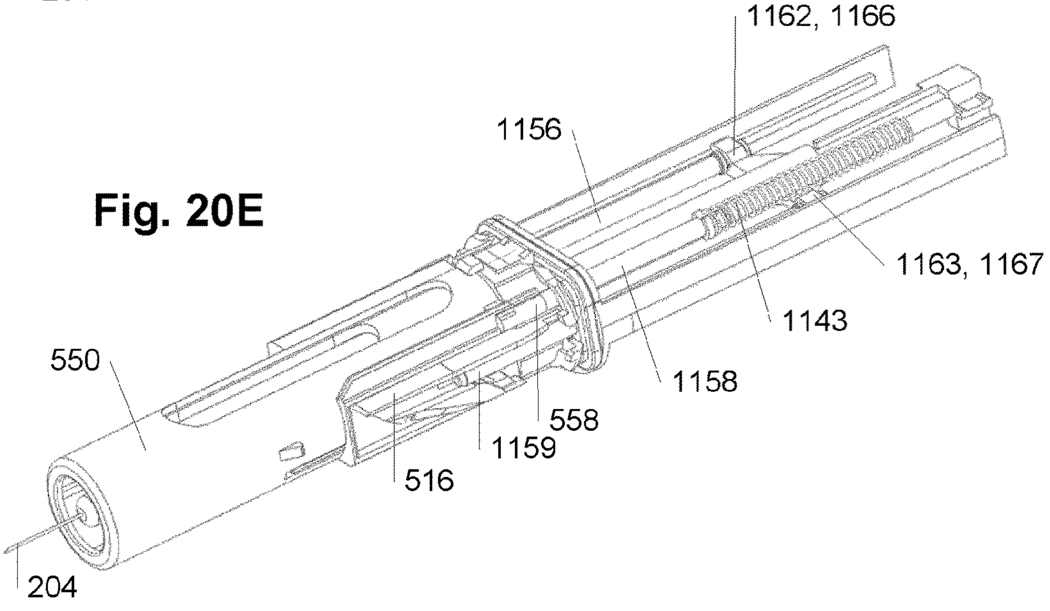
Figure 20F:
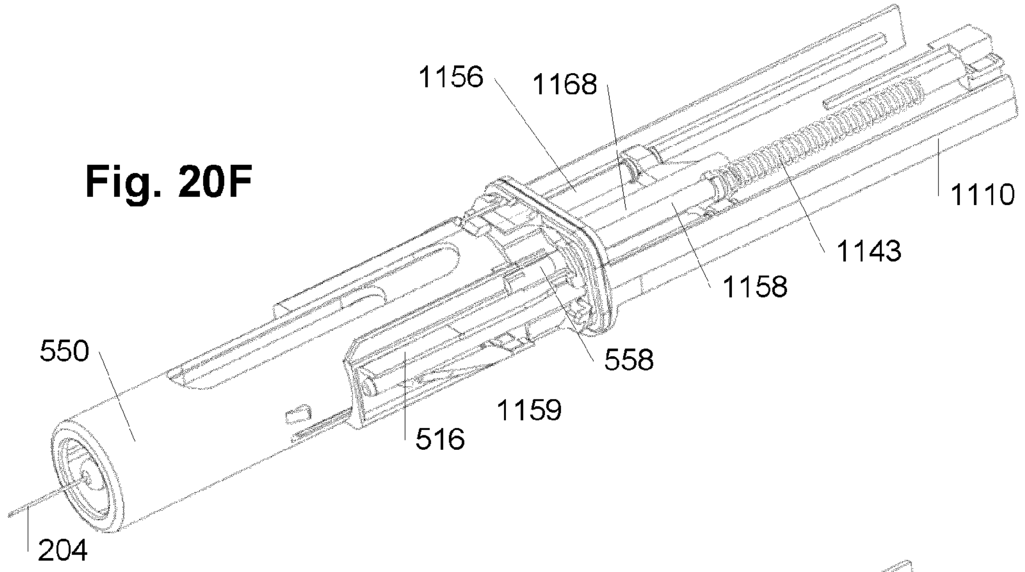
Figure 20G:
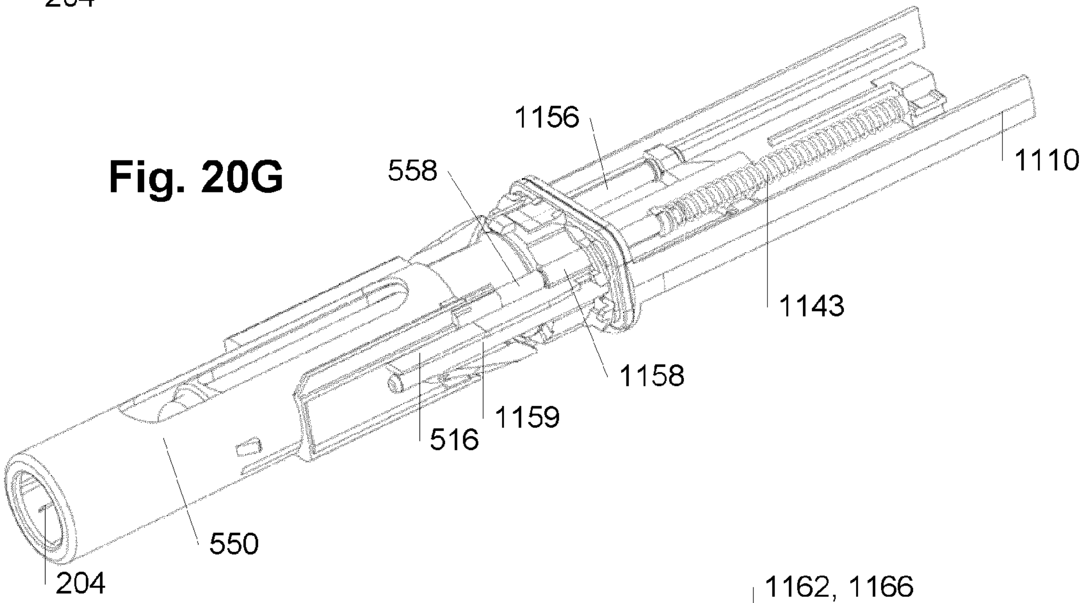
Figure 20H:
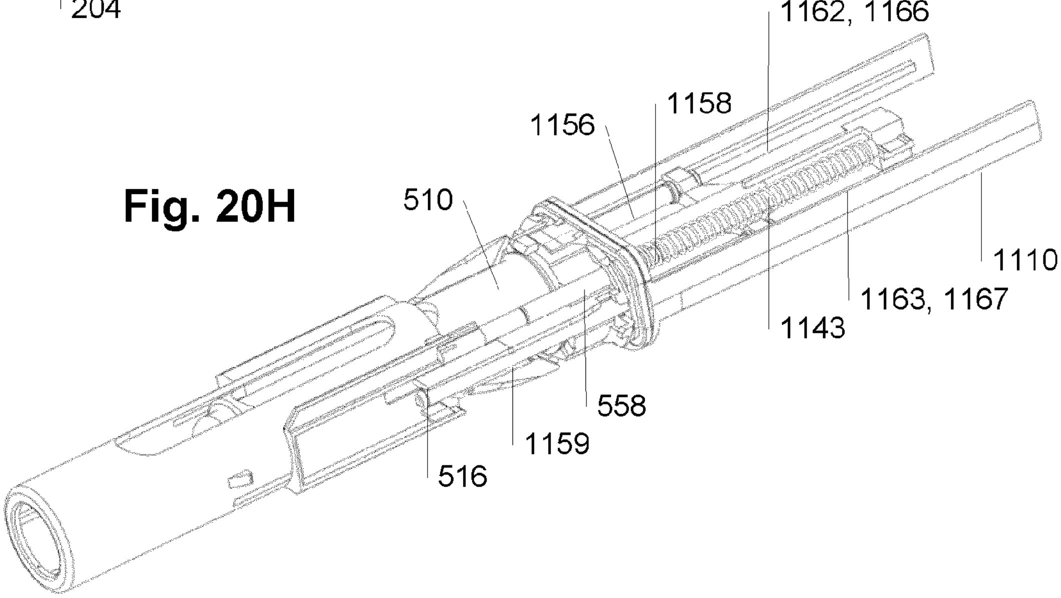
Figure 20I:
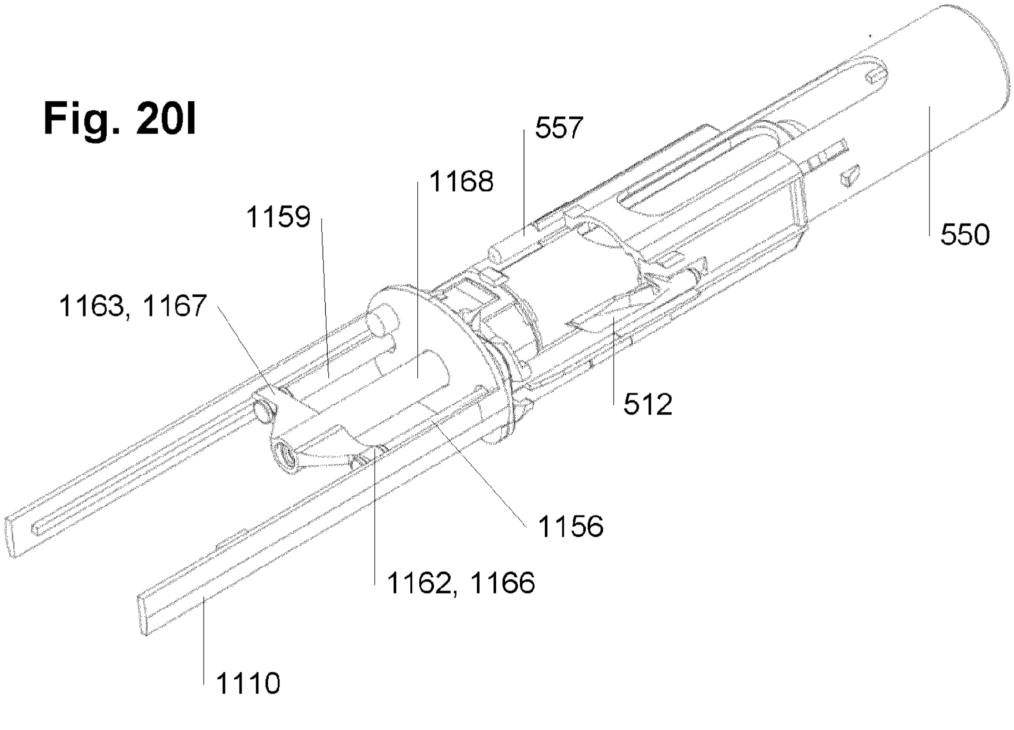

FIGS. 16-19 show an example of an auto injector 1000 for receiving the cassette of FIGS. 8-15. The auto injector 1000 is shown in an exploded view in FIG. 16, whereas FIGS. 17-19 show different views of the assembled auto injector 1000. For obtaining a clear view inside the auto injector, the outer housing 1102 has been omitted in FIGS. 16 and 19. The outer housing 1102 can be seen in FIGS. 17 and 18A-B. The housing 1102 is in one piece in this example of the auto injector. A two-part housing could also be imagined.

The cassette 500 is loaded into the auto injector 1000 in a front-loading configuration. Thus, the proximal end of the cassette 500 is inserted into the proximal end of the auto injector 1000 as illustrated in FIGS. 18A-B. As also seen in FIGS. 18A-B, the housing 1102 comprises an opening 1107, which facilitating inspection of the medicament in the cassette 500. The opening 1107 extends into the housing surface. Along a longitudinal axis of the injector housing 1102, the housing 1102 may be divided into two sections; a cassette covering section 1108 covering at least part of the cassette 500 when received inside the injector 1000, and a distal section 1106 covering internal injector parts. The cassette covering section 1108 is configured to extend to cover at least 10% of the cassette 500 when received inside the housing 1102 of the injector 1000 as shown in FIG. 18B. These internal injector parts are shown in FIG. 16 in the exploded view. The opening 1107 is in the cassette covering section 1108 and is extending in the longitudinal direction of the housing 1102.

The auto injector 1000 as shown in FIG. 16 comprises a cassette receiving chassis 1110 configured to receive the cassette 500. By receiving the cassette is meant to connect/couple with the cassette. The cassette 500 is interfacing with the auto injector 1000 at the distal end of the cassette 500, whereby the two parts are sharing the same longitudinal axis. This mitigates the risk of the cassette getting stuck inside in the auto injector. Further, it makes the connection as slim as possible. The only auto injector element, which extends in parallel with the cassette 500 when the cassette is inserted into the auto injector is normally the injector housing 1102, i.e. the cassette covering section 1108.

The internal injector parts include a drive module 1150, which is adapted to move a piston 1168. The piston 1168 is moved proximally pushing on the stopper 208 inside the syringe 200 whereby medicament can be expelled from the syringe 200. The piston 1168 has an inner threading (see FIG. 19), which engages with an outer threading on a led screw 1169. When the lead screw 1169 is rotated by the drive element 1150, the piston 1168 moves proximally. Rotation of the lead screw 1169 in the opposite direction, moves the piston 1168 distally. At the proximal end of the piston 1168 is a piston end plate 1178, which fits into an opening 1115 in the chassis 1110.

The drive module 1150 includes a motor 1151, which through a gear assembly rotates the led screw 1169. The gear assembly comprising a set of gears 1148, 1149, a led screw plate 1176, and a connecting ring between a chassis cover 1154 and the led screw 1169. Different versions of this gear set may also be imagined.

The chassis 1110 comprises a cassette abutting surface **1114*a* adapted for abutting a distal end 503, 506 of the cassette 500 when secured inside the auto injector 1000. The cassette abutting surface 1114*a* defines a proximal end plane from where substantially no internal injector parts extends in the proximal direction prior to assembling the cassette 500 and the auto injector 1000. By substantially is included that a minor tip, e.g. up to 2%, 5% or 10%, of the total length of one or more of the pins 1156, 1158, 1159 extends proximately outside the cassette abutting surface 1114*a*. Similarly, at the distal end of the internal injector parts, is a distal plane. At both the proximal plane and the distal plan of the internal injector parts, noise reducing material 1109, 1155 is positioned for dampening noise made by any internal injector parts during use. The noise reducing material 1109, 1155 may be a flexible material, such as rubber, and/or one or more O-ring(s), possibly in the form of square shaped O-rings as shown in FIG. 16**.

The drive element 1150 also controls the movement of a number of pins comprised in the auto injector 1000. As shown in FIG. 16, the number of pins may include; a first cassette locking pin 1156, a skin sensor pin 1158, and a second cassette locking pin 1159. The first locking pin 1156 and second locking pin 1159 are connected to the piston 1168. This is obtained by a first locking pin bridge connection 1162 and a second locking pin bridge connection 1163 on the piston 1168. The distal end 1166 of the first cassette locking pin 1156 is fixed to the first cassette locking pin bridge connection 1162 and the distal end 1167 of the second cassette locking pin 1159 is fixed to the second cassette locking pin bridge connection 1163. This enables the drive module 1150 to move the first cassette locking pin 1156, and the second cassette locking pin 1159 when moving the piston 1168. Alternatively, the movement of the two cassette locking pins 1156, 1159 can be decoupled from the movement of the piston 1168. Thus, the movement of the cassette locking pins can be individual or in the form of multiple pens moving simultaneously.

The skin sensor pin 1158 also moves with the piston 1168 as it moves proximally. The skin sensor 1158 is coupled to a spring system, which includes a spring 1143 and a stopper 1144 against which the spring 1143 presses in the proximal direction. The stopper 1144 is positioned in at the stopper accommodating part 1164 being the skin sensor. When the cassette 500 is positioned in the auto injector 1000 and the skin sensor pin 1158 is moved proximately, the skin sensor 1158 comes in contact with the second cassette skin sensor pin 558. As long as the cassette skin sensor 550 is pushed in the distal direction, it prevents the skin sensor pin 1158 from moving with the piston 1168 and two cassette locking pins 1156, 1158 is the proximal direction. This tensions the spring 1143. Since the tensioned spring 1143 acts on the skin sensor pin 1158, when releasing the cassette skin sensor 550, the spring 1143 pushes the cassette skin sensor 550 proximally. This ensures that the needle is not exposed after end delivery of medicament. The cassette skin sensor 550 is pushed into a locked position preventing distal movement of the cassette skin sensor 550. The distal locking is facilitated by the cassette skin sensor arm 566, where the locking surface 567 of the cassette skin sensor arm 566 locks into an inner opening in the cassette housing 540. Proximal movement of the cassette skin sensor 550 may also be prevented by an additional set of housing-skin sensor surfaces.

As the cassette locking pins 1156, 1159 move in parallel in a symmetric configuration in the auto injector shown in FIG. 16, the naming of 'first' and 'second' could be interchanged. Also, depending on the direction, which the cassette 500 is inserted into the auto injector 1000, the naming may change. By combining the features of the first and second syringe holder arms 512, 516, into one syringe holder arm, the second cassette locking pin 1159 and corresponding opening 1119 could be removed. This would require that the cassette 500 is inserted in a specific manner ensuring that the one cassette locking pin comes in contact with the one syringe holder arm.

The pins 1156, 1158, 1159 and the piston 1168 may also be referred to as cassette interacting parts adapted for securing and locking the cassette 500 inside the auto injector 1000 and for facilitating administering of the medicament. In common for the cassette interacting parts shown in FIG. 16 is that they move in parallel with the longitudinal axis of the auto injector 1000. The cassette interacting parts could possibly be configured for rotating around their own axis in addition to moving in parallel with the longitudinal axis of the auto injector. Also, the cassette interacting parts may be prevented from moving in directions different from parallel with the longitudinal axis of the auto injector.

The cassette receiving chassis 1110 configured to receive a cassette 500. The cassette receiving chassis 1110 is extending from a proximal end 1111 to a distal end 1112, where at the distal end, distally extending chassis arms 1113 are found. At the proximal end 1111 of the chassis 1110 is a proximal chassis part 1114 with a number of openings including a piston opening 1115, a first pin opening 1116, a second pin opening 1117, a third pin opening 1118, and a fourth pin opening 1119. Depending on the number of pins in the auto injector, fewer openings could also be used. The openings are round circular openings, but may also have a different shape mimicking the shape of the pins if they are not round.

When the cassette 500 is positioned in the auto injector 1000, the piston opening 1115 is aligned with piston opening 525 in the syringe holder 510 to allow the auto injector piston 1168 to extend there through. Likewise, the first pin opening 526 in the syringe holder 510 is aligned with the first pin opening 1116 such that the first cassette locking pin 1156 can pass through both openings to deflect the first syringe holder arm 512 thereby unlocking the cassette skin sensor 550 from the syringe holder 510 as explained earlier in connection with FIGS. 7A-G.

The second pin opening 1117 in the proximal chassis part 1114 is aligned with the second pin opening 527 in the syringe holder 510 for allowing passage of the first cassette skin sensor pin 557 of the cassette skin sensor 550 to pass there through. The second pin opening 1117 does not extend all the way through, but instead has an end surface 1121 (see FIG. 7G), which stops the first cassette skin sensor pin 557 of the cassette skin sensor 550 in its distal movement towards the auto injector. If the first cassette skin sensor pin 557 is shortened, the second pin opening 1117 can be eliminated and the first cassette skin sensor pin 557 instead be stopped by the proximal chassis part 1114.

The third pin opening 1118 is aligned with the third pin opening 528 in the syringe holder 510 for allowing passage of the skin sensor pin 1158, and/or the second cassette skin sensor pin 558 there through. This was also shown and discussed in connection with the auto injector in FIGS. 7A-F. The fourth pin opening 1119 is aligned with the fourth pin opening 529 in the syringe holder 510 for allowing passage of the second cassette locking pin 1159 there through.

When the cassette 500 is positioned in the auto injector 1000, the cassette locking pins 1156, 1159 pass into the pin openings 526, 529 in the cassette 500 and push cassette locking protrusions 539 into the auto injector housing 1102, where internal parts inside the injector housing 1102 prevent the proximal movement of the cassette housing 530, thereby locking the cassette 500 to the auto injector 1000. As the cassette locking pins 1156, 1159 moves further into the cassette 500, the first cassette locking pin 1156 deflects the first syringe holder arm 512. This causes a release of the cassette skin sensor 550 allowing it to move towards the syringe holder 510, i.e. a distal direction movement of the cassette skin sensor 550. The syringe holder 510 and the skin sensor 550 are longitudinally movable relative to each other upon release of the skin sensor 550 from the syringe holder 510. By pressing the auto injector against the patient's skin will allow the needle to be inserted into the patient as movement of the cassette skin sensor 550 distally exposes the needle.

Upon movement of the cassette skin sensor 550 towards the syringe holder 510, the first cassette skin sensor pin 557 moves towards—and possibly through—the second pin opening 527 in the syringe holder 510. Similarly, the second cassette skin sensor pin 558 moves towards—and possibly through—the third pin opening 528 in the syringe holder 510 when the cassette skin sensor 558 moves distally. When the second cassette skin sensor pin 558 passes through the openings 528, 1118 it comes in contact with the skin sensor pin 1158 as described above.

The further movement of the cassette locking pins 1156, 1159 into the cassette 500, causes the second cassette locking pin 1159 to deflect the second syringe holder arm 516. This releases the cassette skin sensor 550 allowing it to move away from the syringe holder 510 in the proximal direction. Thus, when/if the user removes the auto injector from the patient's skin, the cassette skin sensor 550 is now allowed to move proximally to cover the needle after end medicament injection. The spring 1143 acting on the skin sensor pin 1158 ensures that the cassette skin sensor 550 is locked after use as described above.

The auto injector as shown in FIG. 16 also comprises a printed circuit board (PCB) 1180, a USB connection 1181, USB PCB plate 1182, and a battery 1184. On the PCB board 1180 is also positioned a number of switches 1171*a*, 1171*b*, 1171*c* for detecting the position of the pins inside the auto injector.

FIG. 17 shows the assembled auto injector 1000 in a view as seen from the front where the cassette 500 is inserted. The cassette abutting surface 1114*a* defines a proximal end plane from where substantially no internal injector parts extends proximally prior to assembling the cassette 500 and the auto injector 1000. By substantially is included a situation where only a minor part of the internal injector parts protrude a small amount, such as up 2%, 5%, or 10% proximally compared to the cassette abutting surface 1114*a*. This is shown in FIG. 19, where the tip of the second cassette locking pin 1159 protrudes outside the cassette abutting surface 1114*a*. The pins 1156, 1158, 1159 are also indicated in FIG. 17.

The cassette abutting surface 1114*a* may also define a proximal end plane from where substantially no cavities extends distally into the distal section 1106. By substantially is here also included that a small closed well-type opening is present in the surface 1114*a* as illustrated in FIG. 7G, item 1121.

The smooth cassette abutting surface 1114*a* and the supporting plate 1114*b* behind it, ensure that the auto injector can be kept clean in an easy manner due to avoidance of grooves to e.g. collect dirt and dust etc. Also, a user is prevented from accessing the internal parts of the auto injector. This prolongs the lifetime of the auto injector 1000.

FIGS. 20A-I shows the interaction between the cassette 500 of FIGS. 8-15 and the auto injector of FIGS. 16-19. Compared to FIGS. 7A-G, the cassette release pins 1156, 1159 has switched position such that the second cassette release pin 1159 is positioned next to the skin sensor pin 1158. As the cassette release pins 1156, 1158 are working in an interchangeable manner and move together, this has no impact on the interaction between the auto injector 1000 and the cassette 500. Also, compared to FIGS. 7A-G, FIGS. 20A-I show the cassette 500 turned 180 degrees, thereby showing the second syringe holder arm 516 and the second cassette locking pin 1159 in FIGS. 20A-H instead of the first syringe holder arm 512 and the first cassette locking pin 1156 as in FIGS. 7A-F.

The cassettes 500 and auto injectors 1000 are shown and described in a configuration using manual insertion of the needle. An automatic needle insertion could also be envisioned by included a spring-motor system.

REFERENCES

200 syringe
201 proximal end of the syringe/syringe compartment
202 syringe compartment
203 distal end of the syringe/syringe compartment
204 hollow needle
205 distal end surface of the syringe
206 rigid needle shield
207 inner part of the rigid needle shield
208 stopper
210 plunger rod
500 cassette

501 inner cassette part
502 proximal end of the inner cassette part
503 distal end of the inner cassette part
504 outer cassette part
505 proximal end of the outer cassette part
506 distal end of the outer cassette part
**507*a*** syringe holder ring
**507*b*** syringe holder ring
508 proximal end of the syringe holder
509 distal end of the syringe holder
510 syringe holder
511 syringe holder support tube
512 first syringe holder arm
513 proximal end of the first syringe holder arm
514 proximal surface at the proximal end of the first syringe holder arm
515 syringe locking protrusion
516 second syringe holder arm
517 proximal end of the second syringe holder arm
518 distal surface at the proximal end of the second syringe holder arm
519 syringe holder plate
520 proximal support surface of the syringe holder plate
521 distal support surface of the syringe holder plate
522 first syringe holder locking arm
523 second syringe holder locking arm
524 syringe holder locking protrusions housing
525 piston opening in the syringe holder plate
526 first pin opening in the syringe holder plate
527 second pin opening in the syringe holder plate
528 third pin opening in the syringe holder plate
529 fourth pin opening in the syringe holder plate
530 cassette cap
531 first part positioned between the rigid needle shield and the proximal end of the syringe compartment
532 proximal end of the cassette cap
534 distal end of the cassette cap
535 inner rigid needle shield tube
536 outer rigid needle shield tube
537 distal end of the cassette cap
538 proximal end of the cassette cap
539 cassette locking protrusion
540 cassette housing
541 proximal end of the cassette housing
542 distal end of the cassette housing
543 distal end surface of the cassette housing
544 locking opening in the cassette housing
545 skin sensor housing opening
546 housing shoulder
547 opening in the housing for inspection of medicament
548 protruding rail on the inside of the cassette housing
549 syringe locking arms
550 cassette skin sensor
552 distal end of the cassette skin sensor
553 first locking protrusion
554 second locking protrusion
556 opening for inspection of the syringe
557 first cassette skin sensor pin
558 second cassette skin sensor pin
560 proximal end of the cassette skin sensor
562 skin touching surface of the cassette skin sensor
566 cassette skin sensor arm
567 locking surface of the cassette skin sensor arm
568 cassette skin sensor rail to fit into the rails inside the cassette housing
570 cassette sleeve
571 proximal part of the cassette sleeve
572 distal part of the cassette sleeve
573 sleeve arms on the cassette sleeve
574 sleeve locking protrusion
575 inner helical surface part
576 opening in the cassette sleeve
577 end surface point on the inner helical surface part
580 opening in the syringe holder
1000 auto injector
1102 housing
1103 proximal end of the housing
1104 distal end of the housing
1105 protruding tab on the inside of the housing
1106 distal section of the housing covering internal injector parts
1107 opening in the housing
1108 cassette covering section
1109 noise reducing material/O-ring
1110 cassette receiving chassis
1111 proximal end of the chassis
1112 distal end of the chassis
1113 distally extending chassis arm
1114 proximal chassis part
**1114*a*** proximal surface of the proximal chassis part/cassette abutting surface
**1114*b*** support plate
1115 piston opening in the proximal chassis part
1116 first pin opening in the proximal chassis part
1117 second pin opening in the proximal chassis part
1118 third pin opening in the proximal chassis part
1119 fourth pin opening in the proximal chassis part
1120 fifth opening in the proximal chassis part
1121 end surface of the second pin opening
1140 spring system acting on the skin sensor
1141 spring guidance pin
1142 supporting chassis for guiding the skin sensor pin
1143 spring in the spring system acting on the skin sensor
1144 stopper for stopping the spring in the spring system acting on the skin sensor
1148 gear
1149 gear
1150 drive module
1151 motor
1152 gear cover
1153 gear assembly
1154 chassis cover
1155 noise reducing material/O-ring
1156 first cassette locking pin
1158 skin sensor pin
1159 second cassette locking pin
1160 cassette detection pin
1161 guide pin for the skin sensor pin
1162 first locking pin bridge connection
1163 second locking pin bridge connection
1164 stopper accommodating part
1166 distal end of the first cassette locking pin connecting to the bridge connection
1167 distal end of the second cassette locking pin connecting to the bridge connection
1168 piston internally threaded to match the led screw
1169 led screw
1170 bridge
1171 switch
**1171*a*** switch
**1171*b*** switch
**1171*c*** switch
1172 opening in the chassis cover

1174 connecting ring between the chassis cover and led screw
1176 led screw plate
1178 piston end plate
1180 printed circuit board
1181 USB connection
1182 USB printed circuit board plate
1184 battery

The invention claimed is:

1. An auto injector for receiving a cassette with medicament and for administering the medicament in the cassette to a patient, the auto injector comprising:

a housing extending from a proximal end to an opposite distal end along a longitudinal direction and which defines a longitudinal axis, wherein the cassette is configured to be removably received in the housing along the longitudinal direction;

a piston configured for proximal movement of a stopper comprised within the cassette;

one or more cassette interacting parts adapted for engagement with the cassette to lock the cassette to the housing, wherein after the cassette has been positioned in the housing, the one or more cassette interacting parts are configured to move in a proximal direction and only in parallel with the longitudinal axis of the housing during locking of the cassette to the housing; and a drive module adapted for moving the piston and the one or more cassette interacting parts in the proximal direction in parallel with the longitudinal axis of the housing for locking the cassette inside the housing and for facilitating administering of the medicament.

2. The auto injector according to claim 1, further comprising multiple internal injector parts positioned inside the housing, wherein the housing includes a cassette covering section configured to extend to cover at least a part of the cassette when received inside the housing, and a distal section configured to extend to cover the internal injector parts before the cassette is positioned inside the housing.

3. The auto injector according to claim 1, further comprising a cassette abutting surface adapted for abutting a distal end of the cassette when the cassette is positioned inside the housing, the cassette abutting surface defining a proximal end plane from where substantially no internal injector parts extend proximally prior to assembling the cassette and the housing.

4. The auto injector according to claim 1, wherein the one or more cassette interacting parts includes a first cassette locking pin and skin sensor pin, and a cassette detection pin and/or a second cassette locking pin.

5. The auto injector according to claim 4, further comprising a chassis defining a proximal end and a distal end, the chassis including a proximal chassis part at the proximal end of the chassis, the proximal chassis part comprising one or more openings adapted for allowing passage of the first cassette locking pin or the piston through each opening after or during locking of the cassette inside the housing.

6. The auto injector according to claim 5, wherein the one or more openings comprises:

a piston opening for allowing passage of the piston therethrough, a first pin opening for allowing passage of the first cassette locking pin therethrough, and a third pin opening for allowing passage of the skin sensor pin therethrough; and/or wherein the one or more openings further comprises one or more of:

a second pin opening for allowing passage of a first cassette skin sensor pin comprised in the cassette, and/or a fourth pin opening for allowing passage of the second cassette locking pin therethrough, and/or a fifth pin opening for allowing passage of the cassette detection pin therethrough.

7. The auto injector according to claim 4, wherein the drive module is further configured for moving the first cassette locking pin, and/or the skin sensor pin, and/or the second cassette locking pin in the proximal direction along the longitudinal axis.

8. The auto injector according to claim 7, wherein the first cassette locking pin and the second cassette locking pin are locked to the piston such that the piston and the first and second cassette locking pins move together along the longitudinal axis.

9. The auto injector according to claim 1, wherein the housing forms a cavity into which the cassette is configured to be received, wherein an abutting surface is provided within the cavity, the abutting surface defining a proximal end plane, wherein less than 5% of a total length of all of the one or more of the cassette interacting parts extend proximally from the proximal end plane before the cassette is positioned in the auto injector.

10. The auto injector according to claim 9, wherein the one or more cassette interacting parts extend proximally from the proximal end plane after the cassette has been positioned in the housing.

11. The auto injector according to claim 1, wherein the one or more cassette interacting parts comprise one or more injector pins.

12. The auto injector according to claim 11, wherein the one or more injector pins includes a first cassette locking pin and a skin sensor pin, and wherein the drive module is adapted for moving the piston and the first cassette locking pin together.

13. The auto injector according to claim 11, further comprising a chassis defining a proximal end and a distal end, the chassis including a proximal chassis part at the proximal end of the chassis, the proximal chassis part comprising one or more openings adapted for allowing passage of the one or more injector pins through the one or more openings after or during locking of the cassette inside the housing.

14. An auto injector for receiving a cassette with medicament and for administering the medicament, the auto injector comprising:

a housing extending from a proximal end to an opposite distal end along a longitudinal direction and which defines a longitudinal axis, the housing including:

a cassette covering section configured to extend to cover at least 10% of the cassette when received inside the housing, and a distal section extending from the cassette covering section;

internal injector parts within the housing, wherein the distal section covers all internal injector parts, the internal injector parts including one or more cassette interacting parts adapted to lock the cassette inside the housing; and a cassette abutting surface adapted for directly abutting a distal surface of the cassette when the cassette is positioned inside the housing, the distal surface of the cassette being the most distal surface of the cassette, the cassette abutting surface defining a proximal end plane from where substantially no internal injector parts extend proximally prior to assembling the cassette and the housing.

15. The auto injector according to claim 14, wherein the internal injector parts further include at least a piston configured for movement to administer the medicament, a drive module adapted for moving the piston proximately, and a chassis, wherein the internal injector parts are defined by a proximal end plane and a distal end plane; and noise reducing material at the proximal end plane of the internal injector parts and noise reducing material at the distal end plane of the internal injector parts.

16. The auto injector according to claim 14, wherein the one or more cassette interacting parts are further adapted for facilitating administration of the medicament, wherein the one or more cassette interacting parts does not extend proximally from the proximal end plane prior to locking the cassette inside the housing, wherein the one or more cassette interacting parts are adapted for moving in a proximal direction after the cassette has been positioned in the housing, whereby at least a part of one or more of the cassette interacting parts are extending proximally from the proximal end plane.

17. The auto injector according to claim 14, wherein the cassette comprises a syringe holder configured to receive the syringe with the medicament.

18. A system comprising:

a cassette including a syringe compartment containing medicament and extending from a proximal end to a distal end, wherein the proximal end is adapted for being in connection with a hollow needle through which the medicament is allowed to exit the syringe compartment, a stopper movable from a distal position to a proximal position inside the syringe compartment for emptying the syringe compartment, and a syringe holder extending around at least part of the syringe compartment; and an auto injector for removably receiving the cassette and for administering the medicament in the cassette to a patient, the auto injector including an auto injector housing extending from a proximal end to a distal end along a longitudinal direction and which defines a longitudinal axis, a piston adapted for proximal movement of the stopper in parallel with the longitudinal axis, and one or more cassette interacting parts adapted for engaging with and locking the cassette inside the auto injector housing and for facilitating administering of the medicament, a drive module adapted for moving the piston and the one or more cassette interacting parts in the proximal direction in parallel with the longitudinal axis of the housing, wherein after the cassette has been positioned in the housing, the one or more cassette interacting parts are configured for only moving in parallel with the longitudinal axis of the auto injector housing during locking of the cassette to the housing and during administration of the medicament, and wherein the stopper is movable by the piston for emptying the syringe compartment.

19. The system according to claim 18, wherein the cassette is adapted for being received in the auto injector by movement of the cassette and the auto injector towards each other along a shared longitudinal axis without significant rotation of the cassette around the shared longitudinal axis.

20. The system according to claim 18, wherein the cassette further comprises the hollow needle in fluid connection with the proximal end of the syringe compartment, and a rigid needle shield connected to the proximal end of the syringe compartment and adapted for covering the hollow needle, wherein the syringe compartment, the hollow needle and the stopper are part of a syringe fixed inside the syringe holder.

21. The system according to claim 18, wherein the one or more cassette interacting parts includes a first cassette locking pin, and wherein the cassette is locked in the auto injector when the drive module moves the first cassette locking pin proximally.

22. The system according to claim 18, wherein the one or more cassette interacting parts includes a first cassette locking pin, and wherein the cassette further comprises a cassette skin sensor, and wherein when the drive module moves the first cassette locking pin in a proximal direction, the cassette skin sensor is adapted for being distally unlocked from the syringe holder allowing for distal movement of the cassette skin sensor.

23. The system according to claim 22, wherein the one or more cassette interacting parts includes a second cassette locking pin, and wherein when the drive module moves the second cassette locking pin in the proximal direction, the cassette skin sensor is adapted for being proximally unlocked from the syringe holder allowing for proximal movement of the cassette skin sensor relative to the syringe holder.

24. The system according to claim 23, wherein the cassette further comprises a cassette skin sensor pin, and wherein the auto injector further comprises a skin sensor pin and a skin sensor spring system adapted for pushing the skin sensor pin of the auto injector against the cassette skin sensor pin of the cassette at least after release of the cassette skin sensor from the syringe holder by movement of the first cassette locking pin and/or the second cassette locking pin in the proximal direction, wherein the skin sensor spring system is adapted for pushing the cassette skin sensor in the proximal direction into a locked position preventing movement of the cassette skin sensor in a distal direction.

25. The system according to claim 18, wherein the auto injector further comprises a cassette covering section configured to extend to cover at least a part of the cassette when received inside the auto injector housing, and the cassette covering section comprising at least one opening extending in the longitudinal direction of the auto injector housing, wherein the cassette comprises a cassette housing having at least one opening extending along a longitudinal axis of the cassette housing, wherein the at least one opening in the cassette housing and the at least one opening in the cassette covering section are aligned when the cassette is positioned inside auto injector to facilitate inspection of the medicament in the syringe compartment, wherein the cassette covering section and the cassette housing each comprise two openings extending in the longitudinal direction on opposite sides of the auto injector housing and the cassette housing, respectively, wherein the openings are aligned when the cassette is positioned inside the auto injector to facilitate inspection of the medicament in the syringe compartment from two opposite directions.

26. The system according to claim 25, wherein the cassette covering section comprises interior guiding tracks in parallel with the longitudinal direction configured for guiding the cassette to a correct position when inserting the cassette into the cassette covering section, wherein the interior guiding tracks form part of the at least one opening inside the cassette covering section of the auto injector housing.

* * * * *